（12） United States Patent
Yang et al.

(10) Patent No.: US 12,036,274 B2
(45) Date of Patent: Jul. 16, 2024

(54) RECOMBINANT MPT PROTEIN DERIVED FROM MPT63 AND MPT64 AND USE THEREOF

(71) Applicant: INDUSTRY-UNIVERSITY COOPERATION FOUNDATION HANYANG UNIVERSITY ERICA CAMPUS, Gyeonggi-do (KR)

(72) Inventors: Chul-Su Yang, Gyeonggi-do (KR); Jae-Sung Kim, Gyeonggi-do (KR)

(73) Assignee: Industry-University Cooperation Foundation Hanyang University Erica Campus, Gyeonggi-Do (KR)

( * ) Notice: Subject to any disclaimer, the term of this patent is extended or adjusted under 35 U.S.C. 154(b) by 113 days.

(21) Appl. No.: 17/736,708

(22) Filed: May 4, 2022

(65) Prior Publication Data
US 2022/0378893 A1    Dec. 1, 2022

(30) Foreign Application Priority Data

May 18, 2021 (KR) ........................ 10-2021-0063804

(51) Int. Cl.
*A61K 39/04*    (2006.01)
*A61P 31/06*    (2006.01)

(52) U.S. Cl.
CPC .............. *A61K 39/04* (2013.01); *A61P 31/06* (2018.01)

(58) Field of Classification Search
None
See application file for complete search history.

(56) References Cited

U.S. PATENT DOCUMENTS 10,611,818 B2 *    4/2020    Schøller .......... G01N 33/56972

OTHER PUBLICATIONS

Printout of U.S. Pat. No. 10611818 B2 Apr. 7, 2020.*
Kim et al., "Multi-Functional MPT Protein as a Therapeutic Agent against *Mycobacterium tuberculosis*", Biomedicines, vol. 9, No. 545, 20 pages (2021).
Mohammadi Tashakkori et al. "Production of MPT-64 recombinant protein from virulent strain of *Mycobacterium bovis*", Iranian Journal of Veterinary Research, 2018, vol. 19, No. 2, pp. 108-112.

* cited by examiner

*Primary Examiner* — Oluwatosin A Ogunbiyi
(74) *Attorney, Agent, or Firm* — Armstrong Teasdale LLP

(57) ABSTRACT

The present disclosure is the first to identify a host cell protein and its function with which MPT63 and MPT64, secreted antigens of *Mycobacterium tuberculosis*, interact, and to construct a recombinant MPT protein including each domain of MPT63 and MPT64 interacting with the host cell protein, and the recombinant MPT protein may be applied to a use for the prevention and treatment of tuberculosis by confirming that the recombinant MPT protein targets the *Mycobacterium tuberculosis*-infected macrophages and increases the ROS level and inflammatory cytokine expression in macrophages, thereby inducing the death of *Mycobacterium tuberculosis*. And MPT protein of the present disclosure can improve the vaccine effect by the BCG vaccine so that it can be used as a tuberculosis vaccine and/or vaccine adjuvant either alone or together with known tuberculosis vaccines.

16 Claims, 62 Drawing Sheets
Specification includes a Sequence Listing.

rMPT63 interacts with

NP_037386, TANK binding kinase 1, TBK1

$^{39}$VFNNISFLR$^{47}$
$^{155}$LTDFGAAR$^{162}$
$^{205}$WSIGVTFYHAATGSLPF$^{221}$
$^{256}$PIDWSGDMPVSCSLS$^{270}$
$^{345}$IISSNQELIYEG$^{356}$
$^{462}$TEVVITLDFCIR$^{473}$
$^{674}$TPIYPSSNTLVEMTL$^{688}$

NP_000256, Neutrophil cytosol factor 1, p47phox

$^{8}$HIALLGFEKRFV$^{19}$
$^{32}$WQDLSEKVVYRRFTEIY$^{48}$
$^{72}$IPHLPAPKWFDGQRA$^{86}$
$^{314}$RSRKRLSQDAYRR$^{326}$
$^{347}$SPLEEERQTQRSK$^{360}$
$^{365}$VPPRPSADLI$^{374}$

FIG. 2C rMPT64 interacts with

NP_037386, TANK binding kinase 1, TBK1

$^{70}$LFAIEEETTTR$^{80}$
$^{104}$AYGLPESEFLIVL$^{116}$
$^{292}$CWGFDQFFAETSDILHR$^{308}$
$^{373}$TTEENPIFVVSR$^{384}$
$^{417}$AITGVVCYACR$^{427}$

NP_000180, Hexokinase 2, HK2

$^{22}$VDQYLYHMR$^{30}$
$^{63}$MLPTFVRSTPDGT$^{75}$
$^{78}$GEFLALDLGGTNF$^{90}$
$^{324}$LSPELLNTGR$^{333}$
$^{452}$GAAMVTAVAYR$^{462}$
$^{744}$MISGMYLGEIVR$^{755}$

FIG. 2D

TBK1 peptide (MPT63/64)
R9(RRRRRRRRR)-MPT63 $_{50}$VVLGWKV$_{56}$-GG-MPT64$_{24}$APKTY$_{28}$-GG-$_{34}$GTDTG$_{38}$ TBK1 peptide (MPT63) R9(RRRRRRRRR)-M Recombinant multi-functional MPT protein CPP-Macrophage-p47phox-TBK1

R9 -GG- MPTB4 (YQNFAVT)₁₀ -GG- MPTB3 (EDLLWE)₅ -GG- MPTB3 (VVLGWAV)₅ -GG- MPTM (APKTY -GG- GTDTG)₅

FIG. 9A

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: TBK1 binding domain derived from MPT63

<400> SEQUENCE: 1
```

```
Val Val Leu Gly Trp Lys Val
1               5

<210> SEQ ID NO 2
<211> LENGTH: 7
<212> TYPE: PRT
<213> ORGANISM: Artificial Sequence
<220> FEATURE:
<223> OTHER INFORMATION: P47phox binding domain derived from MPT63

<400> SEQUENCE: 2

Glu Asp Leu Leu Ile Trp Glu
1               5

<210> SEQ ID NO 3
<211> LENGTH: 5
<212> TYPE: PRT
<213> ORGANISM: Artificial Sequence
<220> FEATURE:
<223> OTHER INFORMATION: TBK1 binding domain derived from MPT64

<400> SEQUENCE: 3

Ala Pro Lys Thr Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: TBK1 binding domain derived from MPT64

<400> SEQUENCE: 4

Gly Thr Asp Thr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: HK2 binding domain derived from MPT64

<400> SEQUENCE: 5

Tyr Gln Asn Phe Ala Val Thr
1               5

<210> SEQ ID NO 6
<211> LENGTH: 7
<212> TYPE: PRT
<213> ORGANISM: Artificial Sequence
<220> FEATURE:
<223> OTHER INFORMATION: TBK1 binding peptide
<220> FEATURE:
<221> NAME/KEY: VARIANT
<222> LOCATION: (4)..(4)
<223> OTHER INFORMATION: Xaa is any one of all amino acids

<400> SEQUENCE: 6

Val Val Leu Xaa Trp Lys Val
1               5

<210> SEQ ID NO 7
<211> LENGTH: 7
<212> TYPE: PRT
<213> ORGANISM: Artificial Sequence
<220> FEATURE:
<223> OTHER INFORMATION: P47phox binding peptide
```

```
-continued

<220> FEATURE:
<221> NAME/KEY: VARIANT
<222> LOCATION: (4)..(4)
<223> OTHER INFORMATION: Xaa is any one of all amino acids
<220> FEATURE:
<221> NAME/KEY: VARIANT
<222> LOCATION: (5)..(5)
<223> OTHER INFORMATION: Xaa is any one of all amino acids
<220> FEATURE:
<221> NAME/KEY: VARIANT
<222> LOCATION: (6)..(6)
<223> OTHER INFORMATION: Xaa is any one of all amino acids

<400> SEQUENCE: 7

Glu Asp Leu Xaa Xaa Xaa Glu
1               5
```

RECOMBINANT MPT PROTEIN DERIVED FROM MPT63 AND MPT64 AND USE THEREOF

CROSS-REFERENCE TO RELATED APPLICATION

This application claims the benefit of Korean Patent Application No. 10-2021-0063804 filed on May 18, 2021, in the Korean Intellectual Property Office, the entire disclosure of which is incorporated herein by reference for all purposes.

REFERENCE TO AN ELECTRONIC SEQUENCE LISTING

The contents of the electronic sequence listing (38009-16_ST25.txt; Size: 1,930 bytes; and Date of Creation: Apr. 14, 2022) are herein incorporated by reference in their entirety.

BACKGROUND

1. Field of the Disclosure

The present disclosure identifies host proteins that interreact with MPT63 and MPT64, secreted proteins of *Mycobacterium tuberculosis*, and elucidates the function of each interaction, produces recombinant proteins derived from MPT63 and MPT64, and uses them for the prevention or treatment of *Mycobacterium tuberculosis* infectious diseases.

2. Description of the Related Art

Tuberculosis (TB), caused by *Mycobacterium tuberculosis* (MTB), is one of the world's most important infectious diseases due to its high mortality. *Mycobacterium tuberculosis* infects the host's macrophages and survives by evading the host's immune system. A number of immune proteins that interact with *Mycobacterium tuberculosis* in host cells have not yet been clearly identified, and *Mycobacterium tuberculosis* maintains survival and proliferation in lung granulomas by interacting with various immune proteins in host cells.

The functions of many secreted proteins of *Mycobacterium tuberculosis* are still unknown. Secreted antigens of *Mycobacterium tuberculosis* are essential for regulating immune responses and interacting with host proteins for bacterial proliferation and survival. Proteins secreted during infection may determine pathways in the acquired immune system, such as activation of reactive T cells. Therefore, investigating the precise role of secretory antigens is essential to understanding the pathogenicity of *Mycobacterium tuberculosis*.

MPT63 and MPT64 are immunodominant secretory antigens of *Mycobacterium tuberculosis*, their secretion is increased in active tuberculosis, and they are detected in macrophages of tuberculosis lesions. MPT63 induces apoptosis of macrophages through host pH-dependent compatibility switches. Further, MPT63 is known to enhance phagocytosis by regulating the secretion of TNF-α and IL-6 in peritoneal macrophages of mice. MPT64 encoded in the RD2 region is known to induce IFN-γ production and increase TGF-β expression in rat macrophages and tuberculosis patients, thereby reducing inflammation and inhibiting apoptosis. MPT63 and MPT64 are used as disease markers for tuberculosis, and many studies are being conducted as potential candidates for tuberculosis vaccines. However, the mechanism of interaction between MPT63 and MPT64 remains unclear.

The immune signaling pathway in tuberculosis begins with pathogen recognition by pattern recognition receptors such as TLR, NLR, CLR, and scavenger receptors. Increased expression of inflammatory cytokines and chemokines and production of reactive oxygen species through activation of the NF-κB signaling pathway are essential for removing active MTB from the host.

Nevertheless, intracellular *Mycobacterium tuberculosis* survives in the host by regulating specific host metabolic pathways. In particular, IFN-β is very important for the immune evasion mechanism of tuberculosis. IFN-β is an important cytokine for protecting individuals from many pathogens, including viruses, bacteria, and protozoa, and plays an essential role in the induction of innate and acquired immune responses. In contrast to the protective role of IFN-β in the antiviral immune response, *Mycobacterium tuberculosis* utilizes IFN-β to increase survival in the host. Recent studies have shown that IFN-β increases antimicrobial activity, which correlates with enhanced anti-inflammatory properties. IFN-β is an antagonist of IL-1β and IL-18 because it increases the expression of IL-10 and interferes with the assembly of the NLRP3 inflammasome. *Mycobacterium tuberculosis* secretes chromosomal DNA and is recognized by cyclic GMP-AMP synthase (cGAS, DNA sensor) to induce an IFN-β response.

Cytoplasmic DNA of *Mycobacterium tuberculosis* induces the cGAS-STING-TBK1-IFN-β pathway to inhibit the activation of the NLRP3 inflammasome, which contributes to host antimicrobial activity. Further, *Mycobacterium tuberculosis* inhibits ROS function by catalase peroxidase including several antigens such as CatG, TrxB2, ESAT-6 and CFP-10. More specifically, reactive oxygen species are potent antimicrobial elements in the immune response. In the cytoplasm, reactive oxygen species are produced by NADPH oxidase (NOX2), which consists of several cofactors including gp91phox, p22phox, p47phox, p67phox, and Rac1. gp91phox and gp22phox are located in the phagosome membrane, and p47phox, p67phox, and Rac1 are gathered in gp91. The activated complex generates reactive oxygen species through a redox reaction. In *Mycobacterium tuberculosis* infection, NADPH oxidase significantly increases the production of reactive oxygen species, resulting in bactericidal activity to control the number of bacteria in the cell and induce apoptosis. To survive in the host, *Mycobacterium tuberculosis* blocks NOX2 activity in various ways.

Meanwhile, hexokinases (HKs) phosphorylate glucose into glucose 6-phosphate (G6P) in glycolysis. HK2, one of the hexokinases, is an essential enzyme for glycolysis and regulates mTORC1, a major regulator of autophagy according to cell growth and nutritional status. Furthermore, HK2 is the main component of cancer metabolism, called the "Warburg effect." Active tumors regulate glycolytic metabolism for survival to increase the expression of HK2. Cytoplasmic HK2 binds to VDAC, an external mitochondrial membrane protein and enhance glycolysis and biosynthetic metabolic pathways to increase tumor proliferation. Targeting the interaction of mitochondria with HK2 is a potential strategy for anticancer therapy. In tuberculosis, glycolysis is increased through the expression of glycolytic enzymes, including HK2. In general, this increase is associated with inflammatory activation of the host defense mechanism in response to the bacteria. In fact, *Mycobacterium tuberculosis* utilizes host metabolism through glycolysis and lipid metabolism for host survival and proliferation. However, the exact role of HK2 in tuberculosis is unclear.

SUMMARY

The technical problem to be solved by the present disclosure is to provide a recombinant MPT protein including regions of MPT63 and MPT64 that react with TBK1, p47phox, or HK2, and to provide it for the prevention or treatment of *Mycobacterium tuberculosis* infectious diseases.

Further, the recombinant MPT protein may be administered in combination with BCG to improve the vaccine effect, and thus the present disclosure is to provide the recombinant MPT protein as a tuberculosis vaccine composition and a vaccine adjuvant composition.

However, the technical problem to be solved by the present disclosure is not limited to the above-mentioned problems, and other problems not mentioned are clearly understood by those skilled in the art from the following description.

In order to solve the above problems, the present disclosure provides a recombinant MPT protein including an N-terminal region of MPT63 involved in binding to TBK1, a C-terminal region of MPT63 involved in binding to p47phox, an N-terminal region of MPT64 involved in binding to TBK1, and a C-terminal region of MPT64 involved in binding to HK2.

Further, the present disclosure provides a pharmaceutical composition for preventing or treating *Mycobacterium tuberculosis* infection disease including the recombinant MPT protein as an active ingredient.

Further, the present disclosure provides a method for preventing or treating *Mycobacterium tuberculosis* infectious disease including administering the recombinant MPT protein to an individual.

Further, the present disclosure provides the use of the recombinant MPT protein for the manufacture of a medicament for the prevention or treatment of *Mycobacterium tuberculosis* infectious disease.

Further, the present disclosure provides a composition for a tuberculosis vaccine including the recombinant MPT protein as an active ingredient.

Further, the present disclosure provides a tuberculosis vaccine adjuvant composition including the recombinant MPT protein as an active ingredient.

As one embodiment of the present disclosure, the N-terminal region of MPT63 involved in binding to TBK1 may comprise or consist of the amino acid sequence represented by SEQ ID NO: 6, and in particular, may comprise or consist of the amino acid sequence represented by SEQ ID NO: 1.

As another embodiment of the present disclosure, the C-terminal region of MPT63 involved in binding to p47phox may comprise or consist of the amino acid sequence represented by SEQ ID NO: 7, and in particular, may comprise or consist of the amino acid sequence represented by SEQ ID NO: 2.

As still another embodiment of the present disclosure, the N-terminal region of MPT64 involved in binding to TBK1 may comprise or consist of the amino acid sequence represented by SEQ ID NO: 3 and/or SEQ ID NO: 4.

As still another embodiment of the present disclosure, the C-terminal region of MPT64 involved in binding to HK2 may comprise or consist of the amino acid sequence represented by SEQ ID NO: 5.

As still another embodiment of the present disclosure, the recombinant MPT protein may include each region in the order of a region involved in binding to HK2, a region involved in binding to p47phox, and a region involved in binding to TBK1.

As still another embodiment of the present disclosure, the recombinant MPT protein may target macrophages infected with *Mycobacterium tuberculosis*, increase the expression level of TNF-α and IL-6 in macrophages, decrease secretion of IFN-β in macrophages, and increase the level of cytoplasmic reactive oxygen species (ROS) in macrophages.

The present disclosure is the first to identify a host cell protein and its function with which MPT63 and MPT64, secreted antigens of *Mycobacterium tuberculosis*, interact, and to construct a recombinant MPT protein including each domain of MPT63 and MPT64 interacting with the host cell protein, and the recombinant MPT protein may be applied to a use for the prevention and treatment of tuberculosis by confirming that the recombinant MPT protein targets the *Mycobacterium tuberculosis*-infected macrophages and increases the ROS level and inflammatory cytokine expression in macrophages, thereby inducing the death of *Mycobacterium tuberculosis*. The recombinant MPT protein of the present disclosure has no cytotoxicity and has no side effects by targeting *Mycobacterium tuberculosis*-infected macrophages, and the recombinant MPT protein of the present disclosure can improve the vaccine effect by the BCG vaccine so that it can be used as a tuberculosis vaccine and/or vaccine adjuvant either alone or together with known tuberculosis vaccines.

BRIEF DESCRIPTION OF THE DRAWINGS

These and/or other aspects, features, and advantages of the disclosure will become apparent and more readily appreciated from the following description of example embodiments, taken in conjunction with the accompanying drawings of which:

FIGS. 2A-2D shows the results of screening rMPT63 and rMPT64 production and proteins interacting therewith. Specifically, FIG. 2A is the result of analyzing the vector construct for rMPT63 preparation and purified rMPT63 by Western blot using Coomassie Blue staining and anti-His antibody, FIG. 2B is the result of analyzing the vector construct for rMPT64 preparation and purified rMPT64 by Western blot using Coomassie Blue staining and anti-His antibody, and FIGS. 2C and 2D are the results of analyzing the rMPT63 and rMPT64-interacting peptides using mass spectrometry (MS);

FIG. 5A is a structural schematic diagram of rMPT63, TBK1 and p47phox, FIGS. 5B and 5C are the results of GST pulldown and Western blotting after 293T cells are transfected with GST, GST-TBK1, or GST-p47phox together with Myc or Myc-MPT63 and truncated mutant constructs, FIG. 5D is a structural schematic diagram of rMPT64, TBK1 and HK2, and FIGS. 5E and 5F are the results of GST pulldown and Western blotting after 293T cells are transfected with GST, GST-TBK1, or GST-HK2 together with Myc or Myc-MPT64 and truncated mutant constructs;

FIG. 6A is a structure of a TBK1 peptide including a region of MPT63 and/or MPT64 that binds to TBK1;

FIG. 9A is a schematic diagram of the designed recombinant MPT protein structure;

DETAILED DESCRIPTION

Figure 1A:
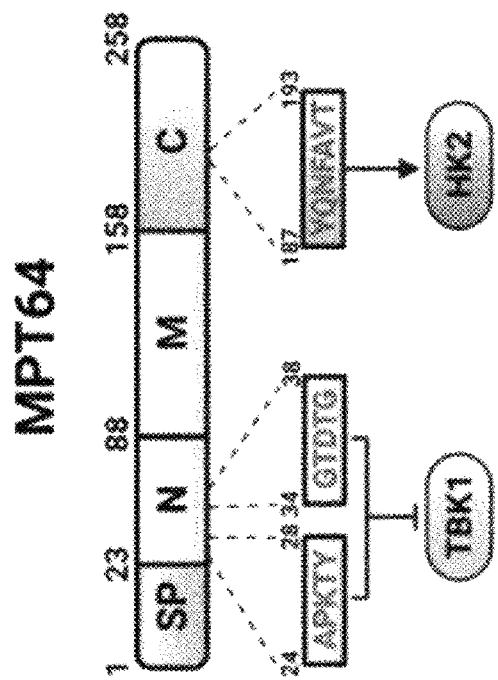
FIG. 1A is a schematic diagram illustrating the results of screening domains of regions that interact with TBK1, p47phox or HK2 in MPT63 and MPT64, respectively.
Figure 1A:
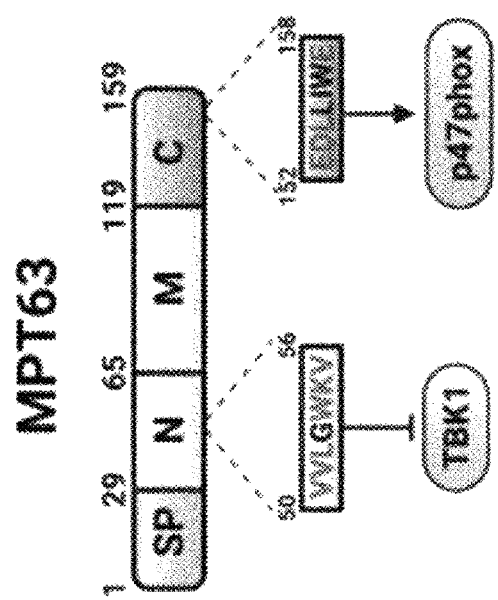
Figure 1B:
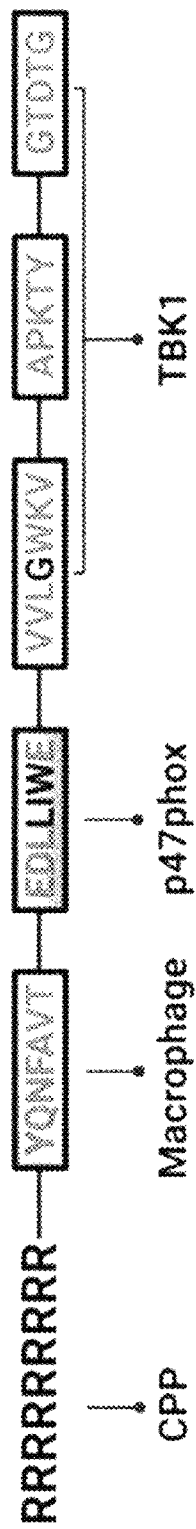
FIG. 1B is a schematic diagram illustrating the structure of a recombinant MPT protein (rMPT) in which a domain that interacts with TBK1, p47phox or HK2 in MPT63 and MPT64 are combined.
Figure 1C:
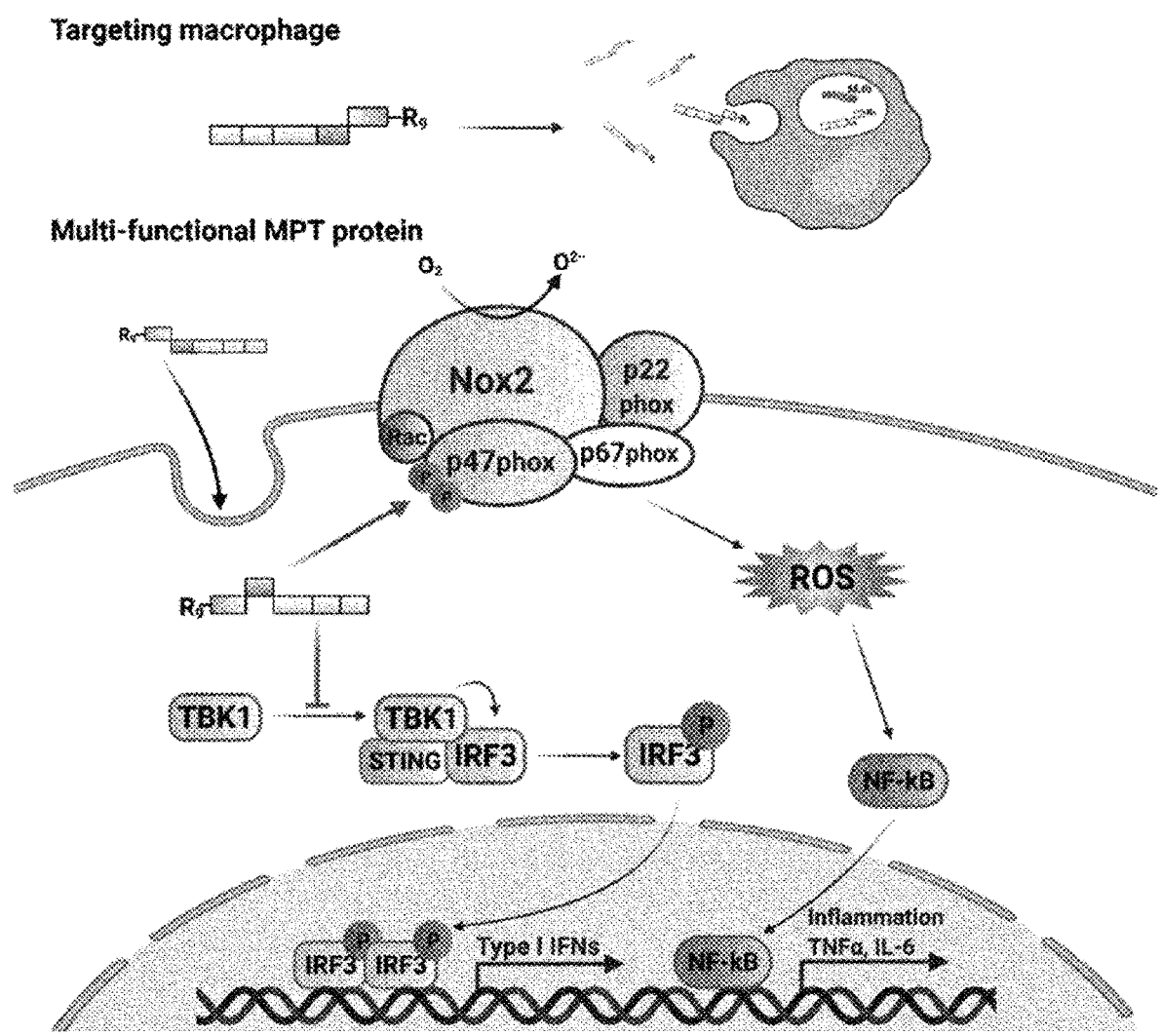
FIG. 1C is a schematic diagram illustrating the regulation of the host metabolic pathway of rMPT in macrophages.

The present inventors confirmed the close correlation between MPT63's interaction with TBK1 and p47phox and MPT64's TBK1 and HK2, developing a vaccine and a tuberculosis treatment that targets *Mycobacterium tuberculosis*-infected macrophages based on MPT63 and MPT64 and regulates expression of IFN-β and production of hyperactive oxygen species (ROS) in the macrophages.

It was confirmed that TBK1 peptide may reduce the production of IFN-β and the number of bacteria through inhibition of the STING1-TBK1-IRF3 pathway in macrophages infected with *Mycobacterium tuberculosis*, p47 peptide may enhance the complex composition of p47phox-p22phox-p67phox to increase the level of reactive oxygen species in macrophages and induce the death of *Mycobacterium tuberculosis*, and HK2 peptide may be used for targeting macrophages infected with *Mycobacterium tuberculosis*. Therefore, the present inventors designed and constructed a multifunctional recombinant MPT (rMPT) based on MPT63 and MPT64 containing TBK1, p47 and HK2 peptides (FIG. 1), observed that the constructed rMPT regulated levels of IFN-β and reactive oxygen species in macrophages infected with *Mycobacterium tuberculosis* to reduce the number of tuberculosis and confirmed the antibacterial activity of the rMPT. Further, the present inventors confirmed that the vaccine effect was more excellent in mice co-administered with BCG and rMPT.

Specifically, to identify the binding partner of MPT63 in macrophages, the present inventors constructed recombinant MPT63 (rMPT63) and performed co-immunoprecipitation with lysates of macrophages so as to confirm that rMPT63 interacts with TBK1 and p47phox in macrophages (See Result 1-1).

Further, the present inventors transformed each domain of GST-MPT63 and Flag-TBK1 or V5-p47phox into 293T cells and performed GST pulldown analysis to identify the region of MPT63 involved in binding to TBK1 and p47phox. As a result, it is confirmed that the region involved in binding to TBK1 is located at the N-terminus of MPT63 and in particular, amino residues at positions 50-56 except for G53 are essential for binding to TBK1. In addition, it is confirmed that the region involved in binding to p47phox is located at the C-terminus of MPT63 and amino residues E152, D153, L154, and E158 are essential for binding to p47phox (See Result 1-2).

Next, to identify the binding partner of MPT64 in macrophages, the present inventors constructed recombinant MPT64 (rMPT64) and performed co-immunoprecipitation with lysates of macrophages to confirm that rMPT64 interacts with TBK1 and HK2 in macrophages (See Result 2-1).

Further, the present inventors transformed each domain of GST-MPT64 and Flag-TBK1 or Flag-HK2 into 293T cells and performed GST pulldown analysis to identify the region of MPT64 involved in binding to TBK1 and HK2. As a result, it is confirmed that the region involved in binding to TBK1 is located at the N-terminus of MPT64 and in particular, amino residues at positions 24-28 and 34-38 are essential for binding to TBK1. In addition, it is confirmed that the region involved in binding to HK2 is located at the C-terminus of MPT64 and amino residues at positions 187-193 are essential for binding to HK2 (See Result 2-2).

Table 1 below shows the amino acid sequences of MPT63 and MPT64 domains that act in binding to the binding partners interacting in the host cell.

TABLE 1

| Derivation | Binding partner | Amino acid sequence of the binding domain | SEQ ID NO |
|---|---|---|---|
| MPT63 | TBK1 | VVLGWKV | 1 |
|  | P47phox | EDLLIWE | 2 |
| MPT64 | TBK1 | APKTY | 3 |
|  |  | GTDTG | 4 |
|  | HK2 | YQNFAVT | 5 |

The underlined amino acid residues in Table 1 are not essential for binding, and may be substituted or mutated within a range in which the function of each domain is maintained.

Next, the present inventors confirmed the function that MPT63 and MPT64 perform by binding to TBK1 in the host cell. TBK1 forms a complex with an essential component of the STING-TBK1-IRF3 pathway and induces the expression of IFN-β. A TBK1 peptide containing a region identified as a TBK1-binding domain in MPT63 and MPT64 was constructed (FIG. 3A) and *Mycobacterium tuberculosis*-infected THP-1 cells were treated with the constructed TBK1 peptide. As a result, it was confirmed that MPT63/64-TBK1 peptide acts with TBK1 to reduce the formation of STING1-TBK1-IRF3 complex and the secretion of IFN-β. Further, it was confirmed that the MPT63/64-TBK1 peptide decreased the viability of *Mycobacterium tuberculosis* by increasing the expression of TNF-α and IL-6 along with a decrease in IFN-β secretion (See Result 3).

In addition, the present inventors confirmed the function that MPT63 performs by interacting with p47phox in the host cell. P47phox forms a complex with p22phox and p67phox to activate NADPH and induce intracellular ROS production. A p47 peptide containing a region identified as a P47phox-binding domain in MPT63 was constructed (FIG. 4A) and *Mycobacterium tuberculosis*-infected THP-1 and BMDM cells were treated with the constructed p47 peptide. As a result, it was confirmed that the p47 peptide increased the formation of the p47phox-p22phox-p67phox complex and improved the stability of p47phox, promoting ROS generation in cells. In addition, it was confirmed that the p47 peptide not only promotes ROS production but also increases the expression of TNF-α and IL-6 in *Mycobacterium tuberculosis*-infected macrophages, thereby reducing the viability of *Mycobacterium tuberculosis* (See Result 4).

Figure 5A:
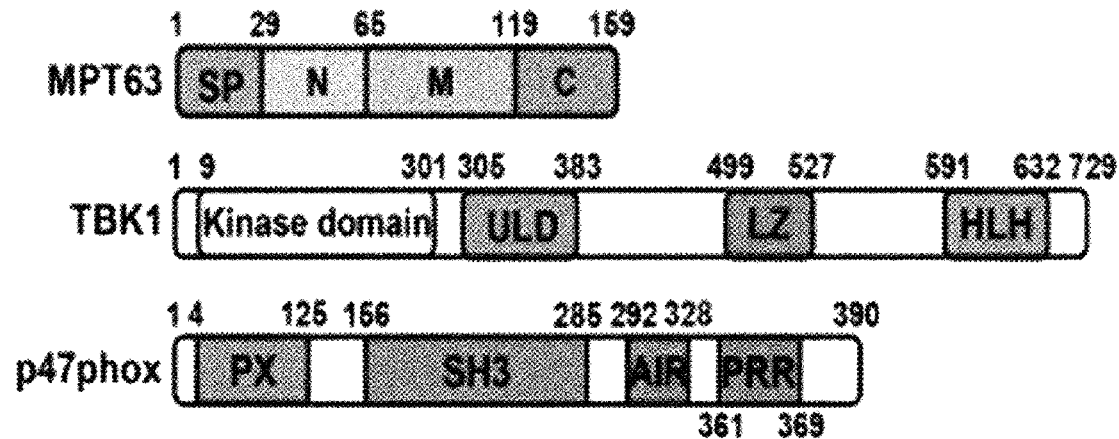
FIGS. 5A-5F is a diagram for confirming the host proteins interacting with rMPT63 and rMPT64.
Figure 5B:
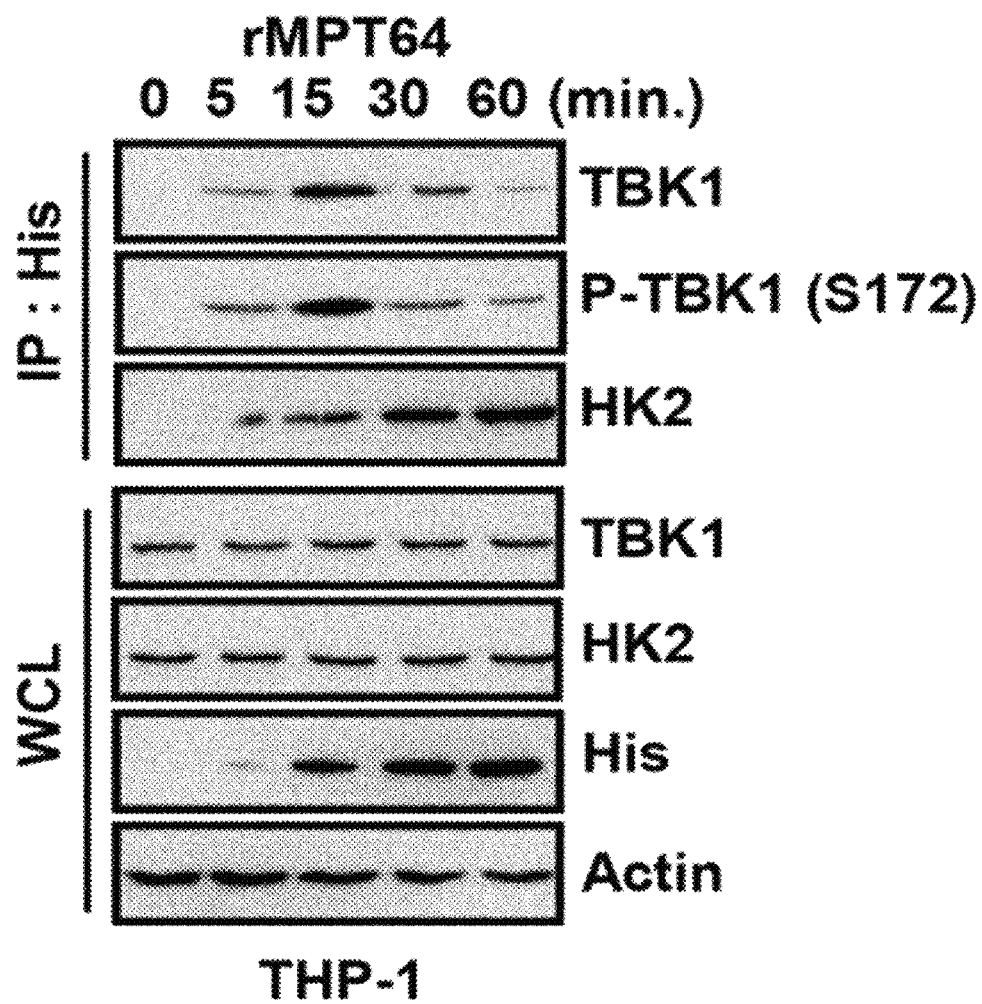
Figure 5C:
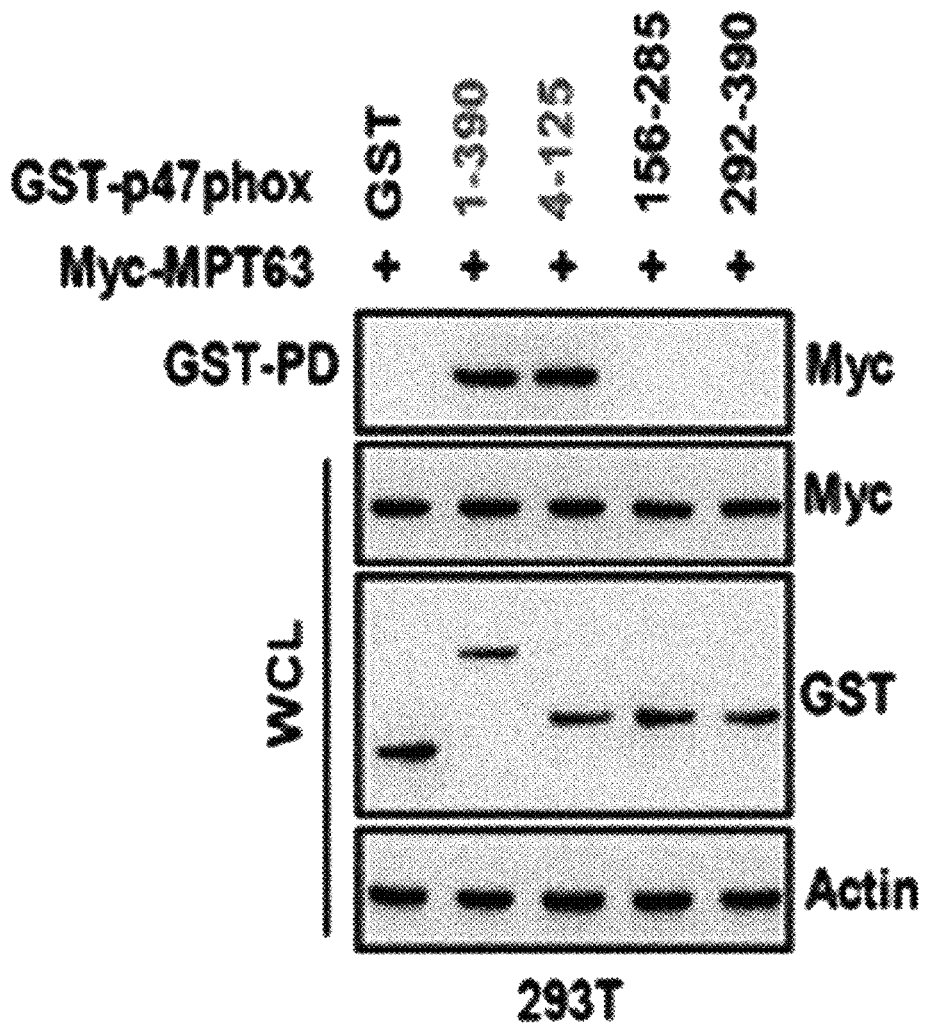

Further, the present inventors confirmed the function that MPT63 performs by interacting with HK2 in the host cell. It is known that HK2 is an enzyme that converts glucose into glucose-6 phosphate and accumulates in an inflammatory environment to activate the immune response. An HK2 peptide containing a region identified as a domain in MPT64 that interacts with HK2 was constructed (FIG. 5A) and treated in macrophages to confirm HK2-specific binding of the HK2 peptide. In addition, as a result of treating the macrophages infected with *Mycobacterium tuberculosis* with HK2 peptide, it was confirmed that the HK2 peptide did not significantly affect the expression of inflammatory cytokines and the viability of *Mycobacterium tuberculosis*. However, as a result of intranasal administration of HK2 peptide to *Mycobacterium tuberculosis*-infected mice, it was confirmed that it may be used for targeting *Mycobacterium tuberculosis*-infected macrophages by binding specifically to *Mycobacterium tuberculosis*-infected macrophages in the lungs (See Result 5).

Based on the above results, the present inventors designed and constructed a multifunctional recombinant MPT protein (rMPT) including each domain of MPT63 and/or MPT64 interacting with TBK1, p47phox, or HK2. It was confirmed that the constructed rMPT has very low or no cytotoxicity and interacts with TBK1, p47phox, and HK2 in macrophages as intended. In macrophages infected with *Mycobacterium tuberculosis*, rMPT decreased the formation of the STING1-TBK1-IRF3 complex and increased the formation of the p47phox-p22phox-p67phox complex. As a result, it was confirmed that according to the rMPT treatment, the secretion of IFN-β of macrophages decreased, the secretion of TNF-α and IL-6 increased, and the death of *Mycobacterium tuberculosis* increased (See Result 6). In addition, the present inventors administered rMPT to mice infected with *Mycobacterium tuberculosis*, confirmed the reduction in CFU and granuloma production, confirmed the prevention and treatment effect of tuberculosis, and confirmed its stability by observing rMPT excretion in the rat liver 6 hours after administration (See Result 8).

The present inventors first confirmed that MPT63 and MPT64 interact with TBK1, p47phox, or HK2 in a host cell. The present inventors confirmed the functions of each interaction and the regions of MPT63 and MPT64 that interact with proteins in the host cell to construct and provide a recombinant protein (rMPT) containing them for the prevention and treatment of tuberculosis.

Accordingly, the present inventors provide recombinant MPT protein including the N-terminal region of MPT63 involved in binding to TBK1, the C-terminal region of MPT63 involved in binding to p47phox, the N-terminal region of MPT64 involved in binding to TBK1 and the C-terminal region of MPT64 involved in binding to HK2.

The amino acid sequence of each region is shown in Table 2 below.

TABLE 2

| Derivation | Binding partner | Amino acid sequence of the binding domain | SEQ ID NO |
|---|---|---|---|
| MPT63 | TBK1 | VVLXWKV | 6 |
|  | P47phox | EDLX$_1$X$_2$X$_3$E | 7 |
| MPT64 | TBK1 | APKTY | 3 |
|  |  | GTDTG | 4 |
|  | HK2 | YQNFAVT | 5 |

The present inventors constructed the recombinant MPT protein through a specific experiment, which had the *Mycobacterium tuberculosis* death-inducing effect and vaccine effect, including each region in the order of a region involved in binding to HK2, a region involved in binding to p47phox, and a region involved in binding to TBK1. However, since the domains of each region perform their functions independently of each other, the arrangement order of the regions is irrelevant.

The recombinant MPT protein of the present disclosure may be provided for the prevention or treatment of tuberculosis.

The recombinant MPT protein of the present disclosure may target macrophages infected with *Mycobacterium tuberculosis*, and increase the expression of inflammatory cytokines and ROS production in the macrophages, thereby inducing the death of *Mycobacterium tuberculosis* so that the present disclosure may provide a pharmaceutical composition for preventing or treating bacterial infectious diseases including the recombinant MPT protein as an active ingredient.

The recombinant MPT protein of the present disclosure may be one in which one or more amino acids constituting the aforementioned protein are substituted, modified, and/or deleted in a range in which the function of each domain is maintained, and such variants may be a mutant having a better effect in inducing apoptosis of *Mycobacterium tuberculosis* than the recombinant MPT protein used in a specific experiment in the present disclosure.

The amino terminus of the recombinant MPT protein of the present disclosure may be bound to a protecting group such as an acetyl group, a fluorenyl methoxy carbonyl group, a formyl group, a palmitoyl group, a myristyl group, a stearyl group, and polyethylene glycol (PEG). The carboxy terminus of the peptide may be modified with a hydroxyl group (—OH), an amino group (—NH$_2$), an azide (—NHNH$_2$), and the like. In addition, the terminus of the peptide or R-group of the amino acid of the present disclosure may include fatty acids, oligosaccharides chains, all nanoparticles (gold particles, liposomes, heparin, hydrogel, etc.), amino acids, carrier proteins, and the like. Modification of the above-described amino acids may improve the potency and stability of the recombinant protein of the present disclosure.

As used herein, the term "stability" refers not only to in vivo stability, but also storage stability (including stability of room temperature storage, cold storage, and frozen storage).

In addition, the present disclosure provides a method for preventing or treating tuberculosis, including administering a recombinant MPT protein and/or a mutant thereof to an individual, wherein tuberculosis may be a disease caused by *Mycobacterium tuberculosis* infection.

In addition, the present disclosure provides a method for preventing tuberculosis by developing acquired immunity against *Mycobacterium tuberculosis*, including administering a recombinant MPT protein and/or a mutant thereof to an individual, in which the prevention method may further comprise administering a BCG (Bacille de Calmette-Guerin) vaccine to an individual, and the administration of the recombinant MPT protein and BCG vaccine may be performed simultaneously and/or sequentially.

In the present disclosure, the term "individual" is not limited as long as it is a mammal but may preferably be a human or livestock.

In the present disclosure, the term "prevention" refers to any action that delays infection of *Mycobacterium tuberculosis* or delays the onset of disease caused by the infection by administration of the pharmaceutical composition according to the present disclosure, and the term "treatment" refers to any action that alleviates and advantageously changes symptoms due to *Mycobacterium tuberculosis* infection by administration of the pharmaceutical composition according to the present disclosure. In addition, in the present disclosure, the term "vaccine" refers to the generation of acquired immunity against *Mycobacterium tuberculosis* by administering the composition according to the present disclosure. As used herein, "prevention" includes the meaning of "vaccine" as comprehensively meaning a delay of *Mycobacterium tuberculosis* infection, etc., but the effect of prevention mentioned together with the therapeutic effect means delay of *Mycobacterium tuberculosis* infection caused by innate immunity.

In the present disclosure, the pharmaceutical composition may further include one or more known antibiotics in addition to the recombinant MPT protein and/or its mutant of the present disclosure and may further include a suitable carrier, an excipient, and a diluent commonly used in the preparation of the pharmaceutical composition.

Meanwhile, the present inventors confirmed that the strength of the immune response activity according to restimulation was improved in mice administered with the BCG vaccine and the rMPT compared to the group administered with BCG alone (See Result 7). The recombinant MPT protein of the present disclosure may be provided as a composition for tuberculosis vaccine and as a composition for adjuvant tuberculosis vaccine.

The vaccine composition of the present disclosure may further include a pharmaceutically acceptable carrier, an appropriate adjuvant, and other conventional substances, and may be administered in an immunologically effective amount. In the present disclosure, the term "immunologically effective amount" refers to an amount sufficient to exhibit an immune enhancing effect and an amount sufficient to not cause side effects or serious or excessive immune response, and the exact concentration varies depending on the individual to be administered. In order to test the development of an immune response, one of ordinary skill in the art may determine the concentration using known methods. In addition, it may change depending on the dosage form and route, the age, health and weight of the recipient, the nature and severity of symptoms, the type of current treatment, and the number of treatments.

In the present disclosure, the term "carrier" is also called a vehicle and refers to a compound that facilitates the addition of proteins or peptides into cells or tissues. For example, dimethyl sulfoxide (DMSO) is a commonly used carrier that facilitates the introduction of many organic substances into cells or tissues of living organisms.

In the present disclosure, the term "diluent" is defined as a compound that is diluted in water that not only stabilizes the biologically active form of the target protein or peptide but also dissolves the protein or peptide. Salts dissolved in buffer solutions are used as diluents in the art. A commonly used buffer solution is phosphate-buffered saline because it mimics the salt state of human solutions. Because buffer salts may control the pH of a solution at low concentrations, buffer diluents rarely modify the biological activity of a compound. As used herein, the compounds containing azelaic acid may be administered to a human patient as such or as a pharmaceutical composition admixed with other ingredients as in combination therapy or with suitable carriers or excipients.

Further, the pharmaceutical composition for the prevention or treatment of *Mycobacterium tuberculosis* infectious disease including the recombinant MPT protein and/or its mutant according to the present disclosure as an active ingredient may be formulated and used in the form of external preparations such as powders, granules, tablets, capsules, suspensions, emulsions, syrups, aerosols, and sterile injection solutions according to a conventional method, respectively. The pharmaceutical composition of the present disclosure is administered orally or parenterally (e.g., nasally, intravenously, subcutaneously, intraperitoneally or topically applying) according to the desired method. The dosage may vary depending on the condition and weight of the patient, the degree of disease, the drug form, the route and duration of administration, but may be appropriately selected by those skilled in the art. For example, about 0.001 mg to 1000 mg may be administered in a mixed form with a pharmaceutically acceptable carrier. The pharmaceutical composition of the present disclosure may be administered once to several times a day as necessary and may be used alone or in combination with methods using surgery, hormone therapy, drug therapy, and biological response modifiers.

Further, the recombinant MPT protein and/or a mutant thereof of the present disclosure may provide a quasi-drug composition for the purpose of preventing or improving *Mycobacterium tuberculosis* infectious disease, and the quasi-drug composition of the present disclosure may be used together with other quasi-drugs or quasi-drug components and may be appropriately used according to a conventional method.

Further, the present disclosure provides a food composition or feed composition including a recombinant MPT protein and/or a mutant thereof as an active ingredient. When the recombinant MPT protein and/or mutant thereof of the present disclosure is used as an additive to food or feed, the recombinant MPT protein and/or mutant thereof may be added as it is or used with other food, feed, or components thereof and may be appropriately used according to a conventional method. The mixed amount of the active ingredient may be suitably determined according to the purpose of use (prevention of infectious diseases through inhibition of proliferation and growth of bacteria, health or therapeutic treatment). In general, in the production of feed, food or beverage, the recombinant MPT protein of the present disclosure and/or a mutant thereof is added in an amount of 15 wt % or less, preferably 10 wt % or less, based on the raw material. However, in the case of long-term intake for health and hygiene or health control, the amount may be less than the above range. Since there is no problem in terms of safety, the active ingredient may be used above the aforementioned range. There is no particular limitation on the type of the food and feed.

In the present disclosure, the amino acid sequence is abbreviated as follows according to the IUPAC-IUB nomenclature:

arginine (Arg, R), lysine (Lys, K), histidine (His, H), serine (Ser, S), threonine (Thr, T), glutamine (Gln, Q), asparagine (Asp, N), methionine (Met, M), leucine (Leu, L), isoleucine (Ile, I), valine (Val, V), phenylalanine (Phe, F), tryptophan (Trp, W), tyrosine (Tyr, Y), alanine (Ala, A), glycine (Gly, G), proline (Pro, P), cysteine (Cys, C), aspartic Acid (Asp, D), glutamic acid (Glu, E), and norleucine (Nle).

The present disclosure, unless otherwise defined, may be carried out by conventional techniques commonly used in the field of molecular biology, microbiology, protein engineering and recombinant DNA within the ability of those skilled in the art. Techniques for practicing the present disclosure are known to those skilled in the art and are described in many standardized textbooks and reference books.

Further, unless otherwise defined herein, all technical and scientific terms used herein have the same meaning as commonly understood by those skilled in the art to which this disclosure belongs. Various scientific dictionaries containing terms contained herein are well known and available in the art. The terminology described herein may be used in various ways depending on the context in which it is used by those skilled in the art and should not be construed as limiting the present disclosure to specific methodologies, protocols, and reagents.

The present disclosure may apply various transformations and may have various embodiments. Hereinafter, specific embodiments are illustrated in the drawings and described in detail in the detailed description. However, it should be understood that this is not intended to limit the present disclosure to specific embodiments and includes all modifications, equivalents and substitutes included in the spirit and scope of the present disclosure. In describing the present disclosure, if it is determined that a detailed description of a related known technology may obscure the gist of the present disclosure, the detailed description thereof is excluded.

[Test Method and Materials]

1. Mice and Cell Culture

Wild-type C57BL/6 mice were purchased from Samtaco Bio Korea (Gyeonggi-do, Korea). $TBK1^{-/-}$ and $p47phox^{-/-}$ mice were provided by Dr. Cheol-Ho Lee (Animal Resource center of Korea Research Institute of Bioscience and Biotechnology, Daejeon, Korea). LysMCre mice (B6.129P2-Lyz2tml(cre)Ifo/J) were purchased from Jackson Laboratories, and HK2-floxed mice (C57BL/6 bakground) were provided by Dr. Nissim Hay (University of Illinois, Chicago). As described above, cre-mediated recombination was confirmed by using the genomic DNA of isolated peritoneal macrophages for PCR, and next to the flox region was used as the primer. The absence of HK2 expression in the macrophages was confirmed by immunoblotting analysis using an HK2-specific antibody (Santa Cruz, B-8, Dallas, TX, US). All mice were raised in specific pathogen-free facility based on the standard Human Animal Bilateral Treaty (SPF) approved by "Regulation" of the Institutional Animal Care and Use Committee of Hanyang University (Protocol 2020-0060) and the Institute of Ethics of the Institute of Microbiology Science of the Chinese Academy of Sciences (IMCAS) (SQIMCAS2019003 allowed).

Primary bone marrow-derived macrophages (BMDM) were isolated from C57BL/6 mice as described above and cultured in DMEM medium with M-CSF (R&D Systems, 416-ML) for 3 to 5 days. HEK293T (ATCC-11268; American Type Culture Collection) or THP-1 (ATCC-TIB-202) cells were cultured in DMEM or RPMI1640 (Gibco) containing 10% FBS (Gibco), sodium pyruvate, and non-essential amino acids (Gibco). Human THP-1 (ATCC TIB-202) cells were cultured in RPMI 1640/Glutamax supplemented with 10% FBS and treated with 20 nM PMA (Sigma-Aldrich) for 24 hours to induce differentiation into macrophages. They were washed three times with PBS. Transient transfections were performed using calcium phosphate (Clontech) on the 293T according to the manufacturer's instructions. The THP-1 cell line was transfected with Lipofectamine 3000 (Invitrogen), followed by a standard selection technique using 400 to 800 μg/ml of G418.

2. Strains

*E. coli* DH5a and BL21 were cultured in flasks using LB medium for genetic manipulation or protein overexpression. *M. bovis* BCG and *Mycobacterium tuberculosis* strain H37Rv (provided by Dr. Tucson, R. L. Friedman, University of Arizona) were cultured. In this experiment, the effective concentration of lipopolysaccharide was 50 μg/ml, and the bacteria-to-cell ratio was 10:1. For all tests, midlog phase bacteria (absorption 0.4) were used. Each strain was divided into 1 ml and stored at −70° C.

3. Recombinant Protein

In order to construct the MPT63/64 recombinant protein derived from the MTB H37Rv strain (GenBank accession numbers NP_216442 and NP_216496), MPT63 amino acids (50-56, 152-158), MPT64 amino acids (24-28, 34-38, 187-193) and R9 seq was cloned into the pRSFDuet-1 vector (Novagen) using an N-terminal 6×His tag, and the vector was transfected into *E. coli* BL21(DE3) pLysS according to the standard protocol recommended by Novagen, followed by induction of induction, harvest and purification. The obtained rMPT was dialyzed against a permeable cellulose membrane and tested for lipopolysaccharide contamination by Limulus amebocyte lysate assay (BioWhittaker), and it was confirmed that the content of rMPT protein used in the experiment was lower than 20 µg/ml.

4. Protein Purification and Mass Spectrometry

To identify GRA9 binding proteins, THP-1 cells expressing Flag-GRA9 or vector were harvested, and they were dissolved with NP-40 buffer (50 mM HEPES, pH 7.4, 150 mM NaCl, 1 mM EDTA, 1% (v/v) NP40). The buffer was supplemented with a protease inhibitor cocktail (Roche, Basel, Switzerland). After centrifugation, the supernatant was reacted with protein A/G beads at 4° C. for 2 hours to provide impurities. The lysate from which impurities were removed was mixed with the αFlag antibody bound to agarose beads at 4° C. for 4 hours. The precipitate was washed with a lysis buffer, and the protein bound to the beads was eluted and separated by Nupage 4% to 12% Bis-Tris gradient gel (Invitrogen). After silver staining (Invitrogen), specific protein bands were excised and analyzed by ion trap mass spectrometry at the Korea Institute of Basic Sciences (Seoul, Korea) mass spectrometry facility, and amino acid sequences were determined through tandem mass spectrometry and database search.

5. Antibody

Flag (D-8), GST (B-14), V5 (E10), p22phox (FL-195), gp91phox (H-60), p47phox (H-195), p67phox (H-300), HK1 (G-1), HK2 (B-8), HK3 (A-9) and Actin (I-19) were purchased from Santa Cruz Biotechnology (Dallas, Texas, USA). Specific antibodies to phospho-p47phox (S304, ABIN1526728), (S345, ABIN482777), (S359, ABIN482335) and (S370, ABIN1989372) were purchased from St John's Laboratory. Antibodies against IRF3 (ab68481), His (ab18184), Myc (ab9106) and AU1 (ab3401) were purchased from Abcam (Cambridge, UK). Antibodies to TBK1 (E8I3G) and phospho-TBK1 (S172) (D52C2) were purchased from Cell Signaling Technology (Danvers, MA, USA), and STING1 (NBP2-24683) was purchased from Novus Biologicals (Centennial, CO, USA).

6. Plasmid Construct

Plasmids encoding full-length MPT63 (NR-15618) and MPT64 (NR-13273) were provided from BEI Resources, and TBK1 (87443) and HK2 (25529) were purchased from Addgene (Watertown, MA, US69). p47phox has been previously described. Plasmids encoding different regions of MPT63, MPT64, TBK1, p47phox, and HK2 were generated by PCR amplification from total cDNA, and sub-cleaved from pEBG plasmid containing an N-terminal GST epitope tag between BamHI and NotI. All constructs for stable expression in mammalian cells were derived from the pEBG-GST mammalian fusion vector and the pEF-IRES-Puro expression vector. All constructs were verified to be 100% identical to the original sequence using ABI PRISM 377 automated DNA sequence.

7. GST Pulldown, Immunoprecipitation (Immunoblot), and Western Blot (Immunoprecipitation)

For GST pulldown, cells were harvested and lysed with NP-40 buffer supplemented with protease inhibitor cocktail (Roche). After centrifugation, the supernatant was pre-removed with protein A/G beads at 4° C. for 2 hours. The removed lysate was mixed with a 50% slurry of glutathione-conjugated Sepharose beads (Amersham Biosciences), and was incubated at 4° C. for 4 hours for the binding reaction. The precipitate was washed with lysis buffer. Proteins bound to glutathione beads were boiled for 5 minutes and eluted with SDS loading buffer.

For immunoprecipitation, cells were harvested and then lysed in NP-40 buffer supplemented with protease inhibitor cocktail (Roche). Impurities were removed with protein A/G agarose beads at 4° C. for 1 hour, and whole cell lysates were used for immunoprecipitation with the indicated antibodies. In general, 1 to 4 µg of commercial antibody was added to 1 ml of cell lysate, and they were incubated at 4° C. for 8 to 12 hours. After protein A/G agarose beads were added for 6 hours, the immune precipitates were washed with lysis buffer and then boiled for 5 minutes and eluted with SDS loading buffer.

For western blotting, polypeptides were separated by SDS-polyacrylamide gel electrophoresis (PAGE) and transferred to PVDF membrane (Bio-Rad). Antibody binding was visualized with chemiluminescence (ECL; Millipore) and detected with a Vilber chemiluminescence analyzer (Fusion SL 3; Vilber Lourmat).

8. Analysis of the Interaction Kinetics of MPT63 and MPT64 with their Binding Partners The interaction of MPT63-TBK1 with p47phox and the interaction of MPT64-TBK1 with HK2 were monitored using a Fluoromax-4 spectrofluorometer (HORIBA Scientific) which was performed as previously described (Guo et al., 2005). MPT63 and MPT64, respectively, were labeled with BODIPY FL Iodoacetamide (ThermoFisher Scientific) according to the manufacturer's instructions. The labeled MPT63 or MPT64 was excited at 350 nm and detected through a cutoff filter at 512 nm. The fluorescently labeled MPT63 or MPT64 was titrated with unlabeled TBK1, p47phox or HK2 for kinetic analysis. The excitation and emission wavelengths were 498 mm and 518 nm, respectively. The obtained data were verified using the Grafit program, and all fluorescence measurements were performed at 25° C. in 30 mM Tris, pH 7.4, 150 mM NaCl and 1 mM dithiothryitol.

9. Enzyme-Linked Immunosorbent Assay (ELISA)

For the detection of TNF-α, IL-6, IL-2, and IFN-α, cell culture supernatants and mice blood (sera) were analyzed using the BD OptEIA ELISA set (BD Parmingen). All experiments were performed according to the manufacturer's recommendations.

10. HK2 Knockout Cell Construction

The HK2 KO THP-1 cell population was generated by gene editing of CRISPR/Cas9 using the HK2 Human Gene Knockout Kit (CRISPR) (KN209482) from Origin Technologies (Rockville, MD, USA). HK2 KO cells were selected by puromycin. All experiments were performed according to the manufacturer's recommendations.

11. *Mycobacterium tuberculosis* Infection In Vitro and In Vivo

For in vitro experiments, cells were infected with *Mycobacterium tuberculosis* for 2 to 4 hours. Then, cells were washed with PBS to remove extracellular bacteria, supplied with fresh medium, and cultured at 37° C. for the indicated time. For in vivo experiments, female SPF C57BL/6 mice were maintained at 6 to 8 weeks of age during the course of the experiment, and age and sex were matched in each experiment. No further randomization was used to allocate experimental groups. *Mycobacterium tuberculosis* ($1 \times 10^4$ CFU/mouse) was injected into mice. Mice were sacrificed 5 hours later, and the lungs, spleen, and liver were identified. Mice were used in a biosafety level 3 laboratory facility, and all animal studies were approved by the Biomedical Research Ethics Committee of the Institute of Microbiology (Beijing Academy of Sciences, China).

12. Peptide

MPT peptide bound to R9 was synthesized commercially by Peptron (Korea) to avoid abnormal reactions in cells and purified in the form of an acetate salt. The endotoxin content measured by the Limulus amebocyte lysate test (BioWhittaker) was less than 3 to 5 µg/ml at the peptide concentration used in the experiment.

13. Histological Analysis

For immunohistochemical staining of tissue sections, mice lungs were fixed in 10% formalin and encased in paraffin. Paraffin was cut to a thickness of 4 µm and stained with hematoxylin and eosin (H&E). Histopathological scores were set based on the number and distribution of inflammatory cells and the severity of inflammation in the tissue. Each organ section was scored independently by a pathologist without prior knowledge of the treatment group, and a histological score ranging from 0 to 4 was assigned to each specimen.

14. In Vivo Imaging

Streptavidin-conjugated Cy5.5 dye was added to rMPT to prepare rMPT/Cy5.5. rMPT/Cy5.5 was administered to mice via the nasal cavity of mice infected with *Mycobacterium tuberculosis*. To study tissue biodistribution, mice were sacrificed at different time points after administration, and major organs were excised and imaged using an IVIS Spectrum-CT in vivo imaging system (PerkinElmer, Inc.).

15. Statistical Analysis

All data were analyzed using Student's t-test with Bonferroni adjustment for multiple comparisons, which were expressed as mean±SD. Statistical analyzes were performed using the SPSS (version 12.0) statistical software program (SPSS, Chicago, IL, USA). Differences were considered significant at p<0.05 (*P<0.05, P<0.01; *P<0.001). GraphPad Prism (version 5.0, CA, USA) was used for survival clean-up, and data were graphed and analyzed by the Kaplan and Meier product restriction method using the log-rank (Mantele-Cox) test for comparison.

[Experiment Result]

Figure 2A:
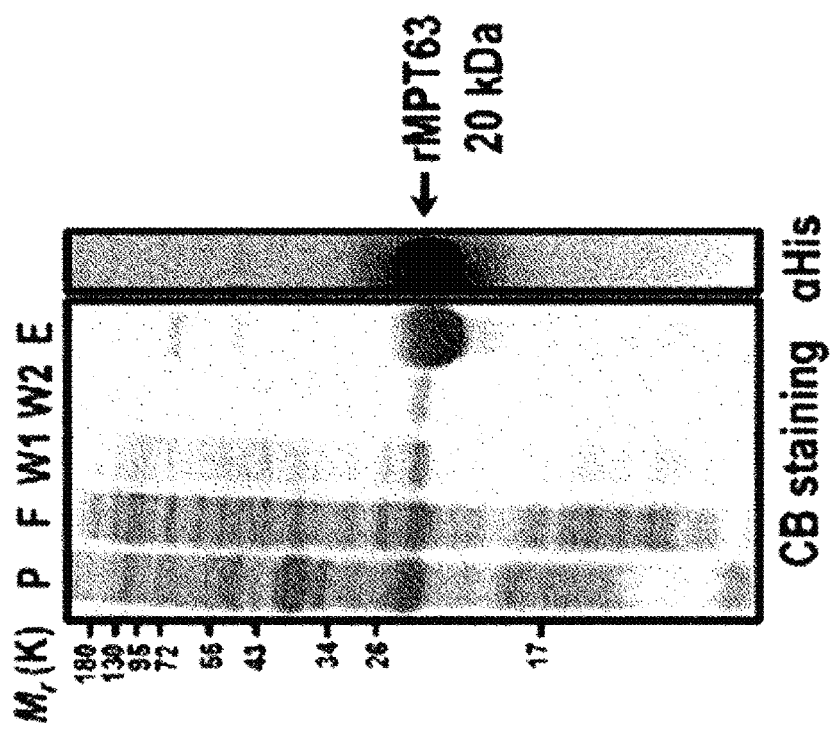
Figure 2A:
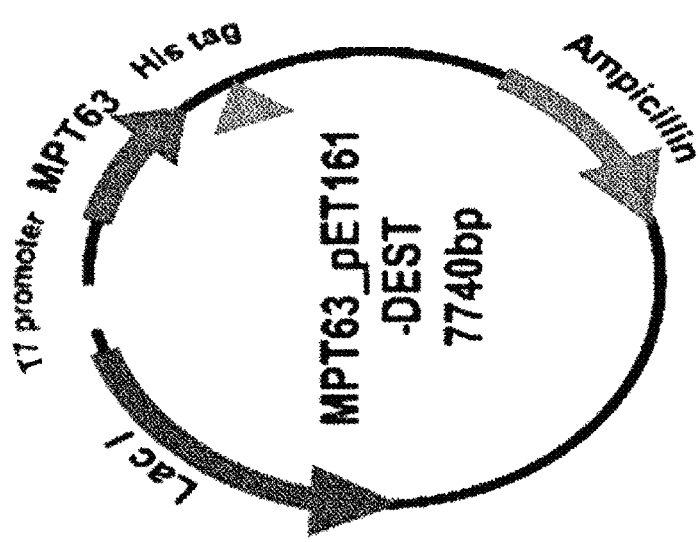

1. Confirmation of the Interaction of MPT63 with TBK1 and p47phox 1-1. Confirmation of the Interaction of MPT63 with TBK1 and p47phox To identify the binding partner of MPT63 in host macrophages, recombinant MPT63 (rMPT63) was co-immunoprecipitated with THP-1 macrophage lysates. For rMPT63, a plasmid was constructed using the 6×His bacterial expression system, and rMPT63 was purified (FIG. 2A).

Figure 2B:
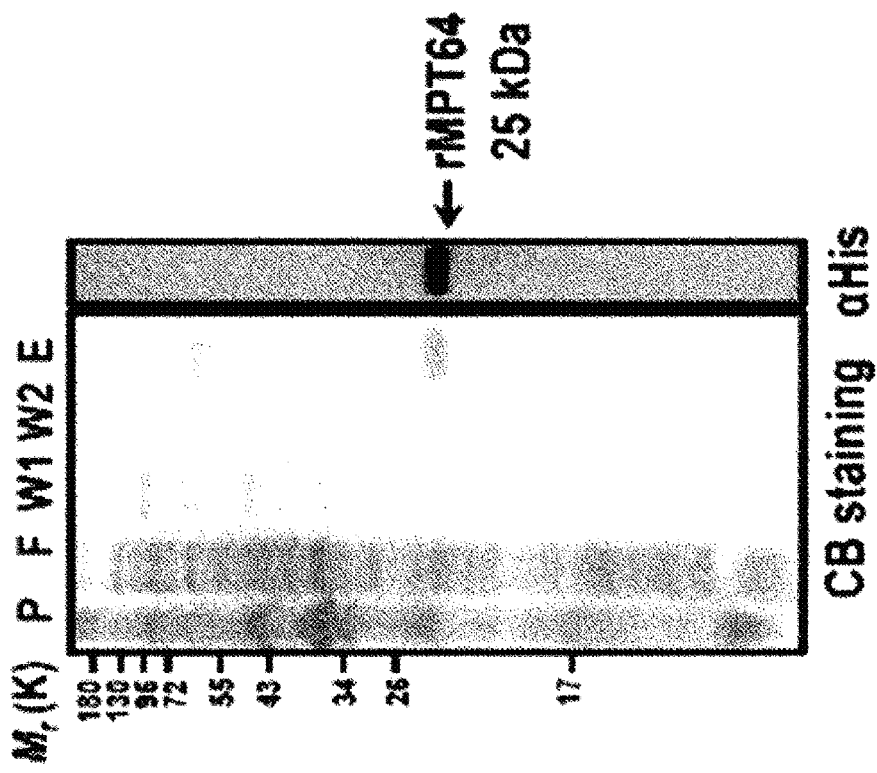
Figure 2B:
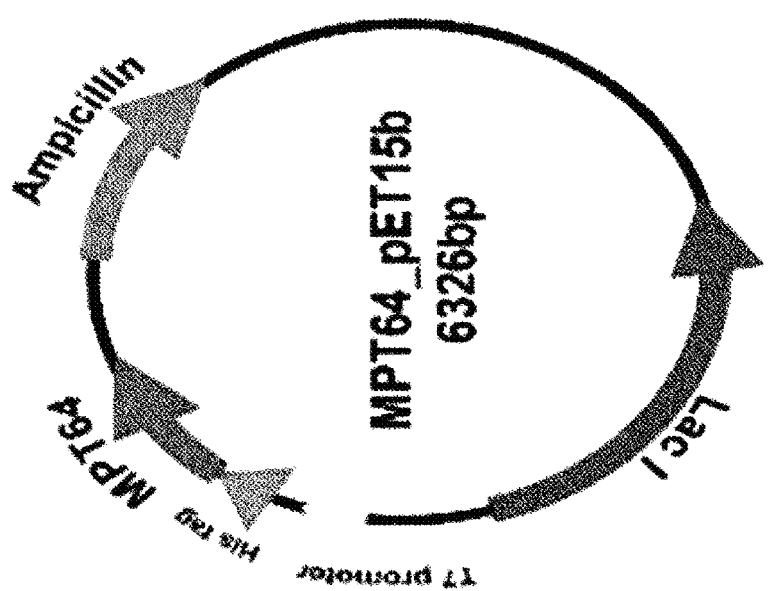
Figure 3A:
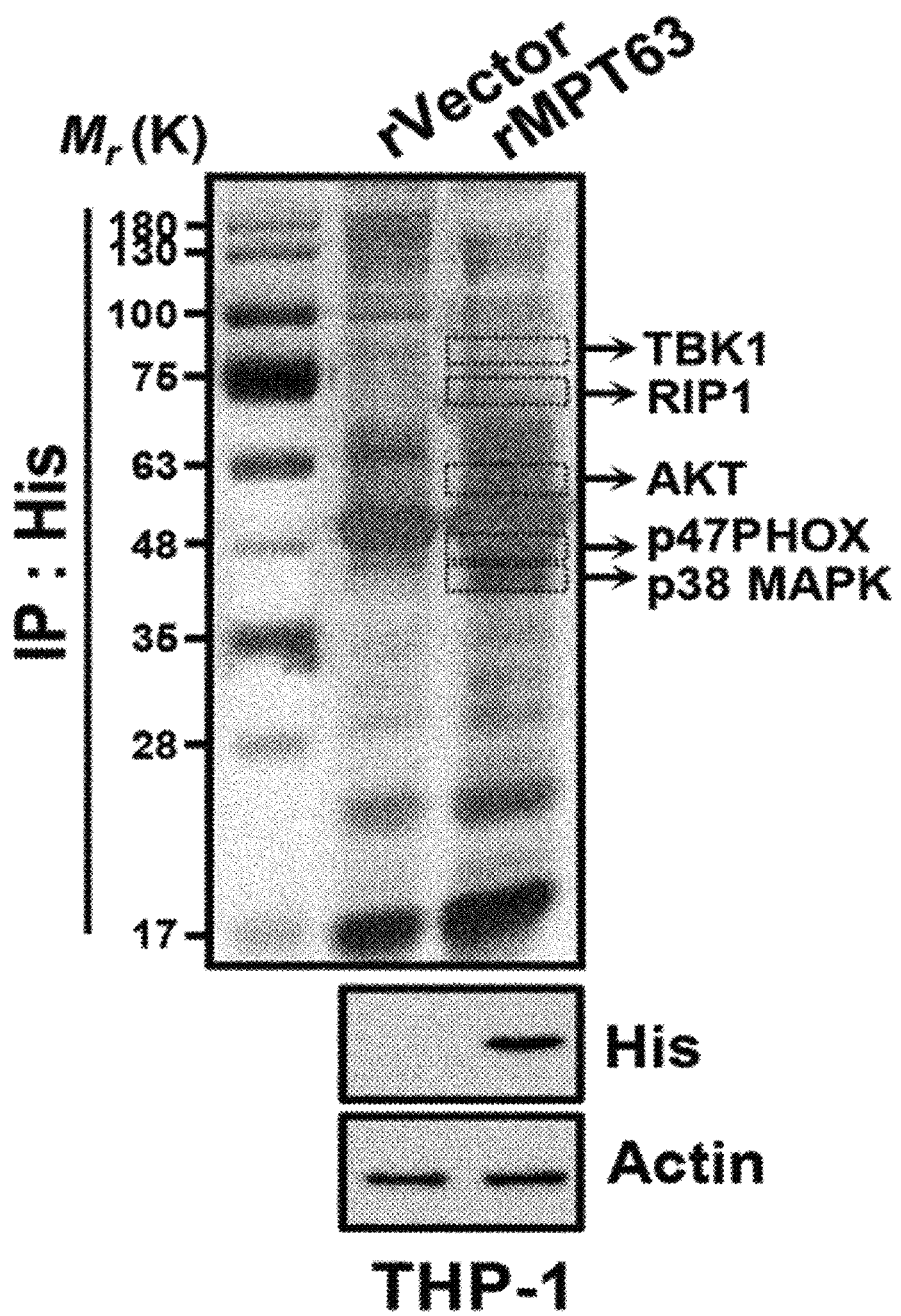
FIG. 3A shows a mass spectrometry result of THP-1 cell lysate treated with rMPT63 or rVector.

The purified rMPT63 complex was identified by mass spectrometry, and TANK-binding kinase (TBK1, 83K), receptor-interacting serine/threonine-protein kinase 1 (RIP1, 75K), RAC-alpha serine/threonine-protein kinase (AKT, 55K), neutrophil cytosol factor 1 (p47phox, 45K), and p38 mitogen-activated protein kinase (MAPK, 38K) was included (FIGS. 3A and 2).

Figure 3B:
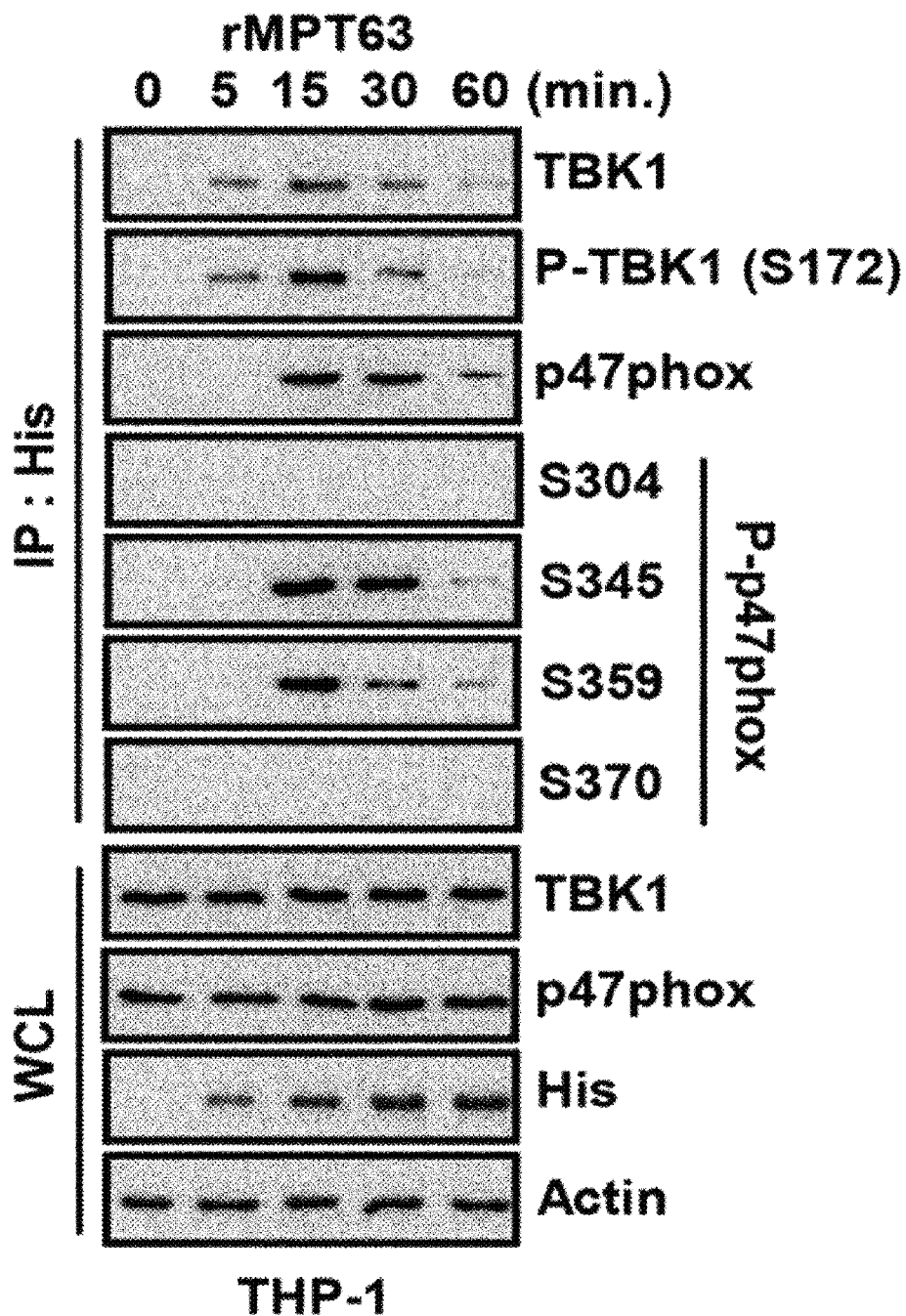
FIG. 3B shows the results of Western blotting by αTBK1, αP-TBK1 (S172), αp47phox, αP-p47phox (S304, 345, 359 and 370), αHis, and αActin after THP-1 cells were stimulated with rMPT63 (5 μg*ml$^{-1}$) for 0, 5, 15, 30, or 60 min, followed by immunoprecipitation (IP) with αHis-agarose beads.

Since TBK1 and p47phox are related to IFN-fl expression and to increase the level of reactive oxygen species in tuberculosis, TBK1 and p47phox were selected to check the interaction with MPT63 in detail. To investigate the endogenous interaction of macrophages, THP-1 cells were treated with rMPT63, and co-immunoprecipitation was performed. As a result, in THP-1 cells, rMPT63 endogenously interacted with TBK1 and p47phox and, interestingly, also interacted with phosphorylated p47phox (S345 and 5359) (FIG. 3B).

Figure 3C:
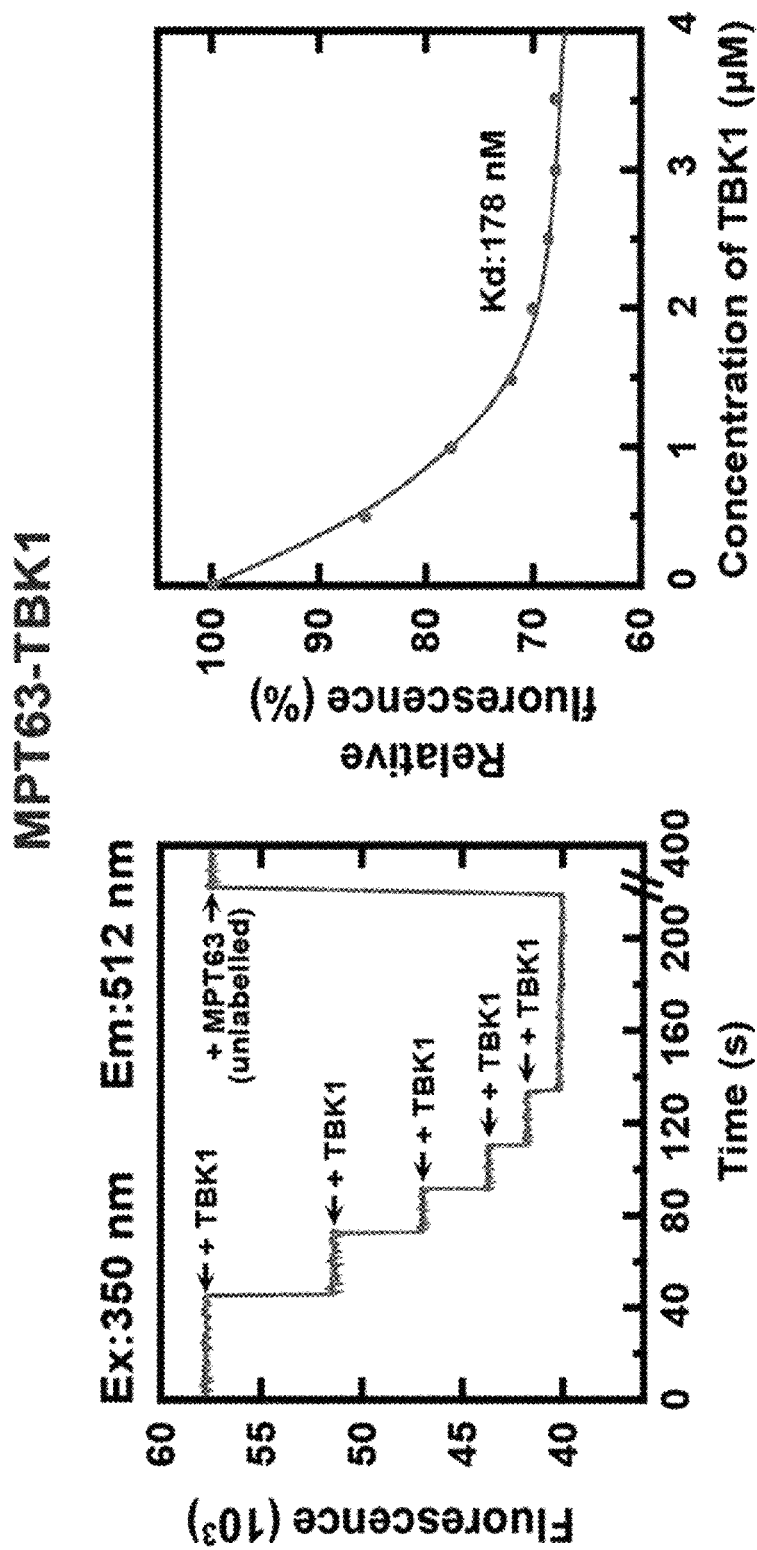
FIGS. 3C and 3D show the results of titration of MPT63 fluorescently labeled with TBK1 and p47phox (left graph), and $K_d$ (178 and 345 nM) values confirmed by curve fitting analysis (right graph)
Figure 3D:
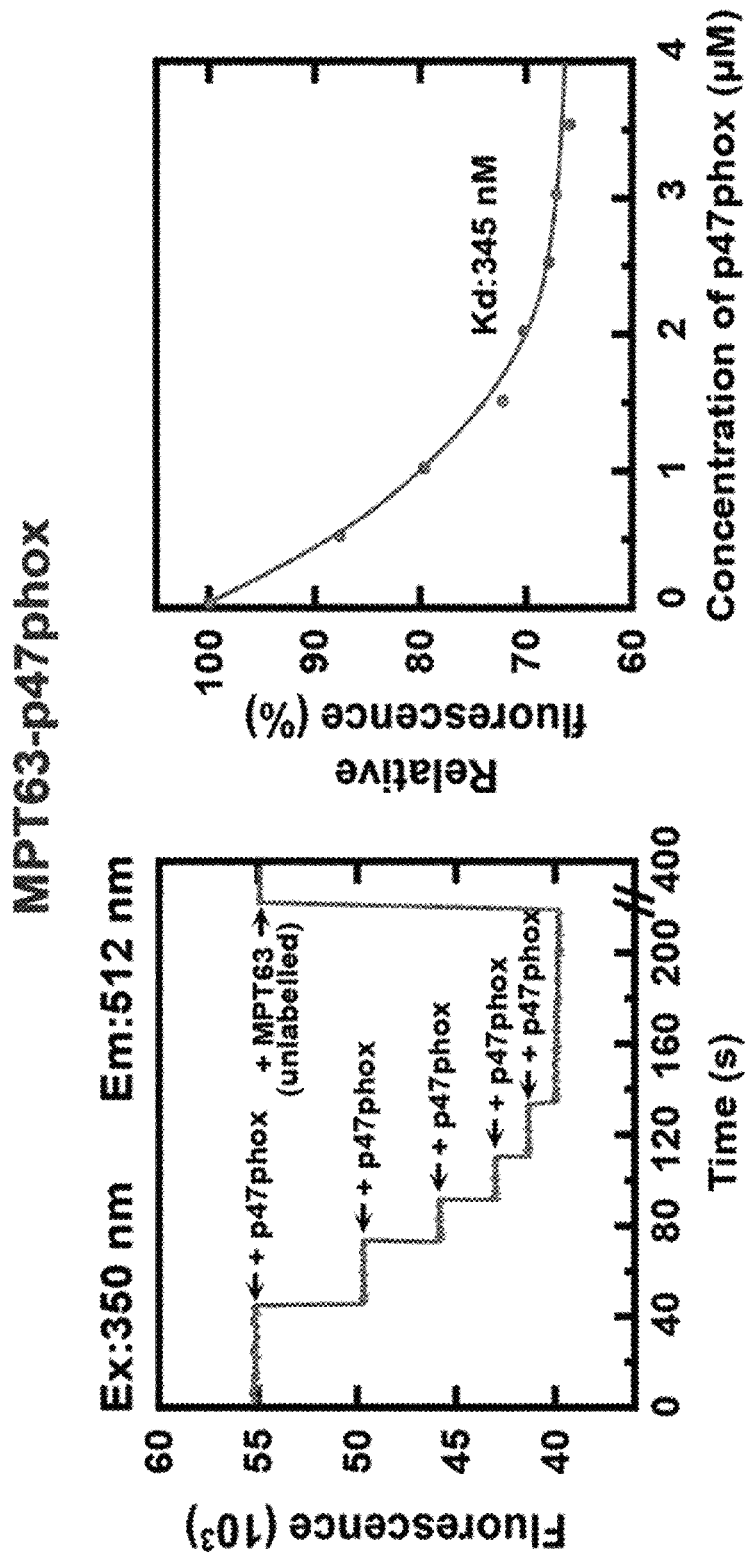
Figure 3E:
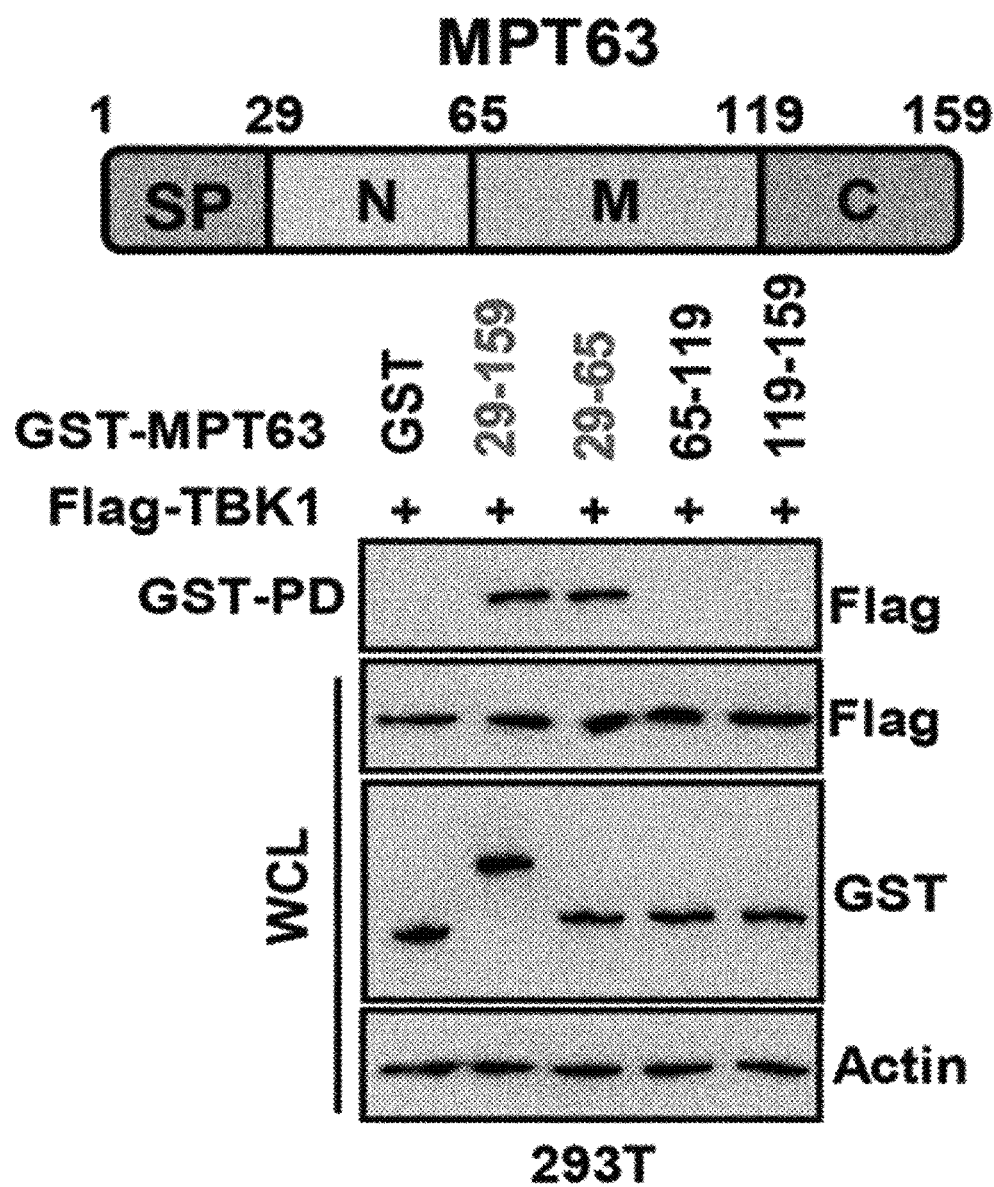
FIGS. 3E and 3G are diagrams of the MPT63 structure (top), a truncated mutant structure of mammalian GST (glutathione S-transferase) or GST-MPT63, and the results of Western blotting using αFlag or αV5, αGST and αActin for 293T cell lysates transfected with Flag-TBK1 or V5-p47phox for 48 hours.
Figure 3F:
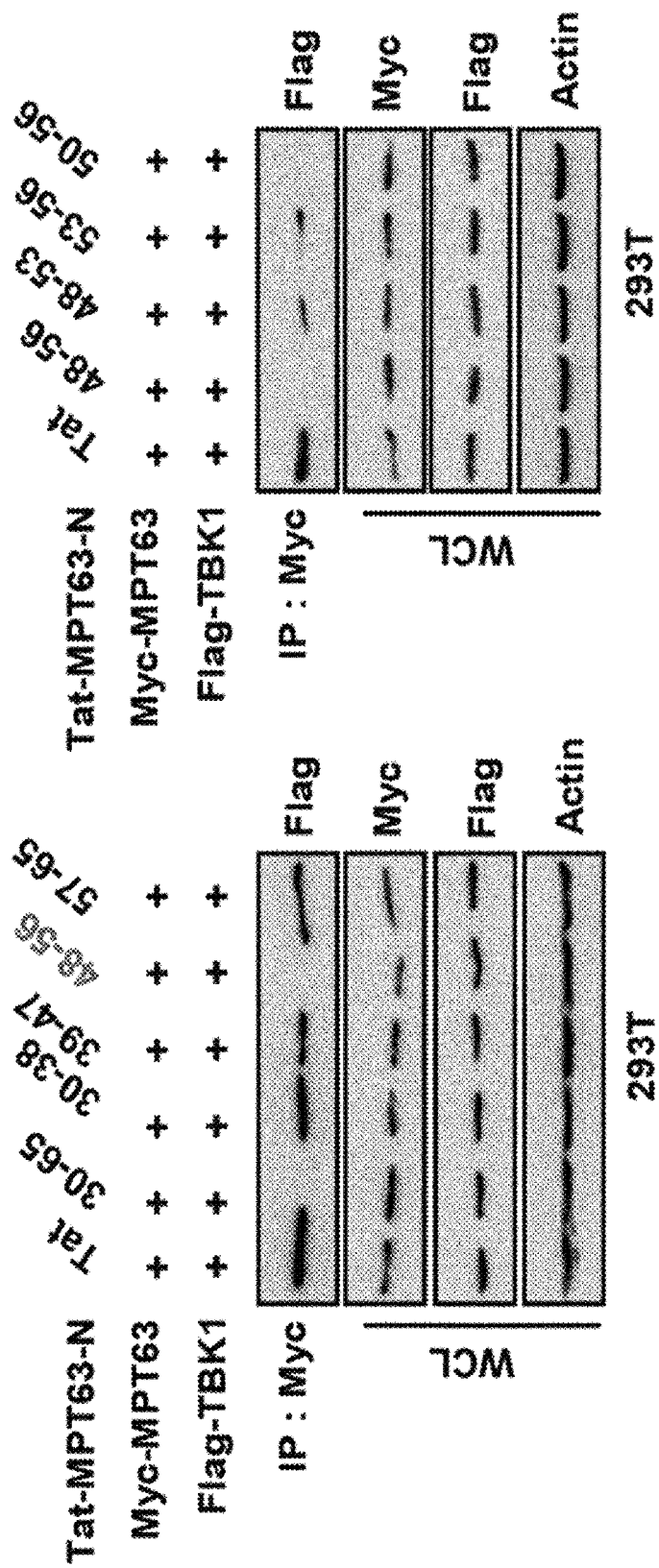
FIGS. 3F and 3H shows the results of immunoprecipitation using αMyc and Western blotting using αFlag on cell lysates after Myc-MPT63 and Flag-TBK1 or V5-p47phox are expressed in 293T cells, and they are treated with various Tat-MPT63-N or MPT63-C peptides (10 μM) for 6 hours.

In addition, to measure the interaction between MPT63 and TBK1 or p47phox in vitro, fluorescently labeled MPT63 recombinant protein and TBK1 or p47phox were used, and as a result, high affinity was confirmed (TBK1, 178 nM; p47phox, 345 nM) (FIGS. 3C and 3D).

1-2. Identification of Regions of MPT63 Involved in Binding to TBK1 or p47phox

Recombinant MPT63 (rMPT63) comprises a signal peptide, N-terminus, middle, and C-terminus. In order to find the domain for the interaction between rMPT63 and TBK1 or p47phox, the domains of GST-MPT63 and Flag-TBK1 or V5-p47phox, respectively, were used. In 293T cells, the N-terminus of MPT63 was combined with TBK1 and 48-56 peptide, confirming that it was essential for the interaction between MPT63 and TBK1. Specifically, it could be predicted that amino acid residues at positions 50-56 except for G53 were essential for binding between MPT63 and TBK1.

Figure 3G:
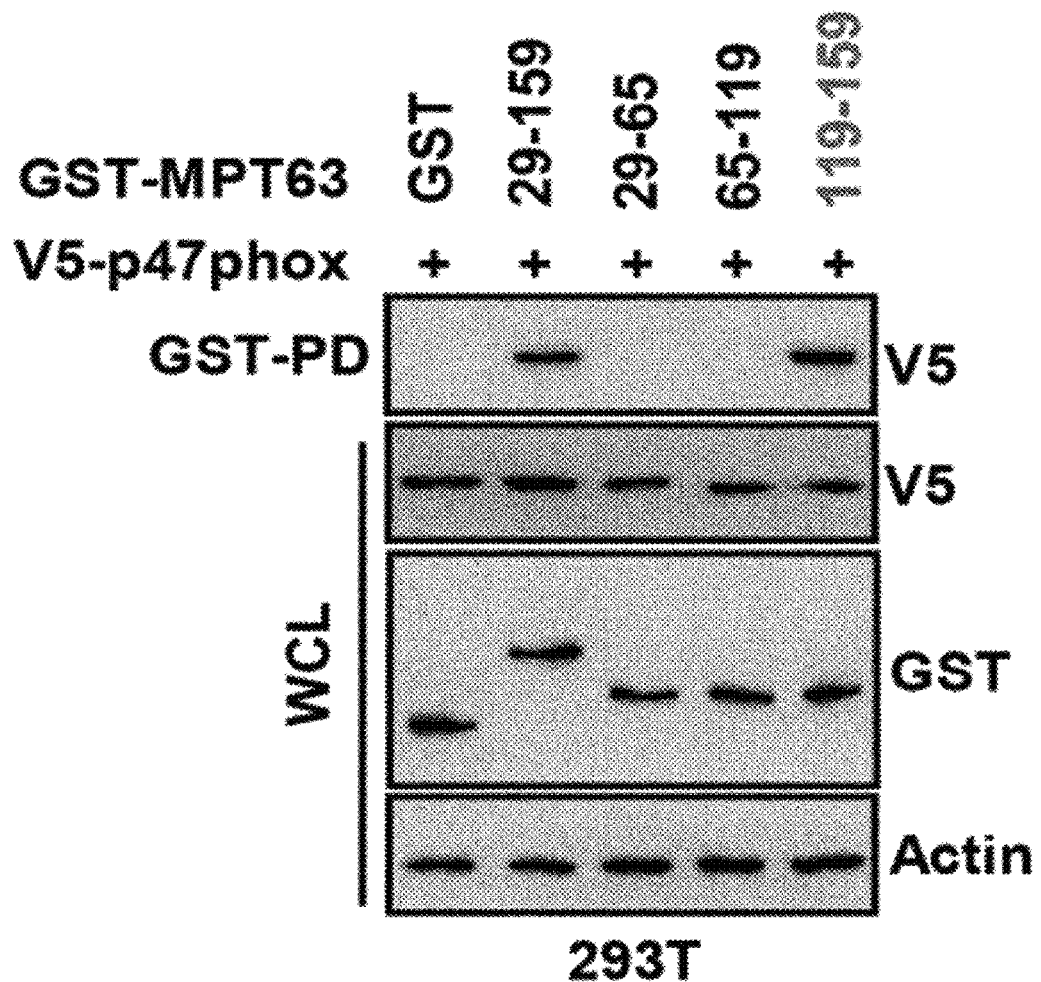
Figure 3H:
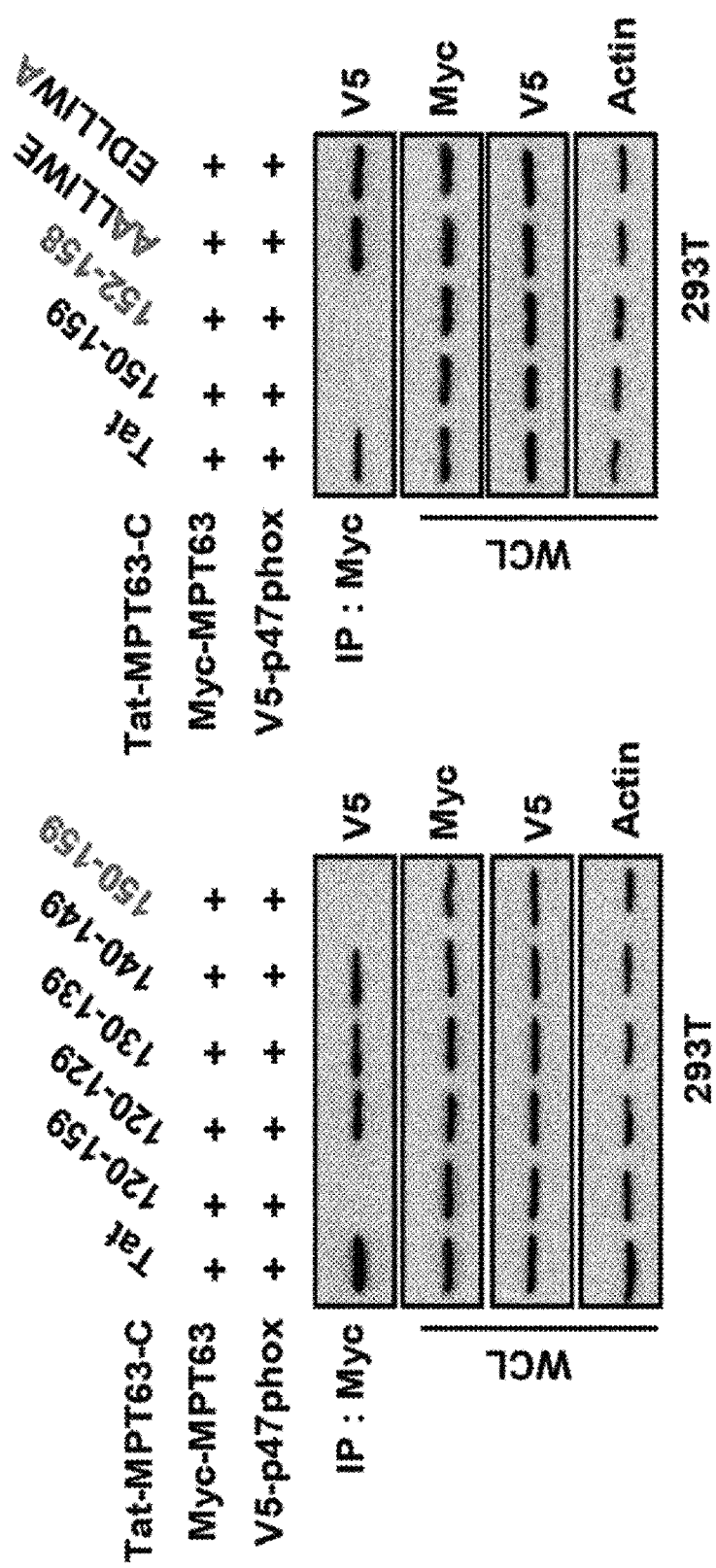

Then, in order to investigate the binding region between MPT63 and p47phox, 293T cells were transformed with GST-MPT63 and V5-p47phox, and GST pulldown was performed. As a result, it was confirmed that the amino acid residues at positions 150-159 in the C-terminal region of MPT63, in particular, are important for binding to p47phox at the C-terminus of MPT63. Further, it was confirmed that E152, D153, L154, and E158 are key amino acids in the interaction between MPT63 and p47phox (FIGS. 3G and 3H).

Further, in order to examine the MPT63-binding portion of TBK1 or p47phox, a truncated mutant of GST-TBK1 or p47phox was pulled down into wild-type Myc-MPT63. The kinase domain of TBK1 was essential for binding MPT63 in 293T cells, and the PX domain of p47phox was important for interaction with MPT63 (FIGS. 5A-5F).

From the above results, it may be seen that MPT63 binds to TBK1 and p47phox through the N-terminus or C-terminus of MPT63.

2. Confirmation the Interaction of MPT64 with TBK1 and MPT64 with HK2

2-1. Confirmation the Interaction of MPT64 with TBK1 and MPT64 with HK2

Figure 4A:
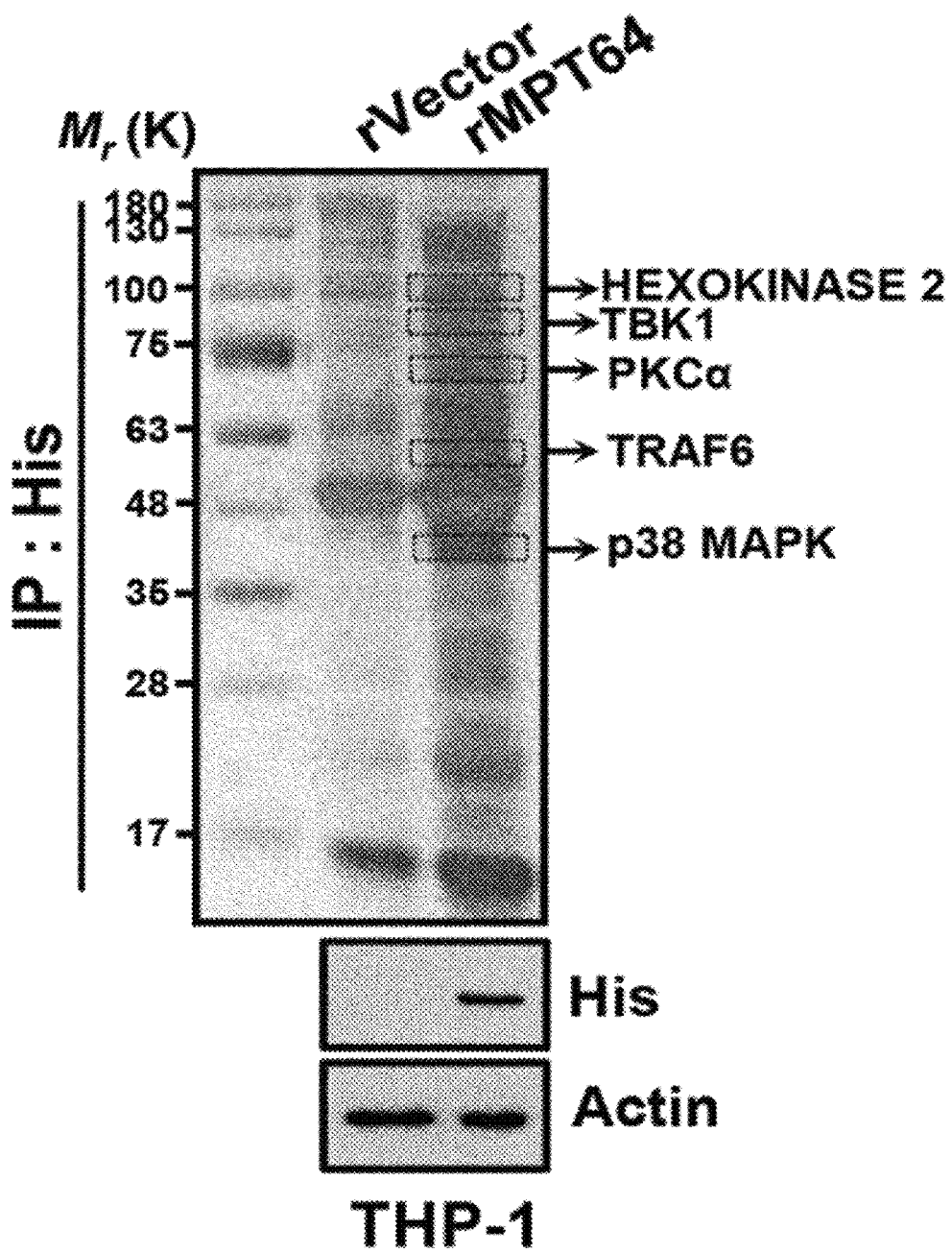
FIG. 4A shows the results of mass spectrometry of THP-1 cell lysate treated with rMPT64 or rVector.
Figure 4B:
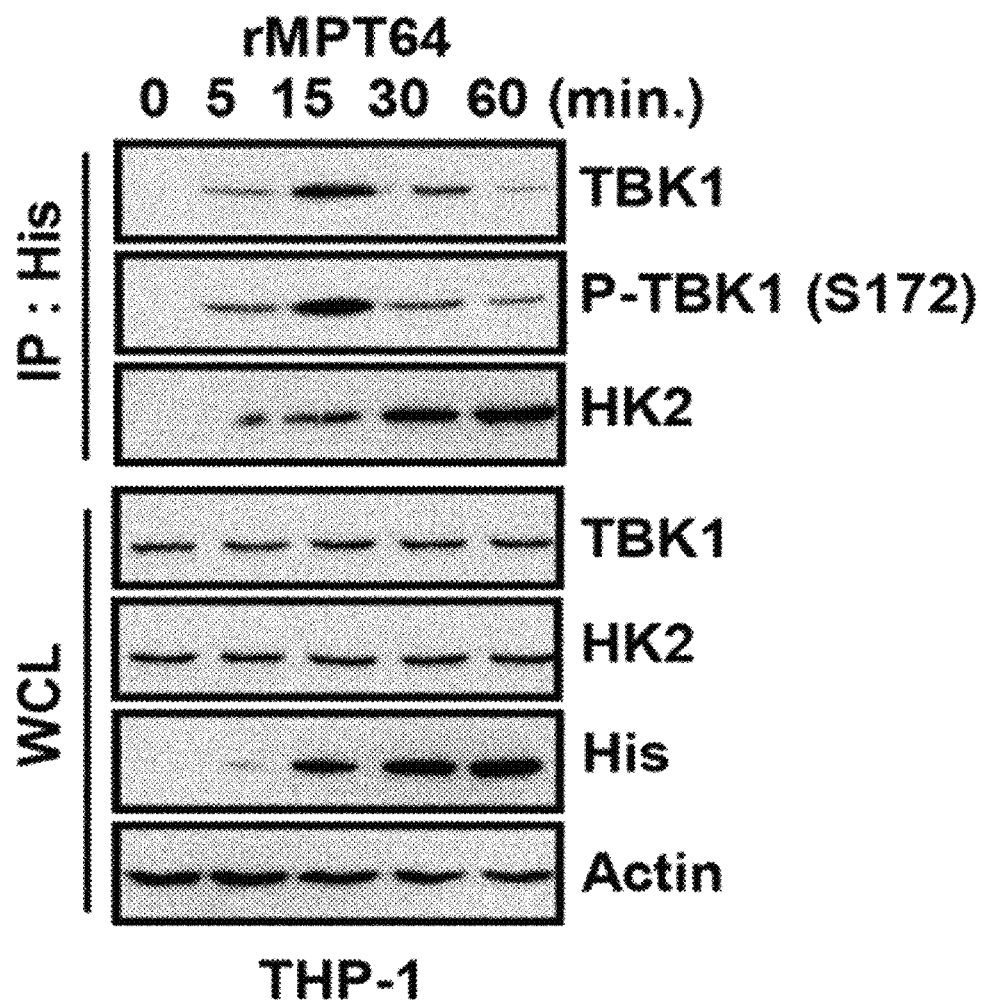
FIG. 4B shows the results of Western blotting by αTBK1, αP-TBK1 (S172), αHK2, αHis, and αActin after THP-1 cells were stimulated with rMPT64 (5 μg*ml$^{-1}$) for 0, 5, 15, 30, or 60 min, followed by immunoprecipitation with αHis-agarose beads.

To investigate the binding partner of MPT64 in host cell proteins, immunoprecipitation was performed by treating THP-1 cell lysate with recombinant MPT64 (rMPT64). Bacterial expression system produced rMPT64 like MPT63 (FIG. 2B). Through the purification of the rMPT64 complex, it was confirmed that rMPT64 interact with several host proteins such as hexokinase 2 (HK2, 102K), TBK1 (83K), protein kinase Cα (PKCα, 76K), TNF receptor associated factor 6 (TRAF6, 60K) and p38MAPK (38K) (FIG. 4A). Interestingly, TBK1 also bound to MPT64.

Next, the interaction between HK2 and MPT64, which is essential for glycolysis and plays an important role in the immune response through the regulation of glycolysis in tuberculosis, was investigated. To investigate the endogenous binding of MPT64 to TBK1 and HK2, rMPT64 was treated. As a result, it was confirmed that phosphorylated TBK1 (S172) also interacts with rMPT64.

Figure 4C:
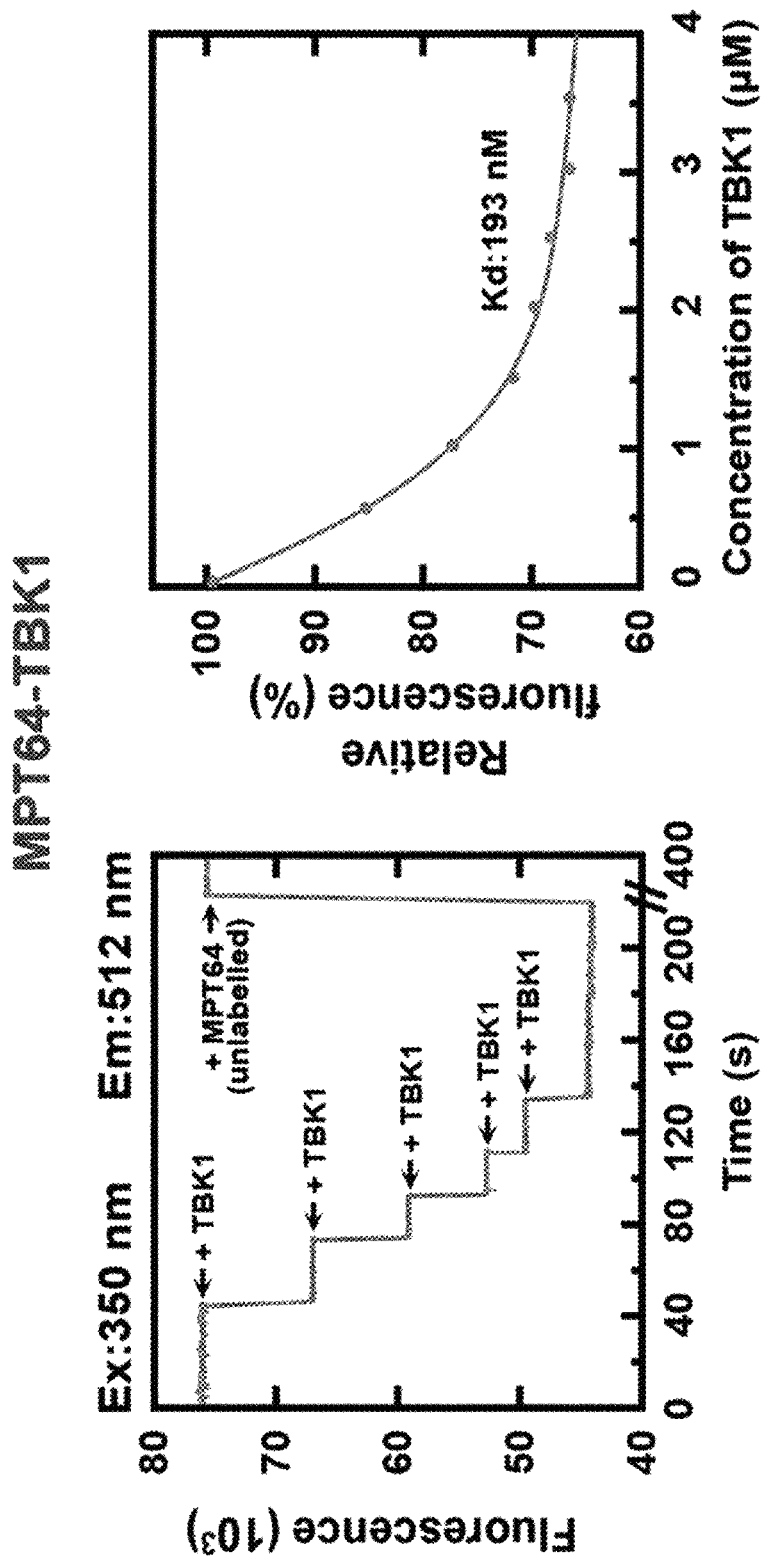
FIGS. 4C and 4D are results of titration of MPT64 fluorescently labeled with TBK1 and HK2 (left graph), and $K_d$ (193 and 134 nM) values confirmed by curve fitting analysis (right graph)
Figure 4D:
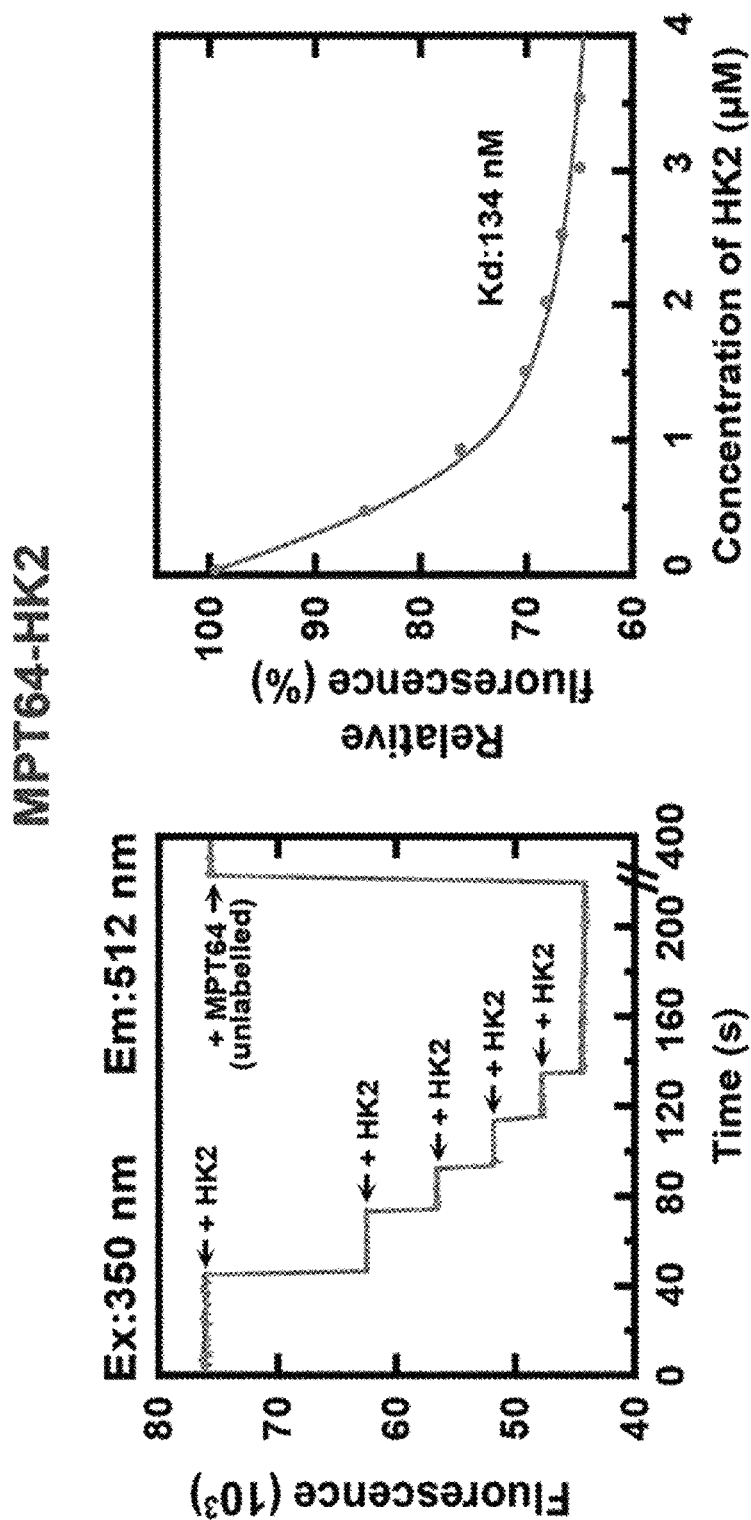

In addition, in vitro binding between MPT64 and TBK1 or HK2 was analyzed using a protein recombined with fluorescently labeled MPT64 or p47phox, and high mutual affinity was confirmed (TBK1, 193 nM, p47phox, 134 nM) (FIGS. 4C and 4D).

2-2. Identification of Regions of MPT64 Involved in Binding to TBK1 or HK2

Figure 4E:
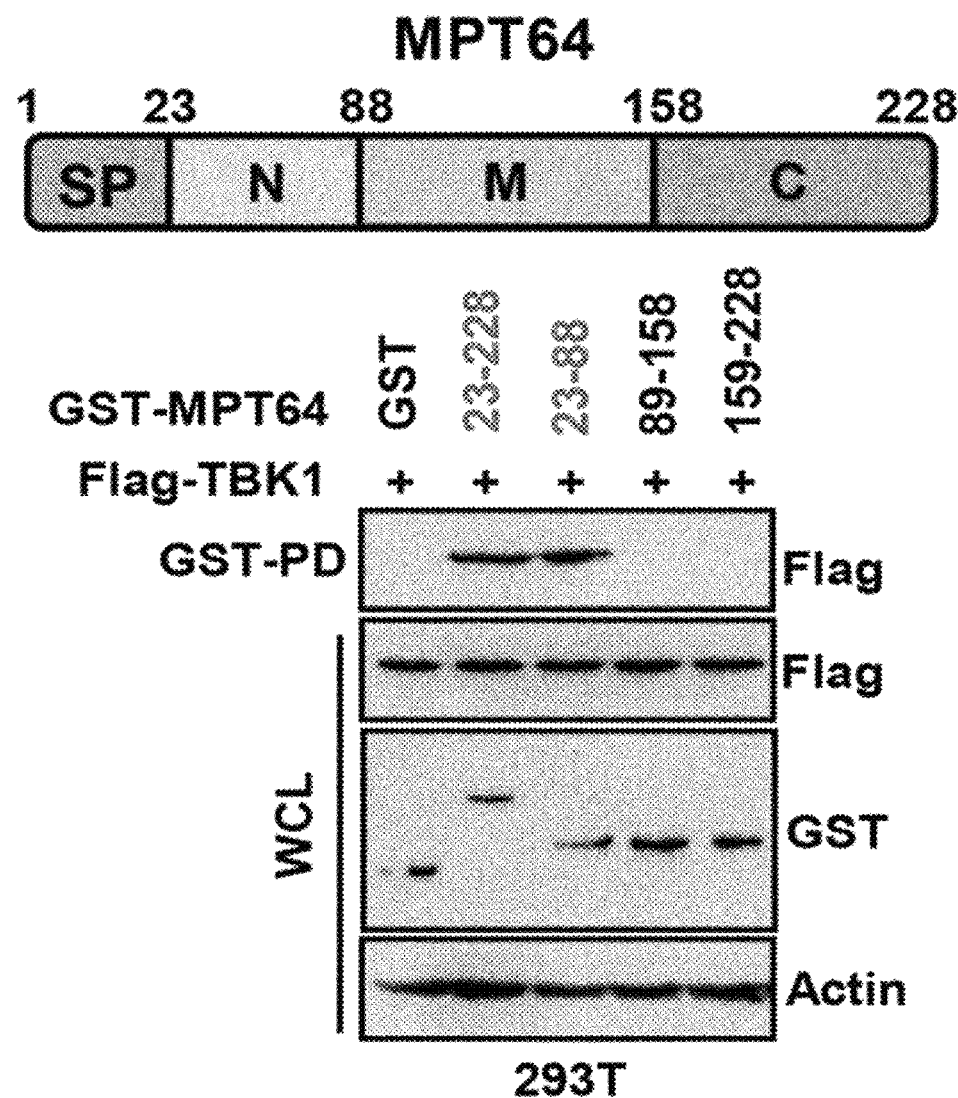
FIGS. 4E and 4G are diagrams of the MPT64 structure (top), a truncated mutant structure of mammalian GST (glutathione S-transferase) or GST-MPT64, and the results of Western blotting using αFlag or αGST and αActin for 293T cell lysates transfected with Flag-TBK1 or Flag-HK2 for 48 hours.
Figure 4F:
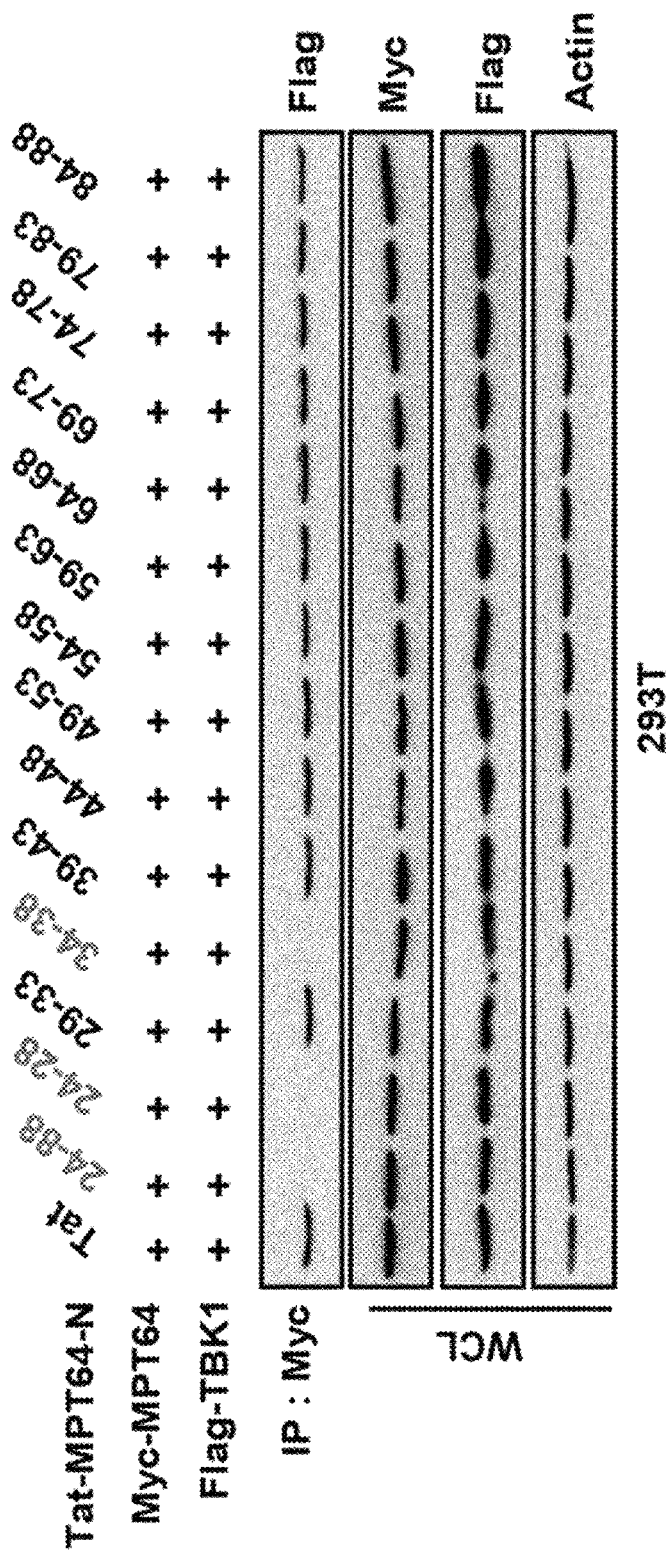
FIGS. 4F and 4H shows the results of immunoprecipitation using αMyc and Western blotting using αFlag on cell lysates after Myc-MPT64 and Flag-TBK1 or Flag-HK2 are expressed in 293T cells, and they are treated with various Tat-MPT64-N or MPT64-C peptides (10 μM) for 6 hours.
Figure 4G:
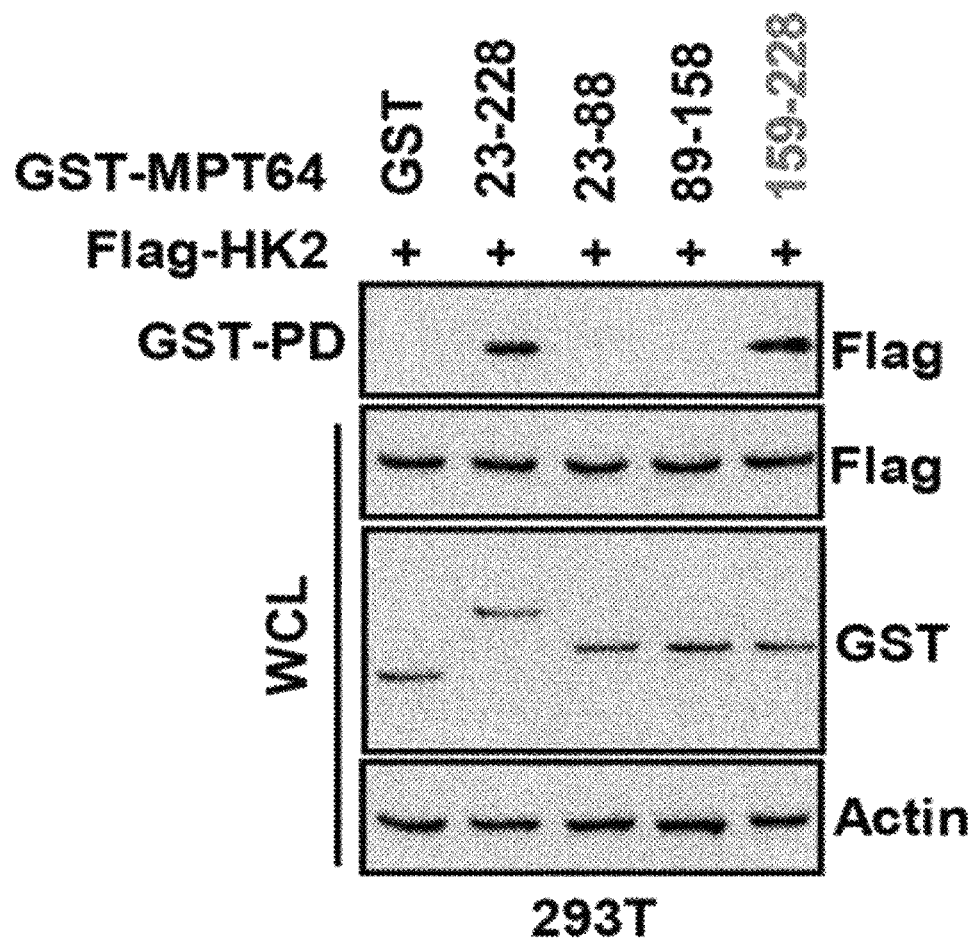
Figure 4H:
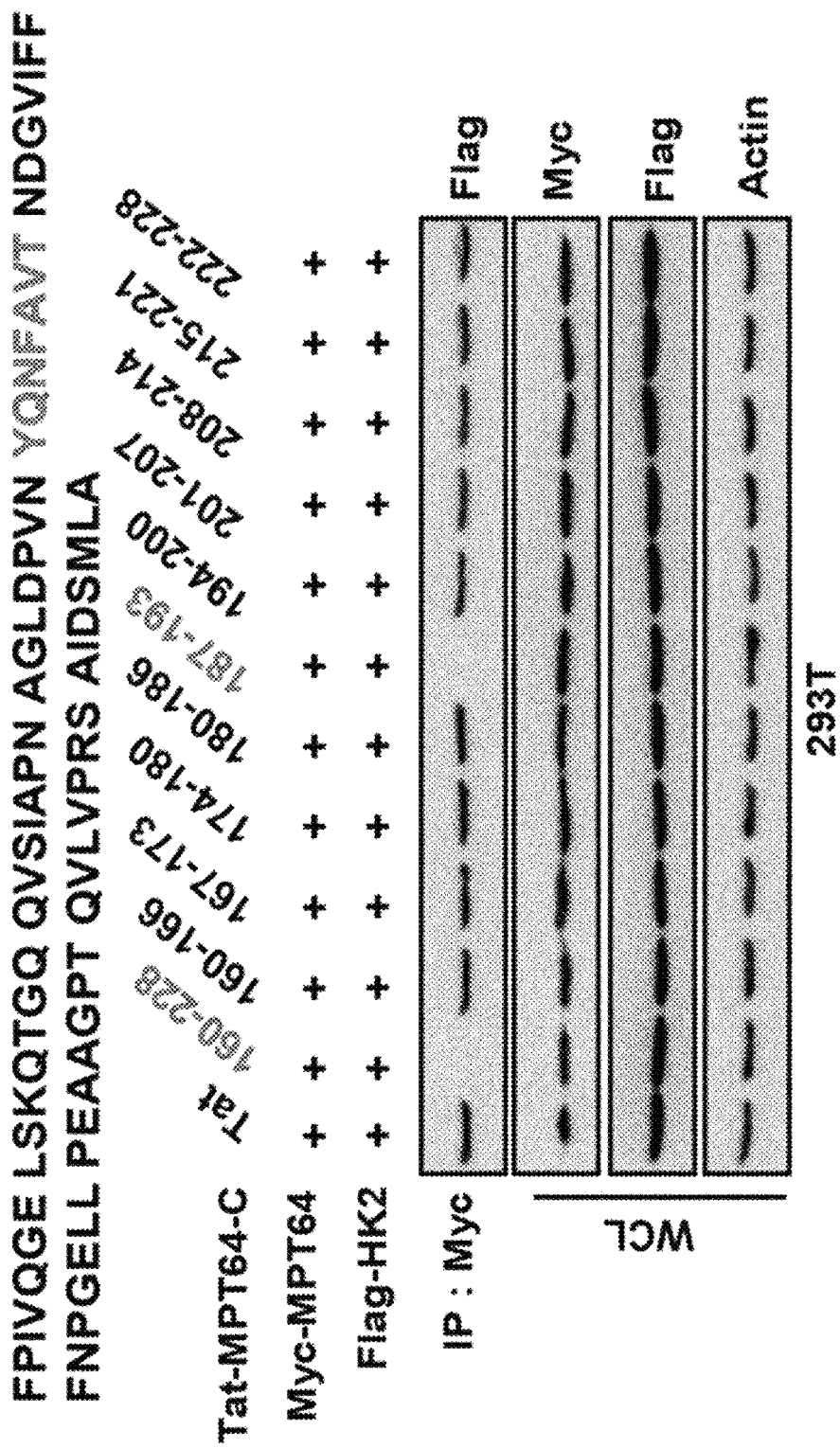

To identify the domains that interact with TBK1 and HK2 in MPT64, 293T cells were transfected with truncated GST-MPT64 and wild-type flag-TBK1 or flag-HK2, and GST pulldown analysis was performed. It was confirmed that the key amino acid residues for binding to the N-terminal region of MPT64 interacting with TBK1 were amino acids at positions 24 to 28 and 34 to 38 (FIGS. 4E and 4F).

The C-terminus of MPT64 was associated with HK2, and the essential peptide was located between positions 187 to 193.

Figure 5D:
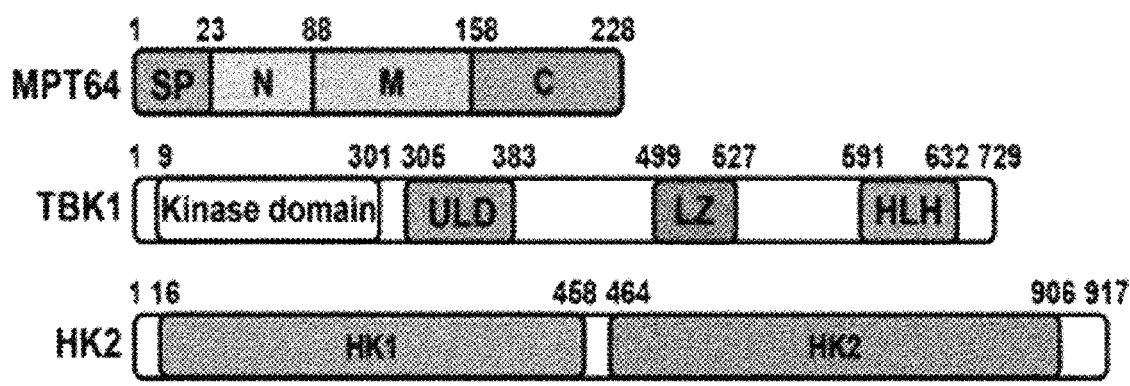
Figure 5E:
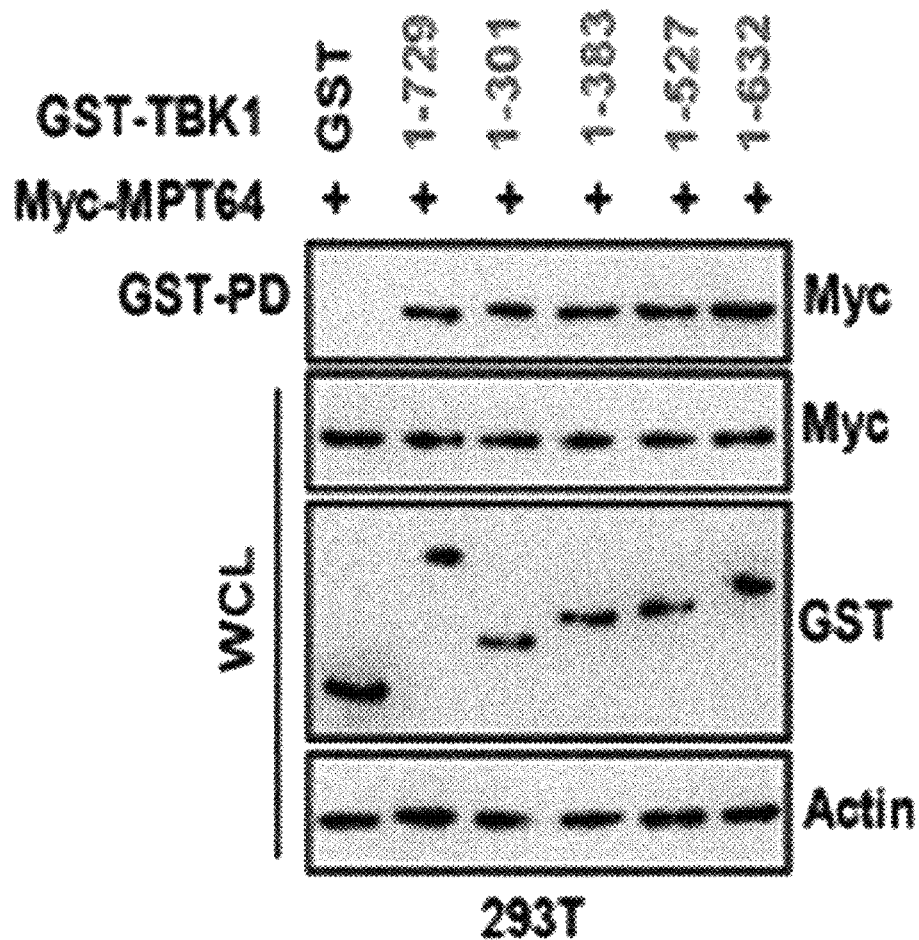
Figure 5F:
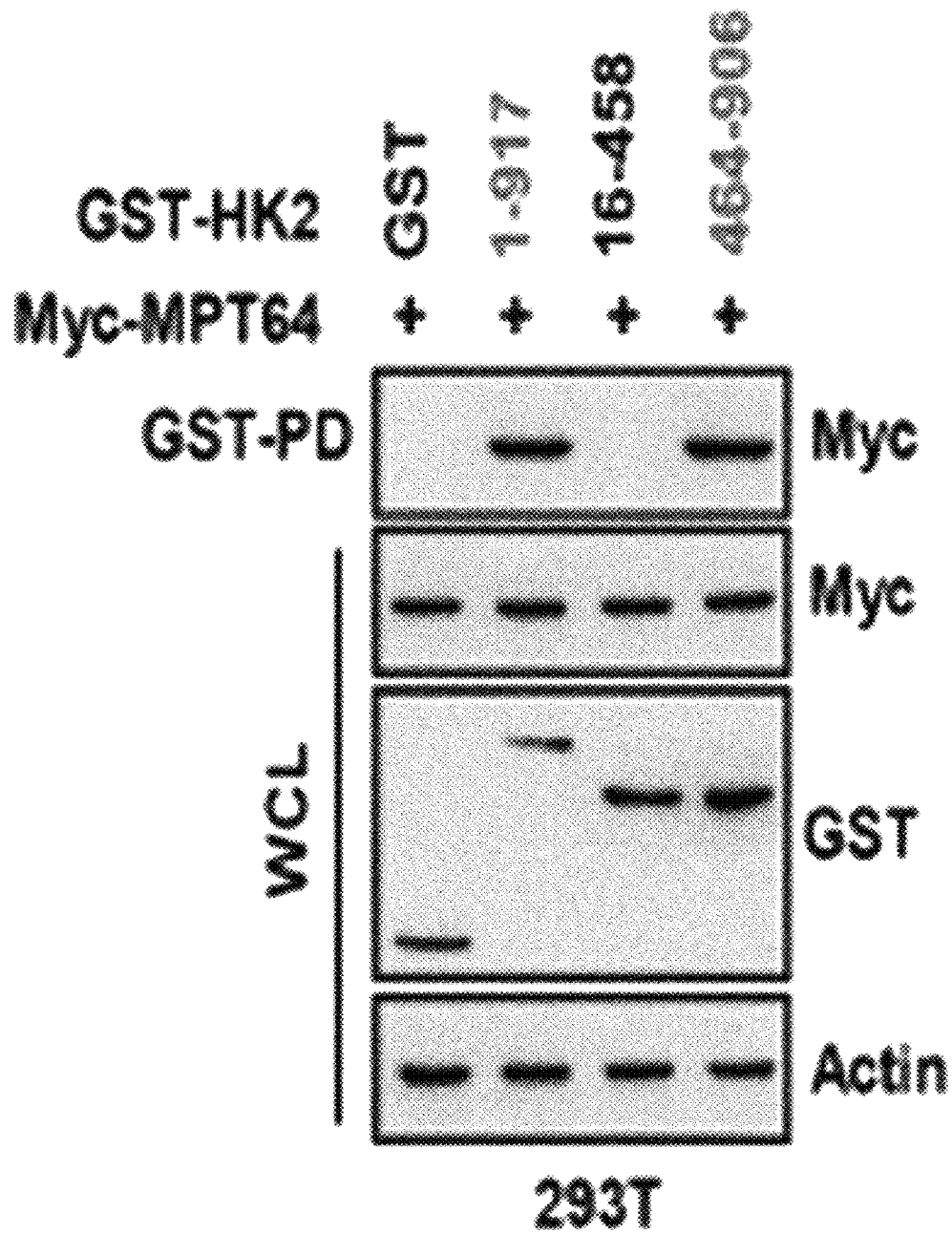

Further, to confirm the interaction site of TBK1 and HK2, wild-type or truncated TBK1 or HK2 was transfected using wild-type Myc-MPT64. The kinase region of TBK1 (1-301) and the HK2 region of HK2 were found to be essential for interaction with MPT64 (FIGS. 5D to 5F).

From the above results, it may be seen that MPT64 binds to TBK1 and HK2 through the N or C terminus of MPT64.

3. Confirmation of Antibacterial Activity of TBK1 Binding Peptide Through STING-TBK1-IRF3 Pathway To investigate the role of MPT64 and TBK1 interaction, wild type or truncated mutant TBK1 peptides (R9, TBK1 peptides [MPT63, MPT64, MPT63/64] containing MPT63 or/and MPT64-interacting regions indicated in previous results was prepared (FIG. 6A).

Figure 6B:
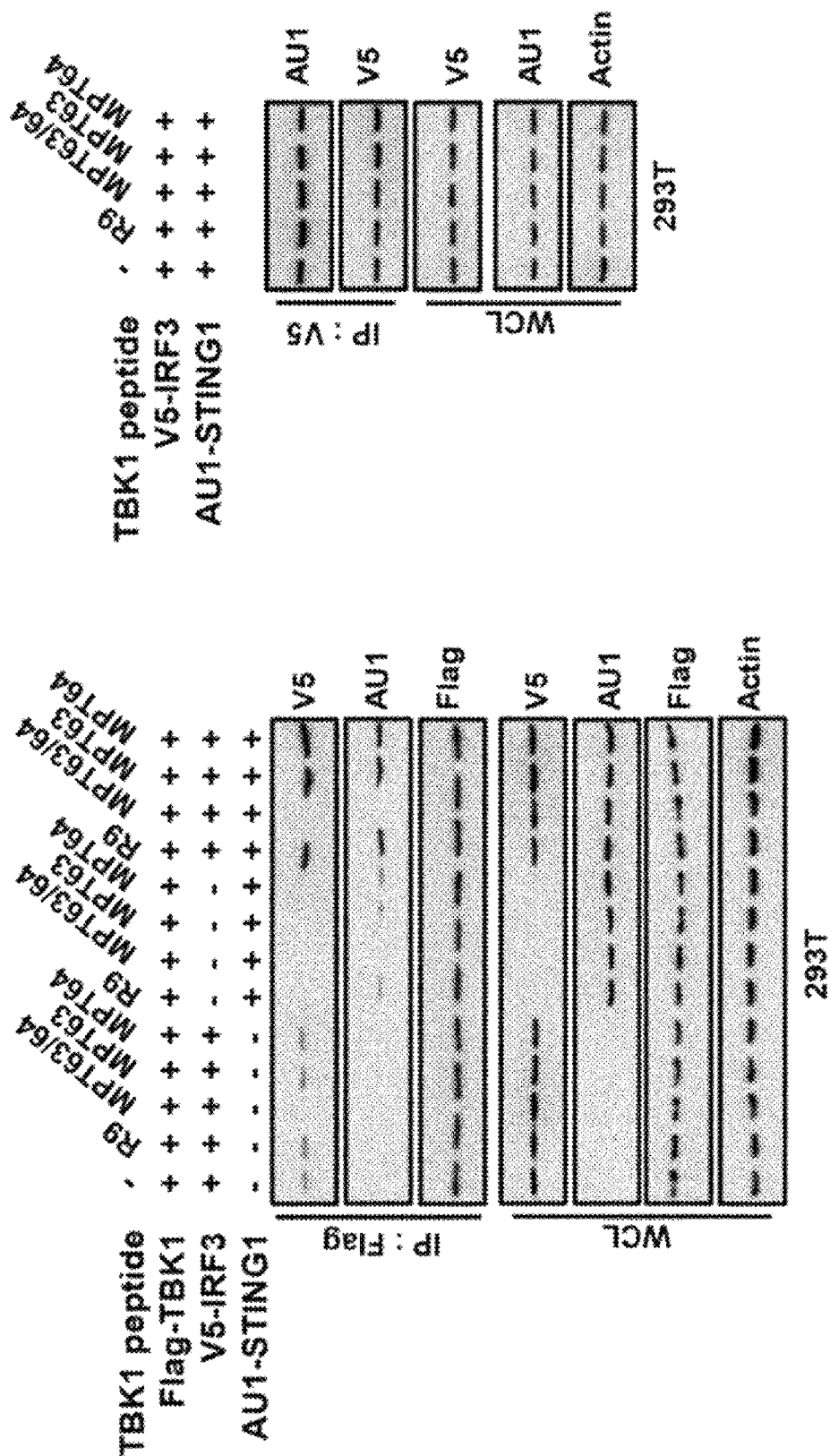
FIG. 6B shows the results of immunoprecipitation and Western blotting after 293T cells are transfected with V5-IRF3 and/or AU1-STING1, and they are treated with 1 μM of TBK1 peptide and/or Flag-TBK1 for 6 hours (left), and the right side is a result of immunoprecipitation and Western blotting without Flag-TBK1 treatment.

TBK1 forms a complex as an essential component of the STING-TBK1-IRF3 pathway and induces the expression of IFN-β. To investigate interactions with components of the STING-TBK1-IRF3 pathway, Flag-TBK1, V5-IRF3, AU1-STING1 were co-transfected together with TBK1 peptide. The interaction between TBK1 and IRF3 and STING1 was inhibited by the MPT63/64-TBK1 peptide, but the interaction between IRF3 and STING1 was not inhibited (FIG. 6B).

Figure 6C:
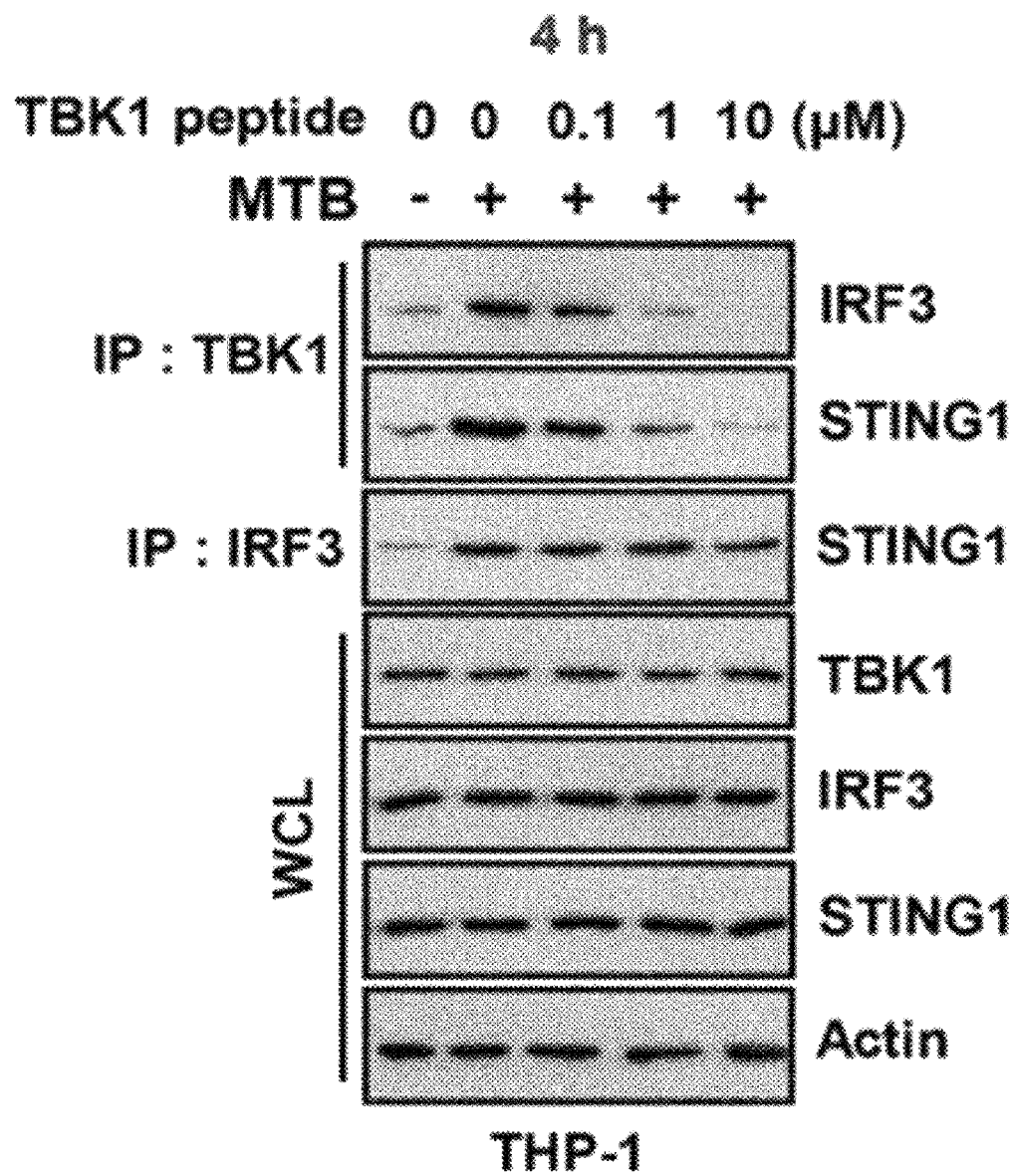
FIGS. 6C and 6D show the results of immunoprecipitation and Western blotting after THP-1 cells and BMDM cells (TBK1$^{+/+}$ or TBK1$^{-/-}$) are infected with *Mycobacterium tuberculosis* for 4 hours and treated with TBK1 peptide at various concentrations.
Figure 6D:
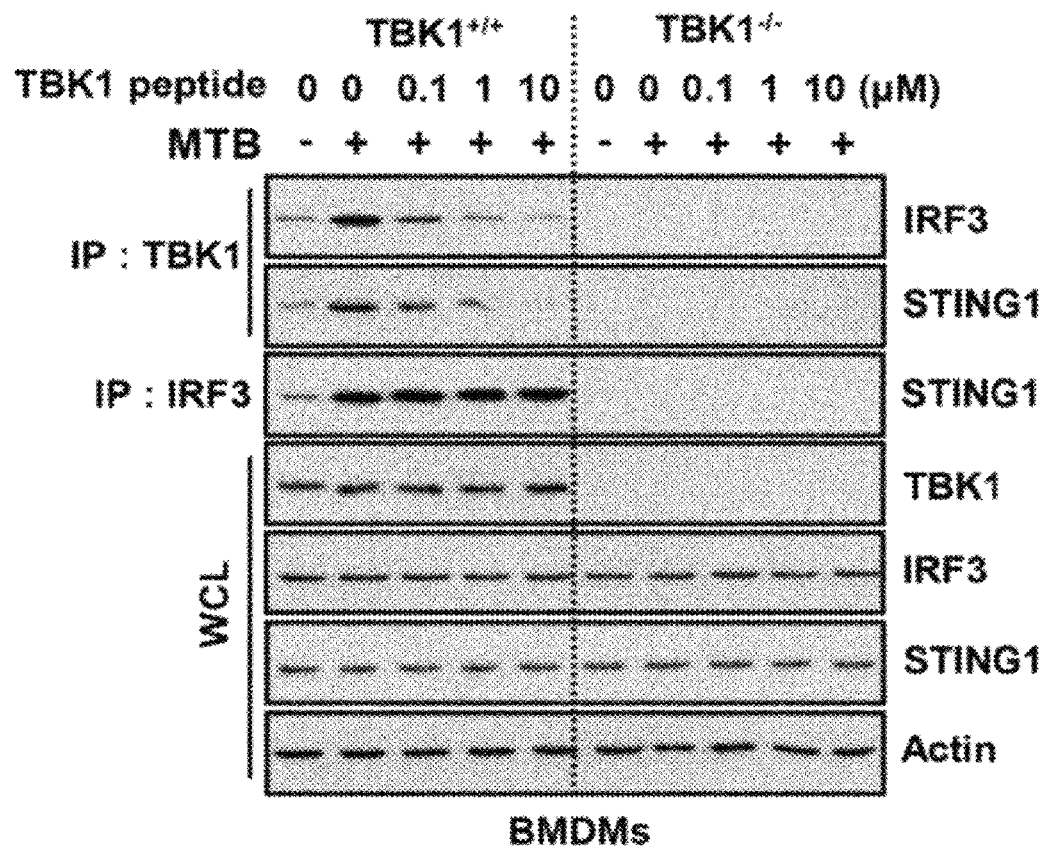

Mycobacterium tuberculosis (MTB) induces an increase in the expression of IFN-β, activates STING1-TBK1-IRF3, and modulates inflammation to survive in the host. The anti-tuberculosis activity of MPT63/64-TBK1 was confirmed using THP-1 cells infected with Mycobacterium tuberculosis. The complex of STING1-TBK1-IRF3 decreased in proportion to the concentration in MPT63/64-TBK1 (FIG. 6C). In TBK1 knockout bone marrow-derived macrophages (BMDM), the interaction between IRF3 and STING1 could not be confirmed regardless of the MPT63/64-TBK1 peptide (FIG. 6D).

Figure 6E:
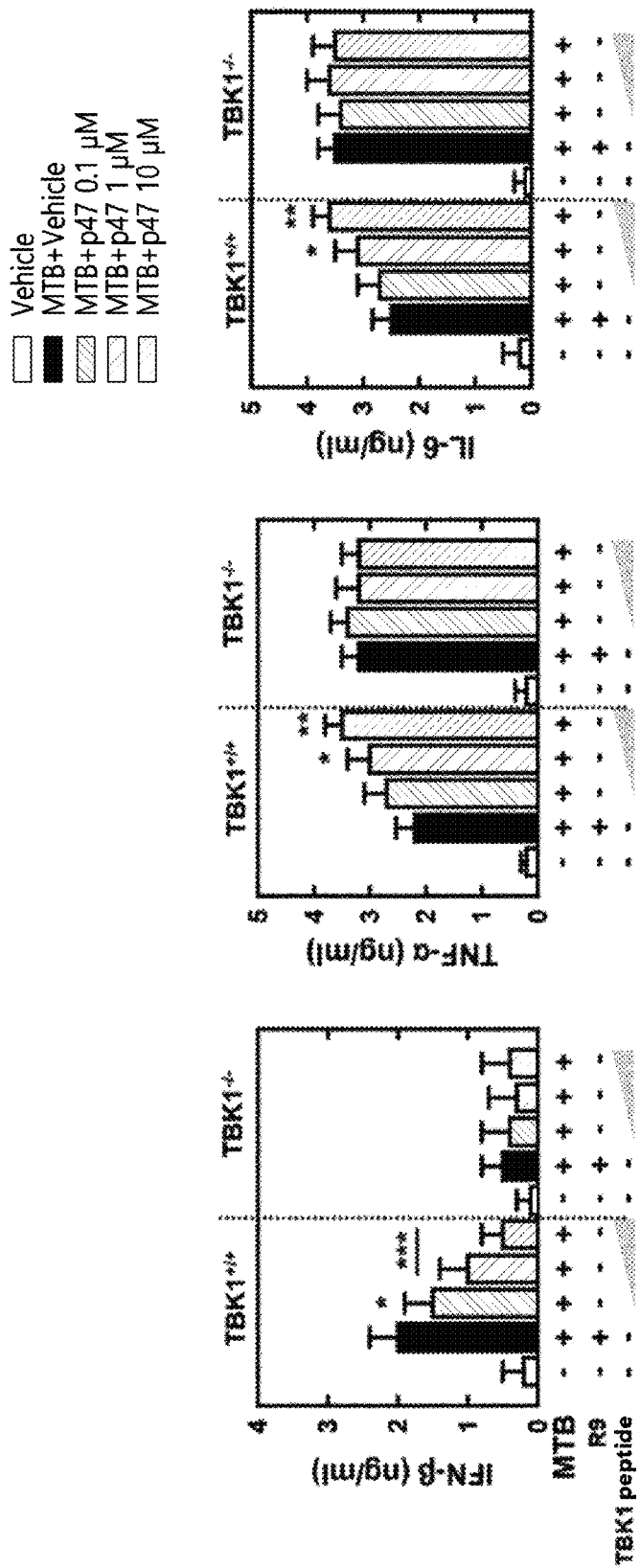
FIG. 6E shows the results of the level of IFN-β, TNF-α and IL-6 in BMDM supernatant obtained by ELISA after that BMDM cells (TBK1$^{+/+}$ or TBK1$^{-/-}$) are infected with *Mycobacterium tuberculosis* for 4 hours and treated with TBK1 peptide at various concentrations, and 18 hours later.
Figure 6F:
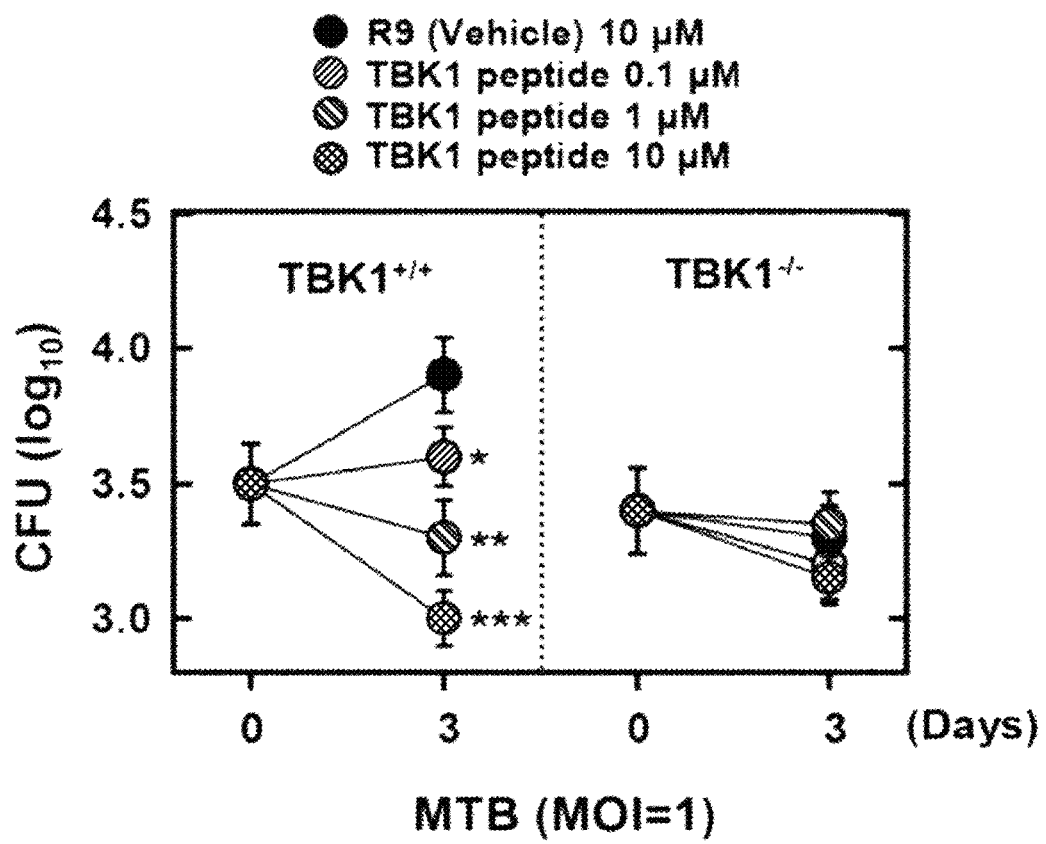
FIG. 6F is a diagram confirming the amount of *Mycobacterium tuberculosis* over time after that BMDM cells (TBK1$^{+/+}$ or TBK1$^{-/+}$) are infected with *Mycobacterium tuberculosis* for 4 hours and treated with TBK1 peptide at various concentrations.

Increased levels of inflammatory cytokines such as TNF-α and IL-6 are essential for antibacterial activity in the host. Mycobacterium tuberculosis suppresses the expression of inflammatory cytokines by evading the host immune response. MPT63/64-TBK1 decreased the secretion of IFN-β and increased the levels of TNF-α and IL-6 in proportion to the treatment concentration (FIG. 6E). Further, MPT63/64-TBK1 peptide reduced the amount of Mycobacterium tuberculosis in TBK$^{+/+}$ but not TBK$^{-/-}$.

From the above results, it may be seen that the MPT63/64-TBK1 peptide exhibits an antibacterial effect by reducing the expression of IFN-β and increasing the level of inflammatory cytokines.

4. Confirmation of ROS Level Increase and Mycobacterium tuberculosis Death Induction Effect of p47phox-Binding Peptide p47phox is an essential component for the activation of NADPH oxidase, which forms a complex with p22phox and p67phox. Activation of NADPH oxidase induces the production of reactive oxygen species (ROS) in cells, which are important for the immune response to the elimination of bacteria.

Figure 7A:
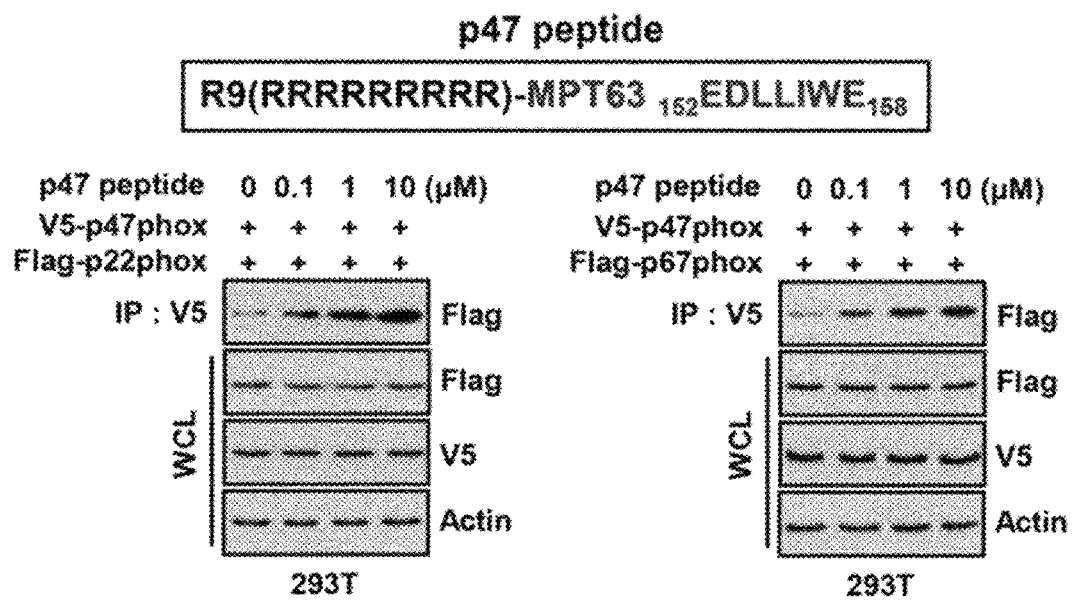
FIG. 7A shows the structure of p47 peptide including the region of MPT63 binding to p47phox (top) and the results of immunoprecipitation and Western blotting after 293T cells are transfected with V5-p47phox and Flag-p22phox or Flag-p67phox and treated with 1 μM p47 peptide for 6 hours (bottom)

To investigate the binding between p47phox and p22phox, a p47 peptide containing an amino acid interacting with MPT63 was prepared, and 293T cells were treated with V5-p47phox and Flag-p22phox or Flag-p67phox. The interaction between p47phox and p22phox or p67phox increased in proportion to the p47 peptide treatment concentration (FIG. 7A).

Figure 7B:
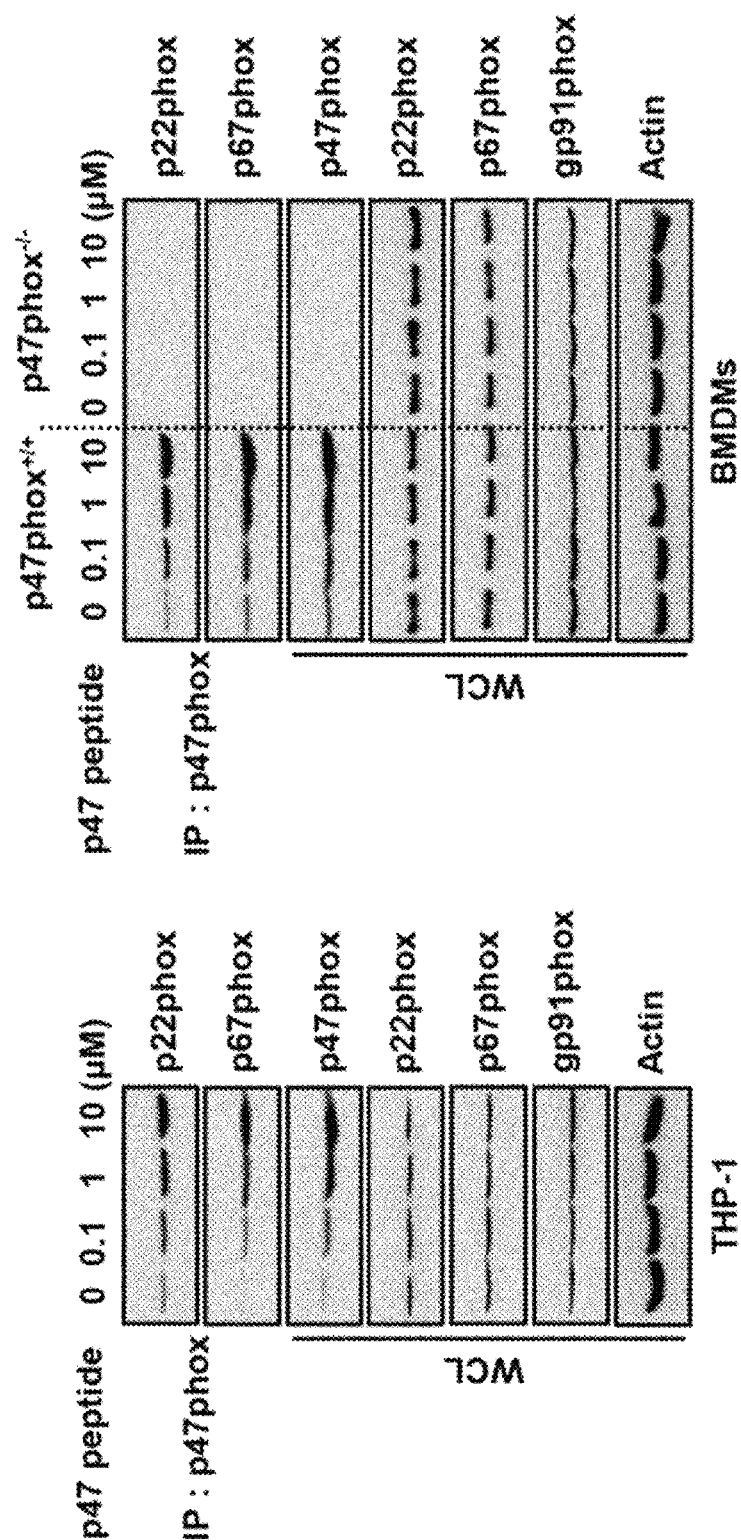
FIG. 7B shows the results of immunoprecipitation and Western blotting after 18 hours of treatment with p47 peptide at various concentrations in THP-1 cells and BMDM cells (p47phox$^{+/+}$ or p47phox$^{-/-}$)
Figure 7C:
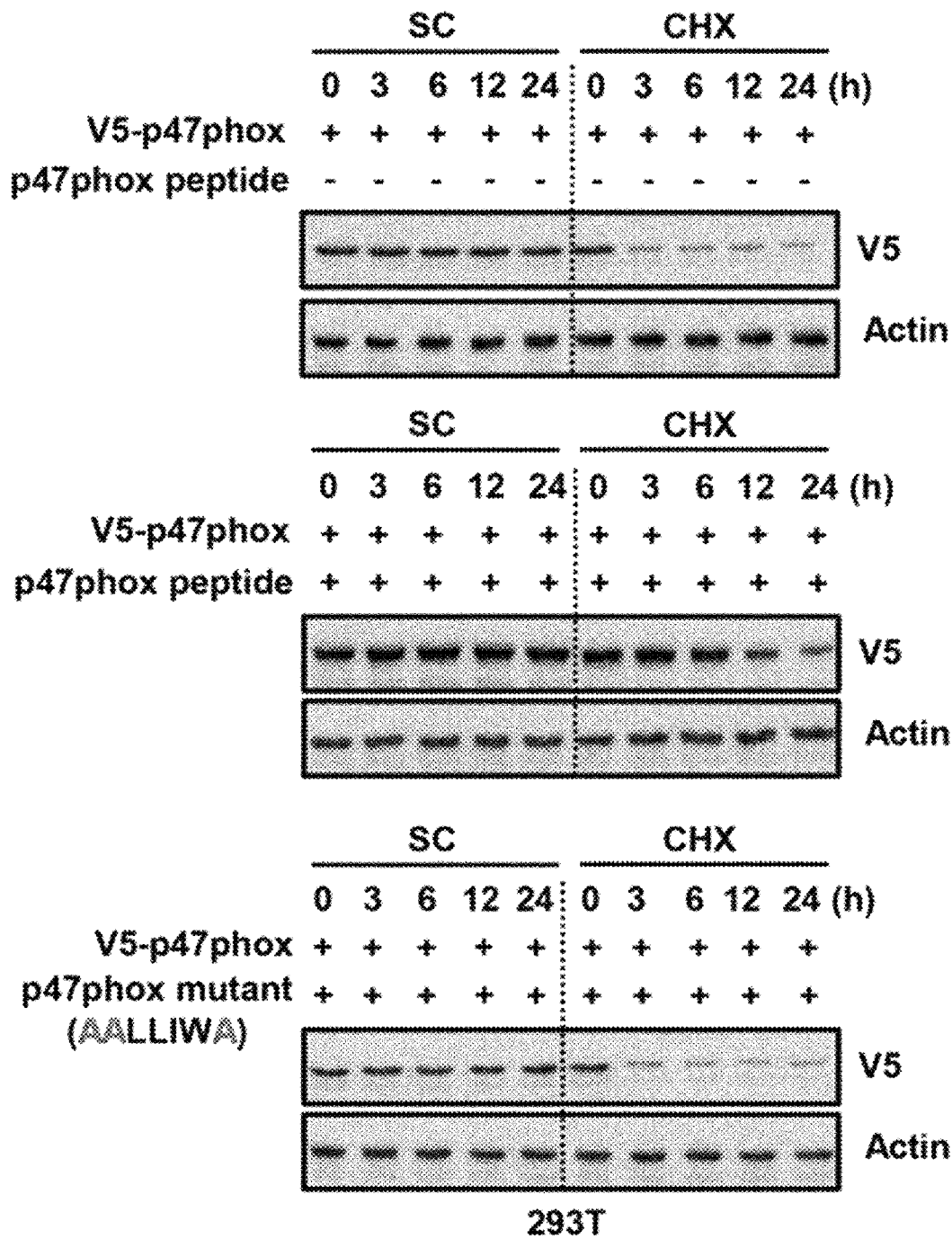
FIG. 7C shows the results of immunoprecipitation and Western blotting on cell lysates after 293T cells are transfected with V5-p47phox, treated with p47 peptide for 24 hours, and treated with SC (solvent control) or CHX (cycloheximide) at 1 μg/ml.

To confirm the endogenous binding between p47phox-p22phox-p67phox, THP-1 and BMDM were treated with p47 peptide, and co-immunoprecipitation was performed. Complex formation of p47phox-p22phox-p67phox was further increased in cells treated with high concentrations of p47 peptide, but not in p47phox$^{-/-}$ BMDM cells (FIG. 7B). Further, the stability of p47phox was increased according to p47 peptide treatment. However, the p47 mutant peptide in which the essential amino acids (E152, D153, and E158) were replaced with alanine did not enhance the stability of p47phox (FIG. 7C).

Figure 7D:
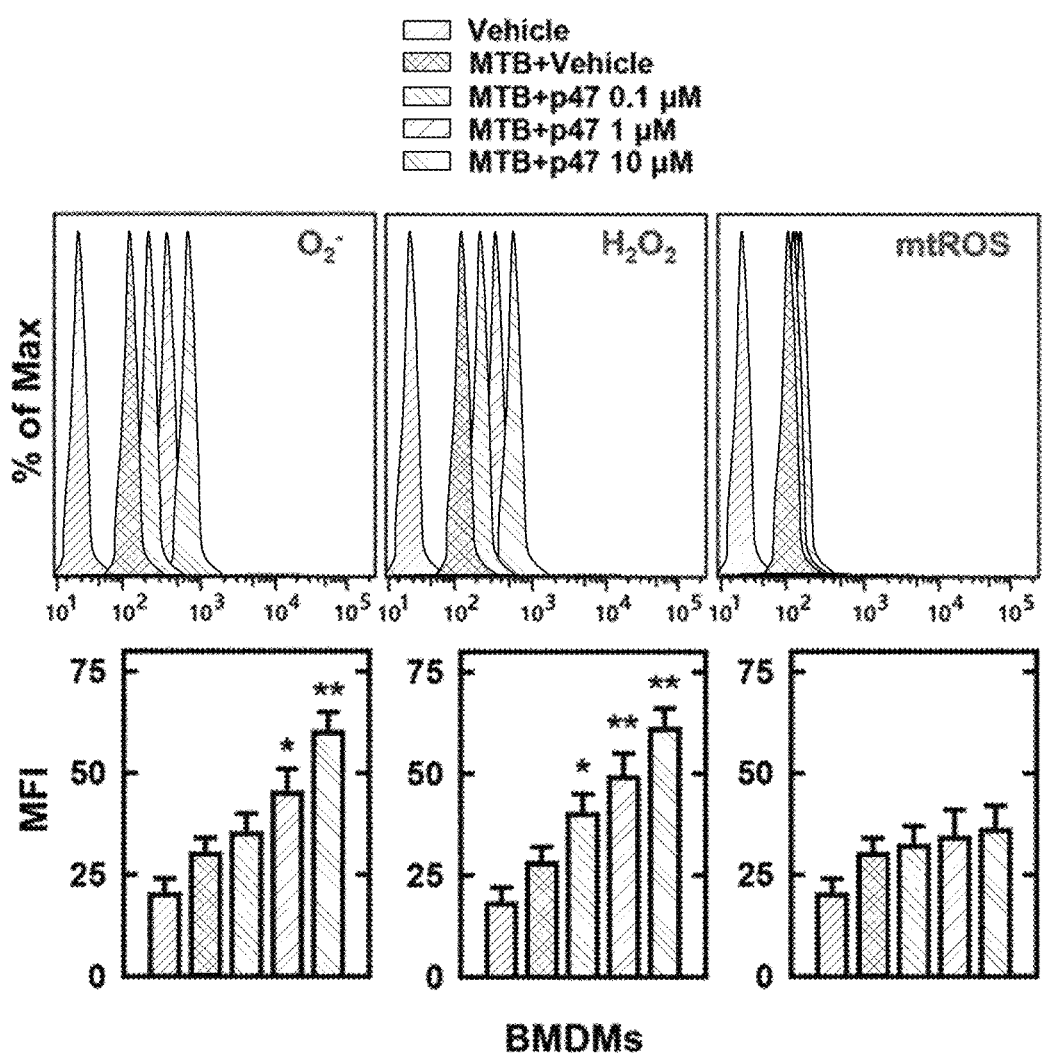
FIG. 7D shows the results of detecting $O_2^-$, $H_2O_2$ and mtROS by treating BMDM cells infected with *Mycobacterium tuberculosis* for 4 hours with Vehicle or p47 peptide at various concentrations for 18 hours.
Figure 7E:
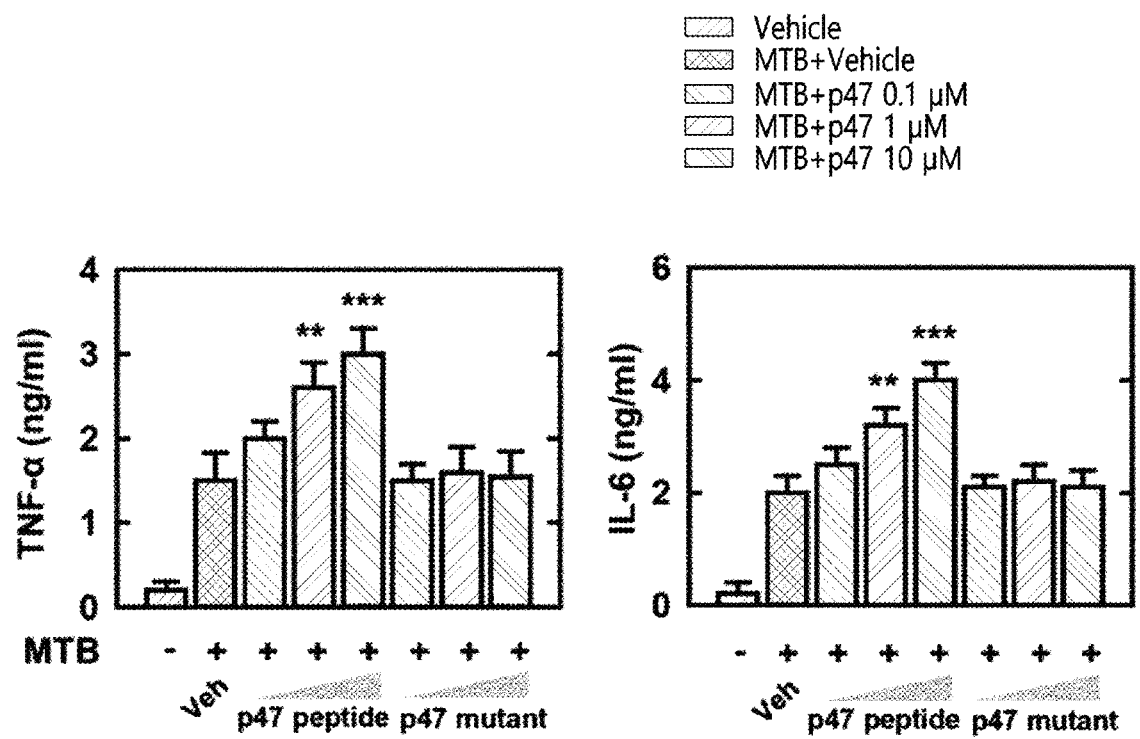
FIG. 7E shows the results of measuring the levels of TNF-α and IL-6 by treating BMDM cells infected with *Mycobacterium tuberculosis* with Vehicle or p47 peptides at various concentrations for 18 hours and performing ELISA.
Figure 7F:
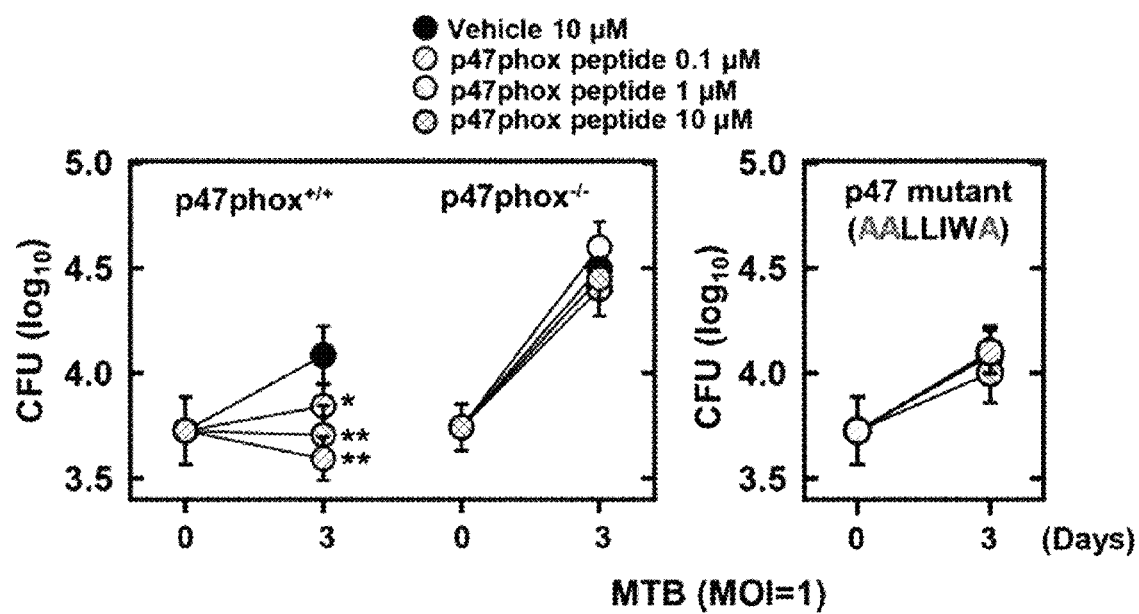
FIG. 7F shows the results of measuring the number of tuberculosis 3 days after treating BMDM cells infected with *Mycobacterium tuberculosis* with p47 peptide.

To investigate the role of MPT63 and p47phox in Mycobacterium tuberculosis infection, BMDM cells infected with Mycobacterium tuberculosis were treated with p47 peptide, and the levels of cellular or mitochondrial reactive oxygen species were measured. As a result, it was confirmed that the level of reactive oxygen species in cells increased in proportion to the p47 peptide treatment concentration, and it was confirmed that mitochondrial reactive oxygen species was not affected by the p47 peptide treatment (FIG. 7D). Further, the p47 peptide significantly increased TNF-α and IL-6 levels in Mycobacterium tuberculosis-infected macrophages, but these results were not induced by the p47 mutant peptide (FIG. 7E). The amount of intracellular Mycobacterium tuberculosis decreased proportionally with the high concentration of p47 peptide treatment (FIG. 7F).

Through the above results, it may be seen that the p47 peptide enhances the interaction between p47phox-p22phox-p67phox, thereby increasing the levels of reactive oxygen species and inflammatory cytokines and inducing the death of Mycobacterium tuberculosis.

5. Confirmation of Binding of HK2 Peptide to Macrophages Infected with Mycobacterium tuberculosis HK2 plays an essential role in glycolysis by converting D-glucose into α-D-glucose-6-phosphate. Glycolysis is closely related to inflammation and is known as immune metabolism. Previous studies have shown that HK2 accumulates within the inflammatory environment so as to activate immune responses. Through this, it is to confirm the binding of HK2 and HK2 peptides in macrophages infected with Mycobacterium tuberculosis.

Figure 8A:
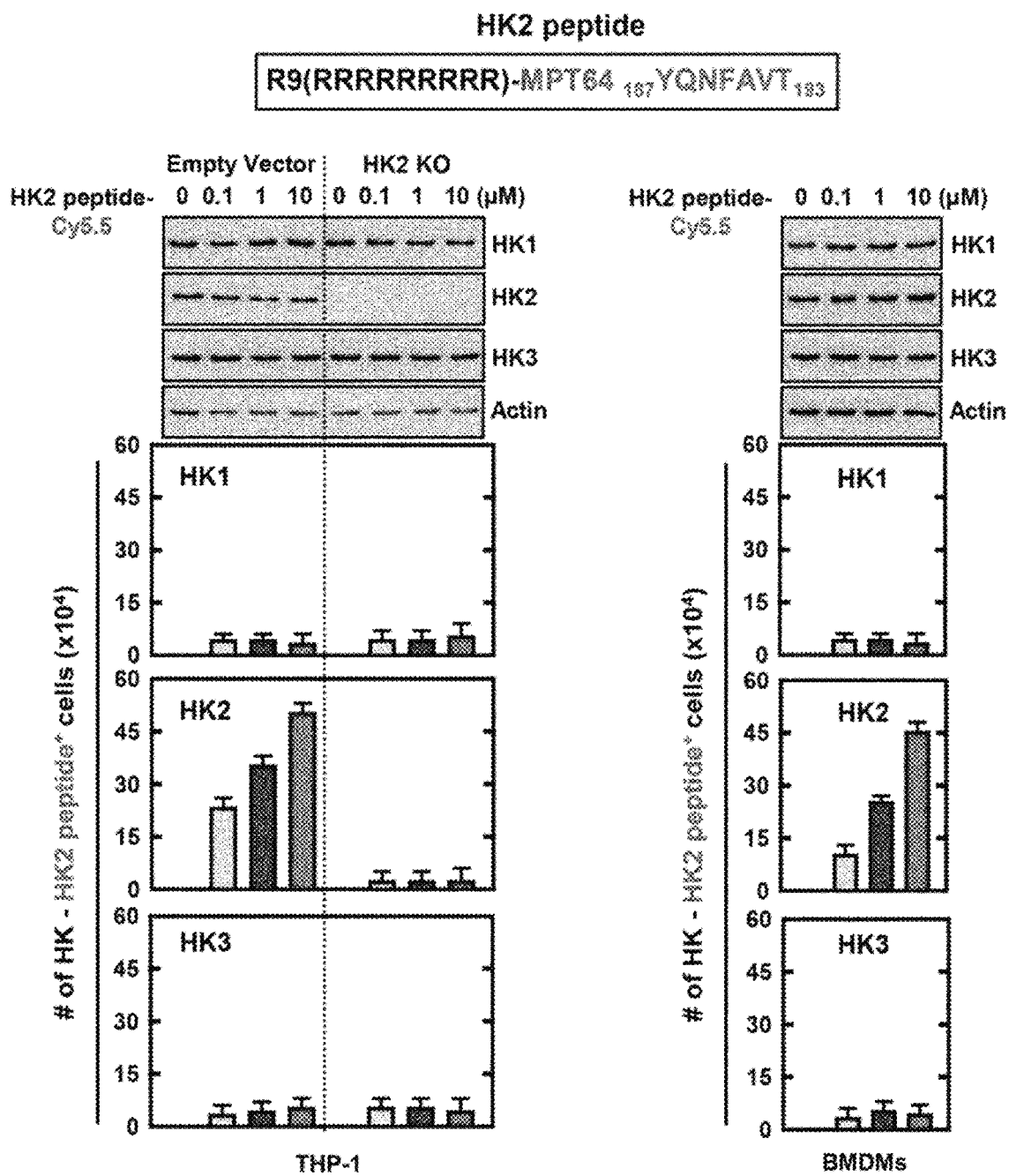
FIG. 8A shows the structure of the HK2 peptide including the region of MPT64 binding to HK2 (top), the results of immunoprecipitation of THP-1 cells (Empty vector or HK2 Knock-out) and BMDM cells treated with Cy5.5-labeled HK2 peptide at various concentrations for 1 hour and the results of counting HK-HK2 peptide+ cells by performing FACS (bottom)

An HK2 peptide containing an MPT64 domain that interacts with HK2 was constructed. To investigate the interaction between the prepared HK2 peptide and HK2, Cy5.5-labeled HK2 peptide$^+$ cells were counted using flow cytometry. As a result, in macrophages, HK2 peptide only interacted with HK2, but did not interact with HK1 and HK3 (FIG. 8A).

Figure 8B:
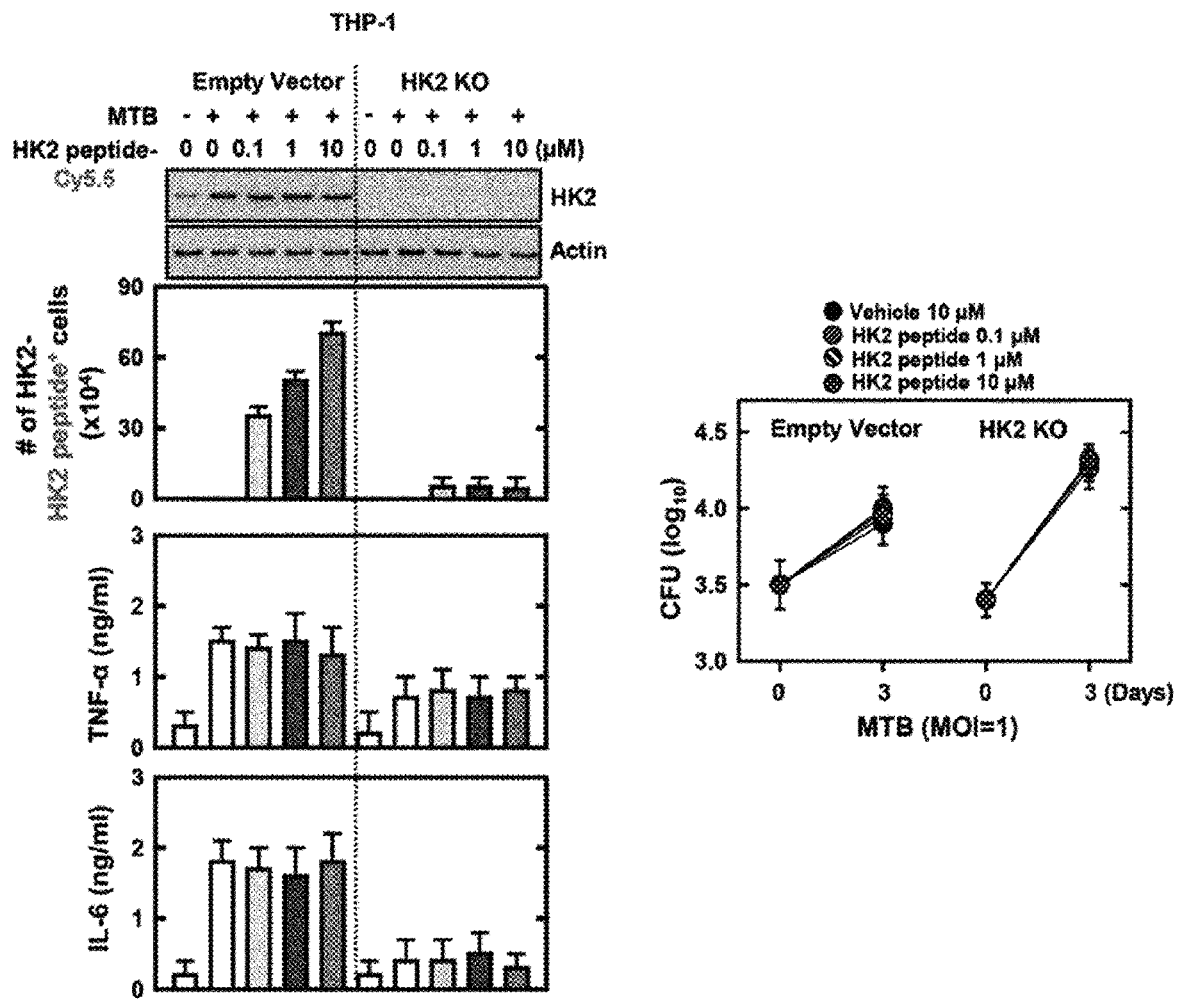
FIG. 8B shows the results of counting HK-HK2 peptide+ cells by immunoprecipitation and FACS after THP-1 cells (Empty vector or HK2 Knock-out) are infected with *Mycobacterium tuberculosis* for 4 hours, treated with Cy5.5-labeled HK2 peptide at various concentrations for 1, 18, or 72 hours, and 1 hour later (top left), a result of measuring the levels of TNF-α and IL-6 in the THP-1 cell supernatant treated with HK2 peptide for 18 hours by performing ELISA (bottom left) and a result of measuring CFU of *Mycobacterium tuberculosis* in *Mycobacterium tuberculosis*-infected THP-1 cells treated with HK2 peptide at various concentrations after 3 days (right)

In order to investigate the effect of the HK2 peptide on Mycobacterium tuberculosis infection, macrophages infected with Mycobacterium tuberculosis were treated with HK2 peptide. As a result, HK2 peptide treatment did not significantly affect the expression of inflammatory cytokines and the number of Mycobacterium tuberculosis (FIG. 8B).

Figure 8C:
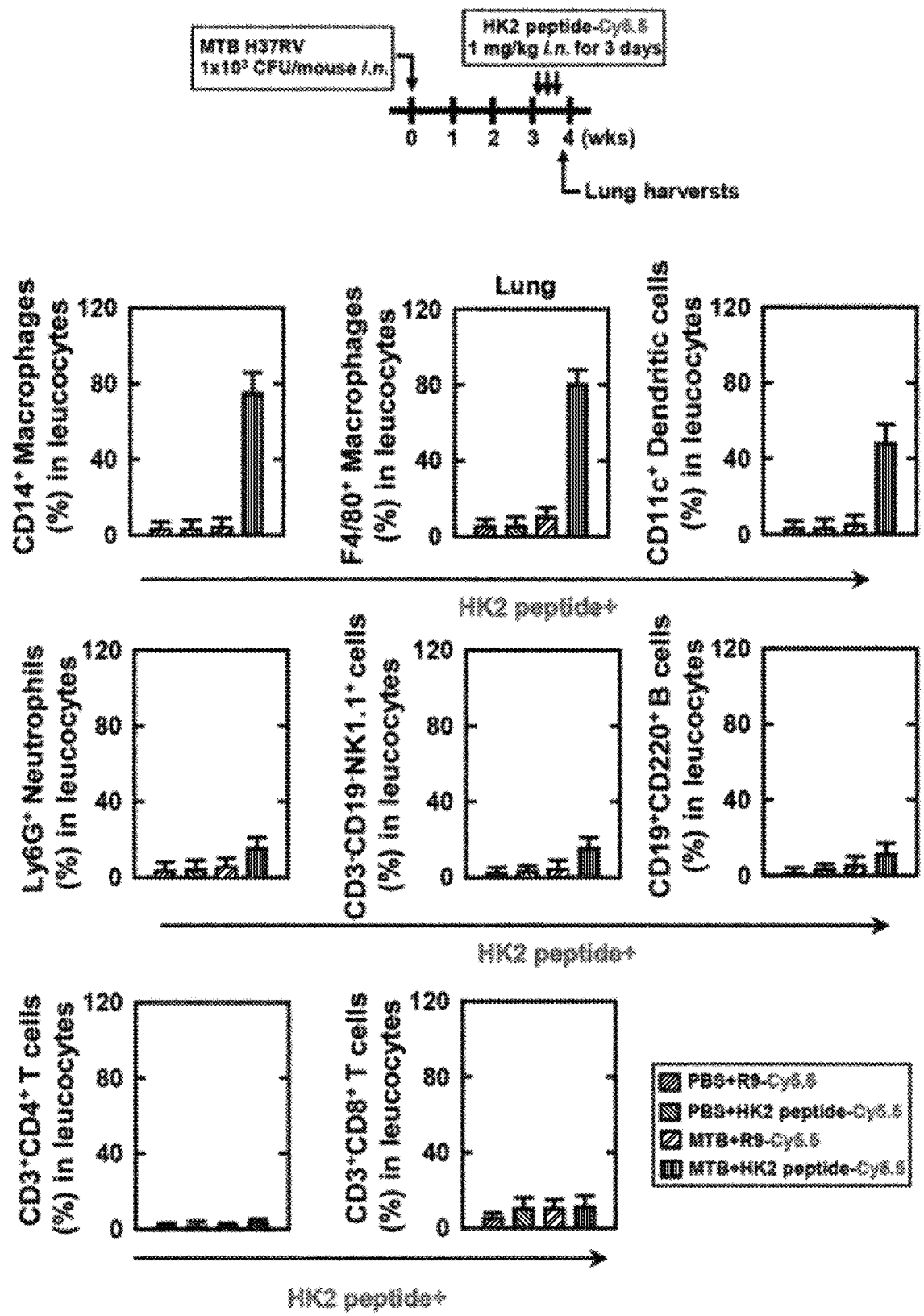
FIG. 8C shows the results of counting HK2 peptide+ cells from the lungs by performing FACS after Cy5.5-labeled HK2 peptide (1 mg/kg) is intranasally administered to mice intranasally infected with *Mycobacterium tuberculosis* (1×10$^3$/per mice) for 3 weeks.

In order to evaluate the specificity of the HK2 peptide, mice infected with Mycobacterium tuberculosis were administered the HK2 peptide via intranasal injection. HK2 targets macrophages in the lungs infected with Mycobacterium tuberculosis, but not other immune cells (FIG. 8C).

From the above results, it may be seen that HK2 specifically binds to Mycobacterium tuberculosis-infected macrophages to target Mycobacterium tuberculosis-infected macrophages.

6. rMPT Design, Construct, and Confirmation of its Antibacterial Activity

Figure 9B:
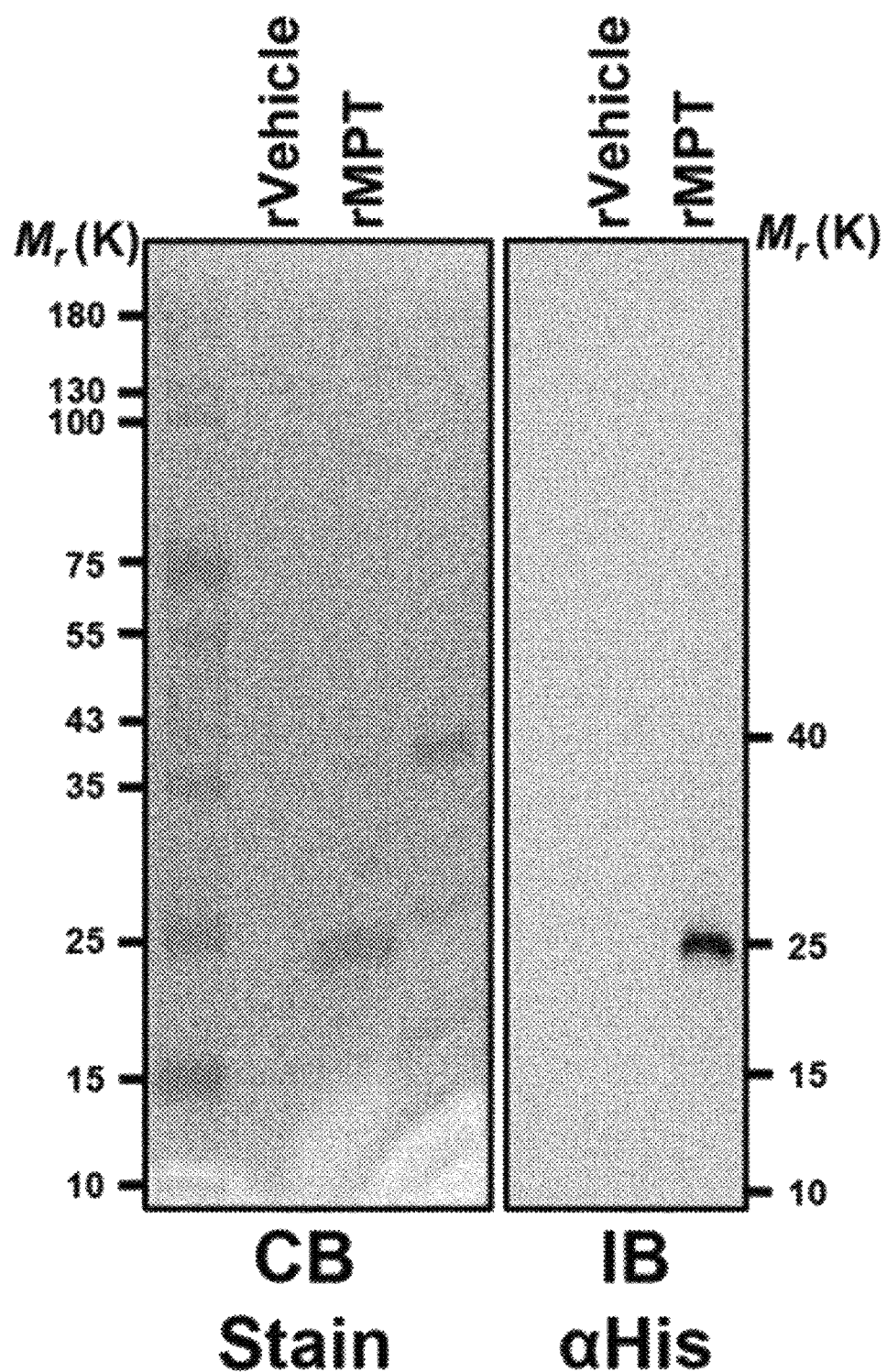
FIG. 9B is a diagram showing results of coomassie blue staining (left) and western blotting (right) on rMPT prepared from bacteria purified by 6×His.

Previous results showed that TBK1 and p47 peptides increased the expression of inflammatory cytokines and mycobactericidal activity in macrophages. Further, it was confirmed that the HK2 peptide specifically interacts with HK2 of *Mycobacterium tuberculosis*-infected macrophages to increase the targeting efficiency of *Mycobacterium tuberculosis*-infected macrophages. In order to generate proteins containing the respective functions of TBK1, p47 and HK2 peptides, a multifunctional recombinant MPT protein (rMPT) containing multiple nucleotide sequences of TBK1, p47 and HK2 peptides was designed. This was confirmed using SDS-polyacrylamide gel electrophoresis and immunoblotting (FIGS. 9A and 9B).

Figure 9C:
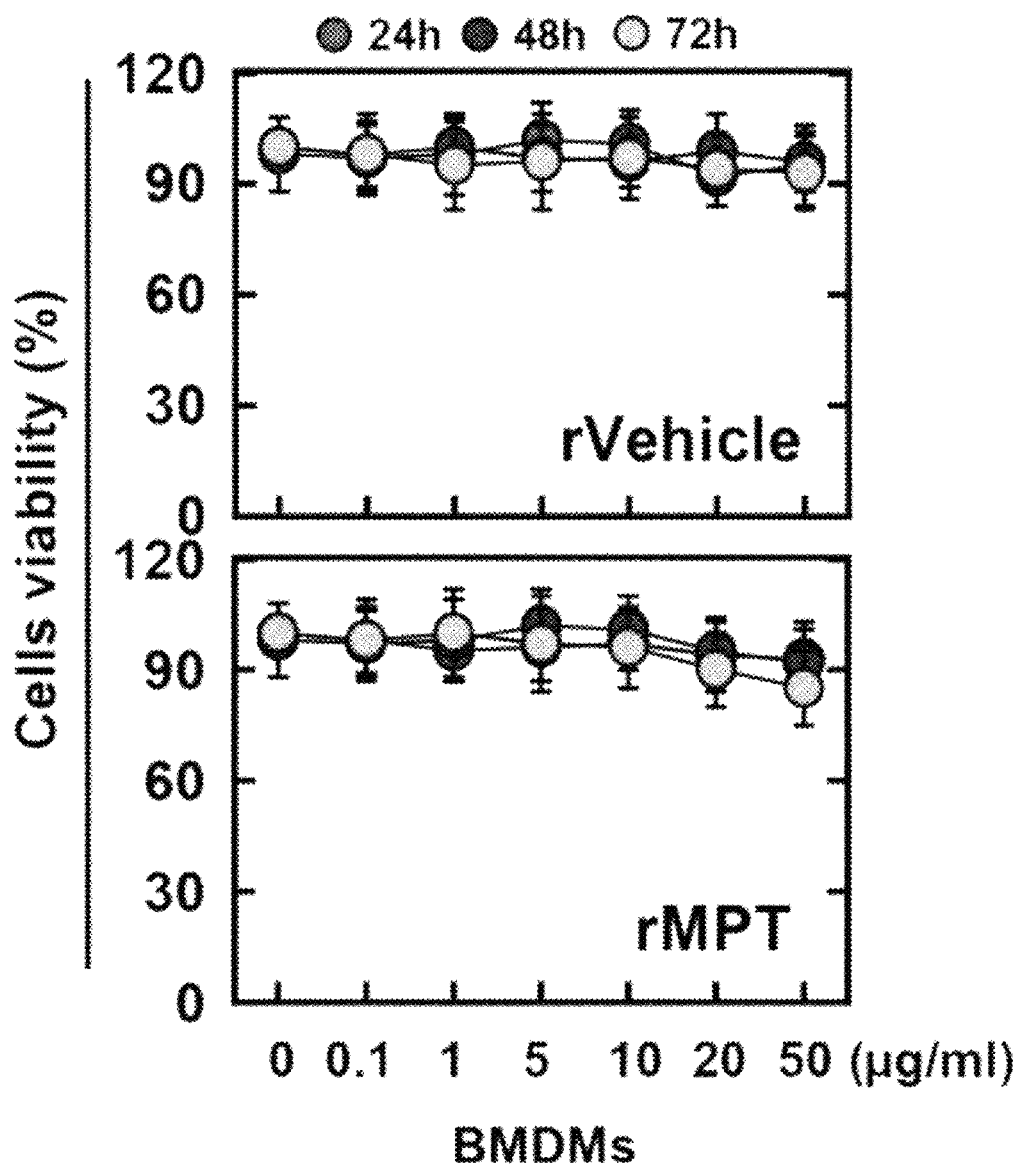
FIG. 9C is a result of confirming the cell viability by treating BMDM cells with rVehicle and rMPT and performing MTT analysis in order to confirm the cytotoxicity of rMPT.
Figure 9D:
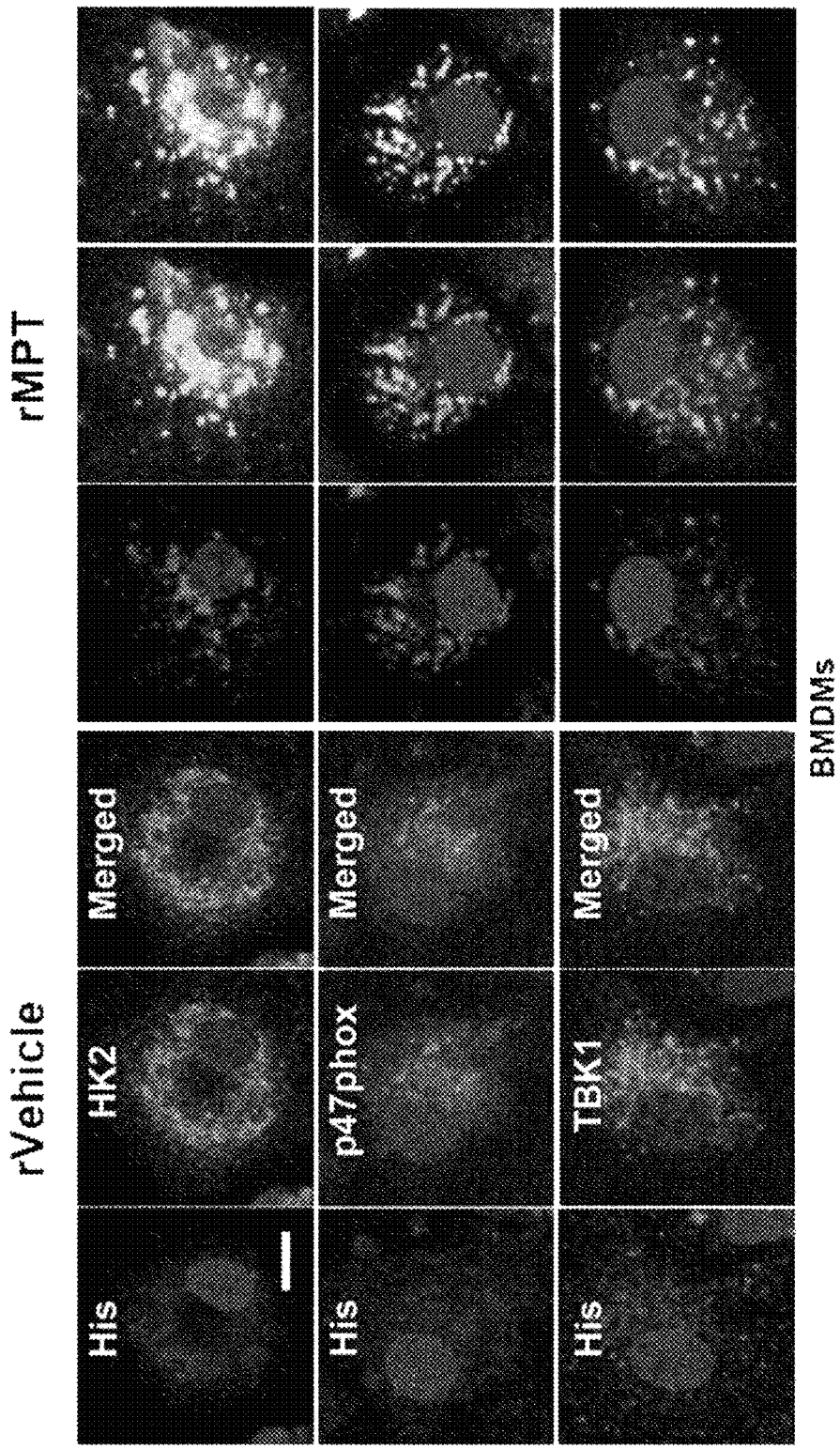
FIG. 9D is a diagram illustrating BMDM treated with rVehicle or rMPT and immunolabeled with αHis (Alexa 586), αHK2, αp47phox, αTBK1 (Alexa 488) and DAPI.
Figure 9E:
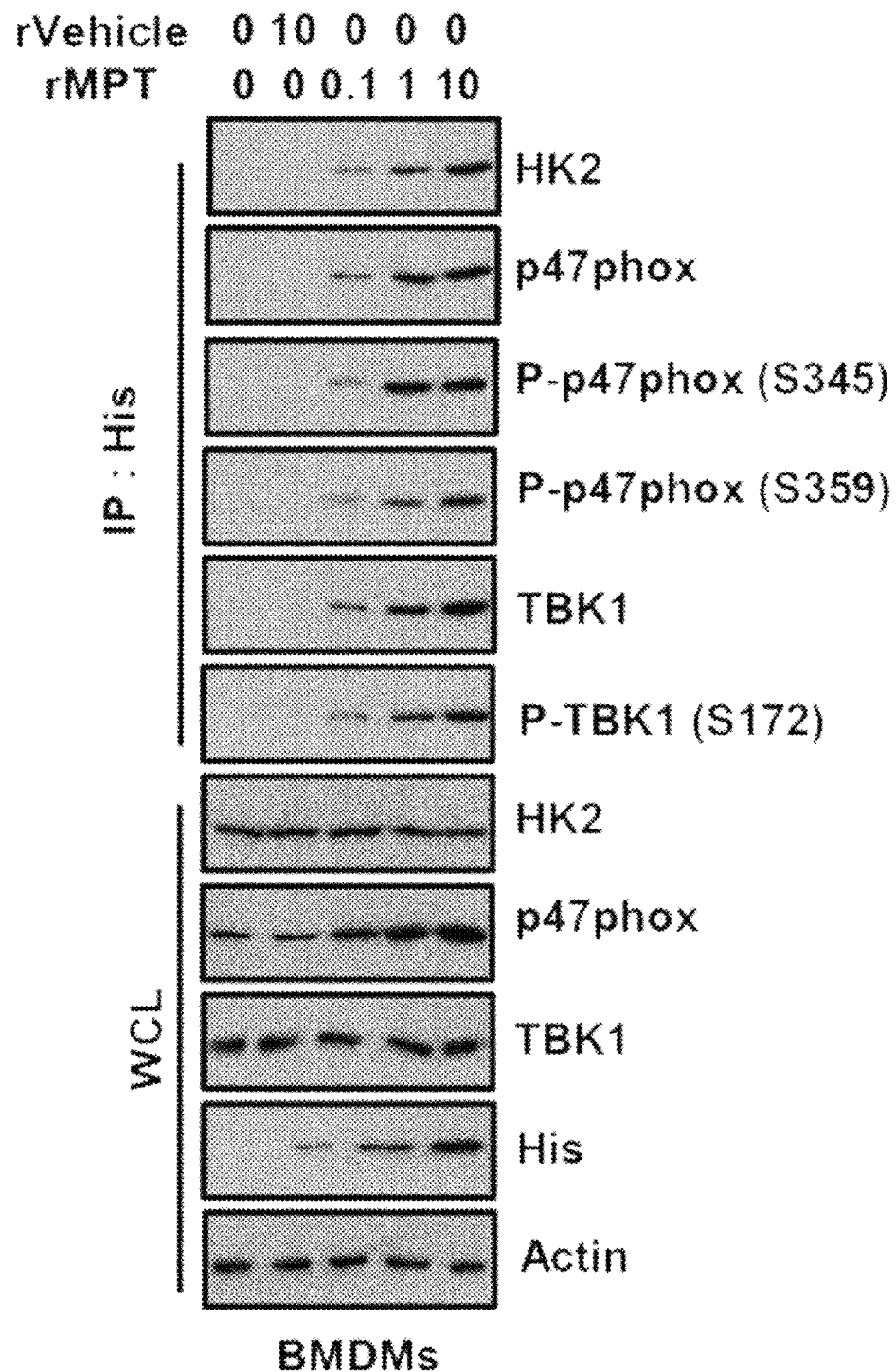
FIG. 9E shows the results of immunoprecipitation of BMDM cells treated with rVehicle or rMPT for 1 hour with αHis and Western blotting with αHK2, αp47phox, αP-p47phox (S345 and S359), αTBK1, and αP-TBK1 (S172)
Figure 9F:
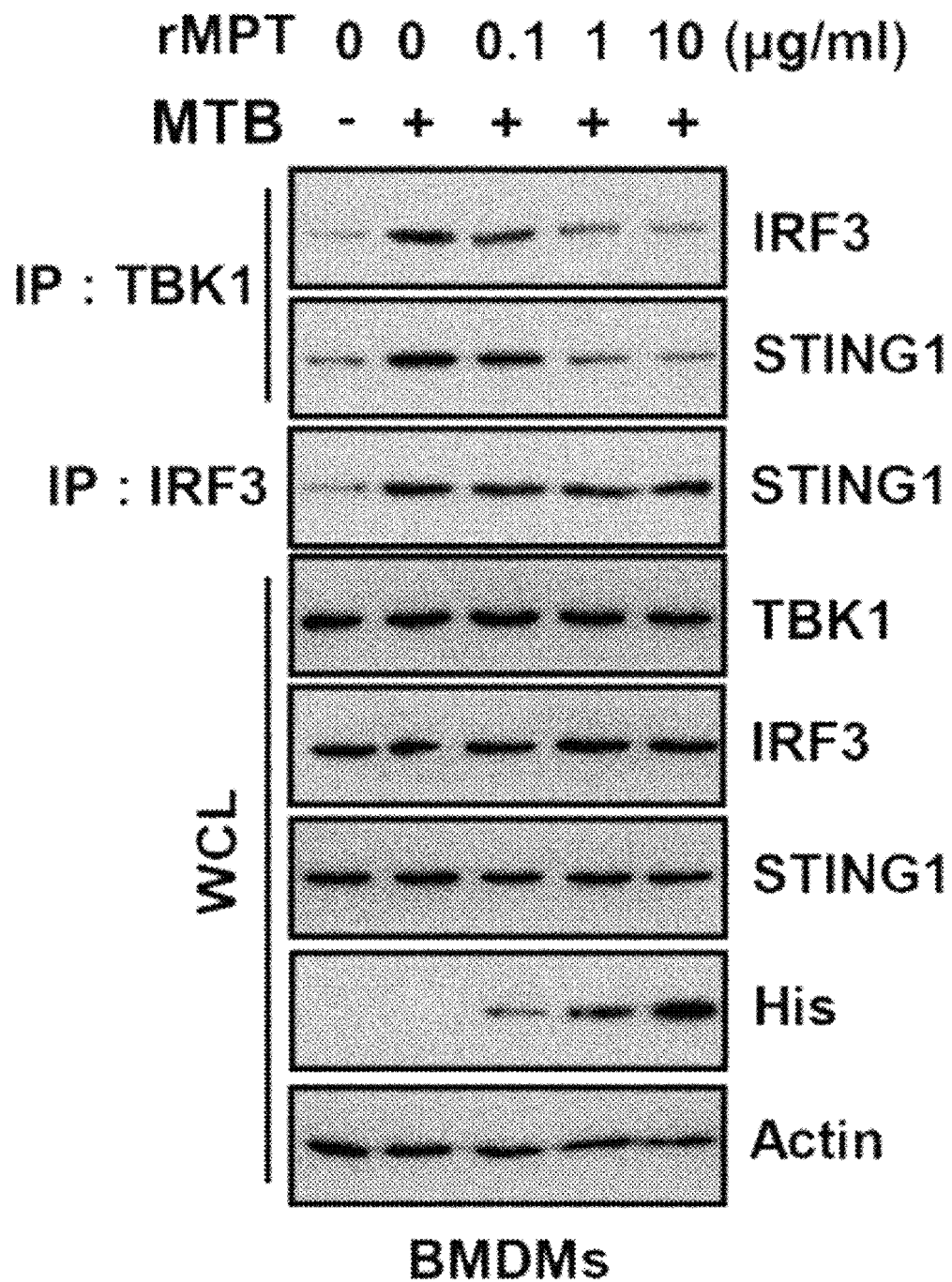
FIG. 9F shows the results of immunoprecipitation with αTBK1 and αIRF3, and Western blotting with αIRF3 and αSTING1 after BMDM cells infected with *Mycobacterium tuberculosis* for 4 hours are treated with rMPT at various concentrations for 1 hour.
Figure 9G:
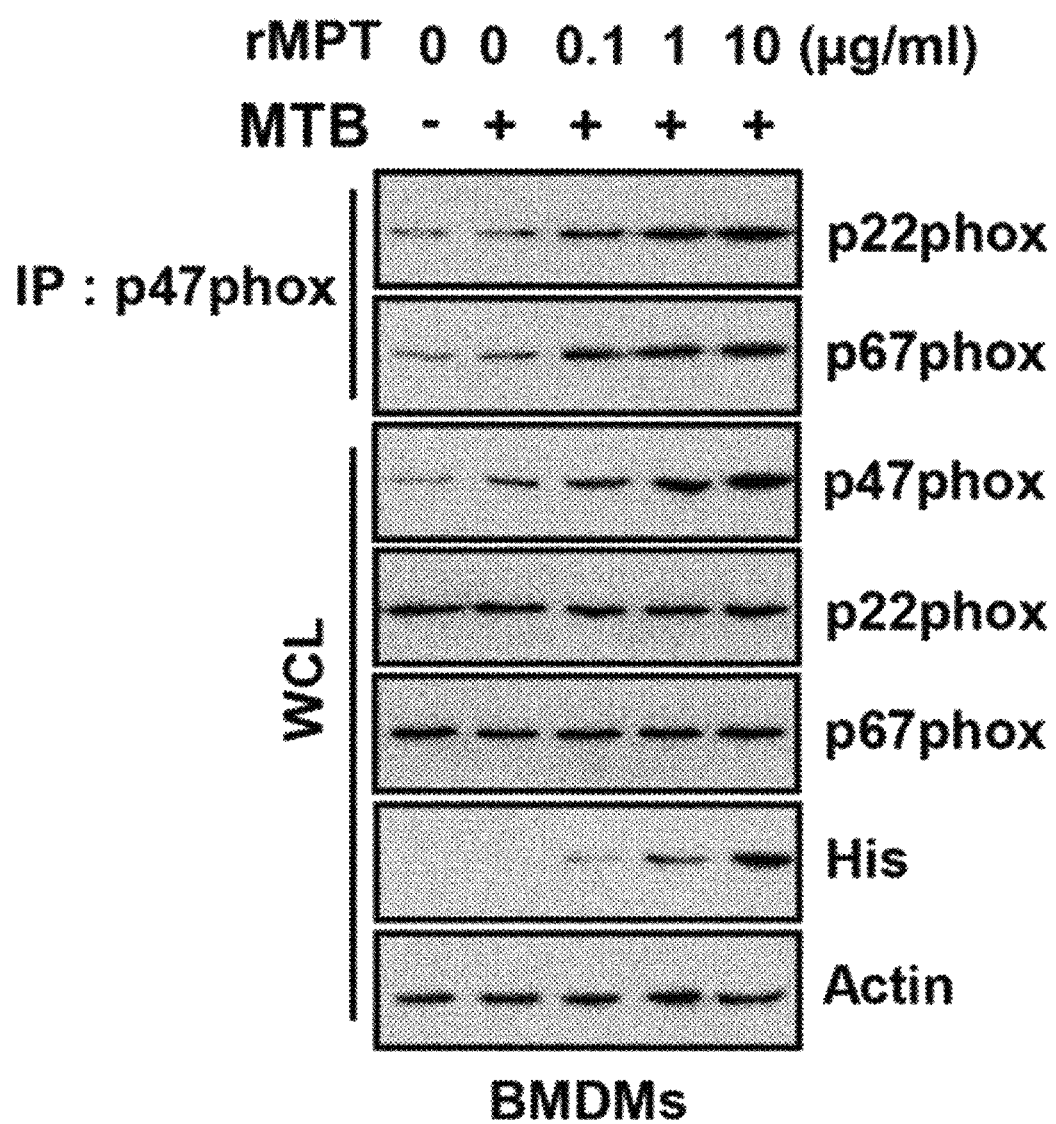
FIG. 9G shows the results of immunoprecipitation with αap47phox, and Western blotting with αp47phox, αp22phox, αp67phox, αHis and αActin after BMDM cells infected with *Mycobacterium tuberculosis* for 4 hours are treated with rMPT at various concentrations for 1 hour.
Figure 9H:
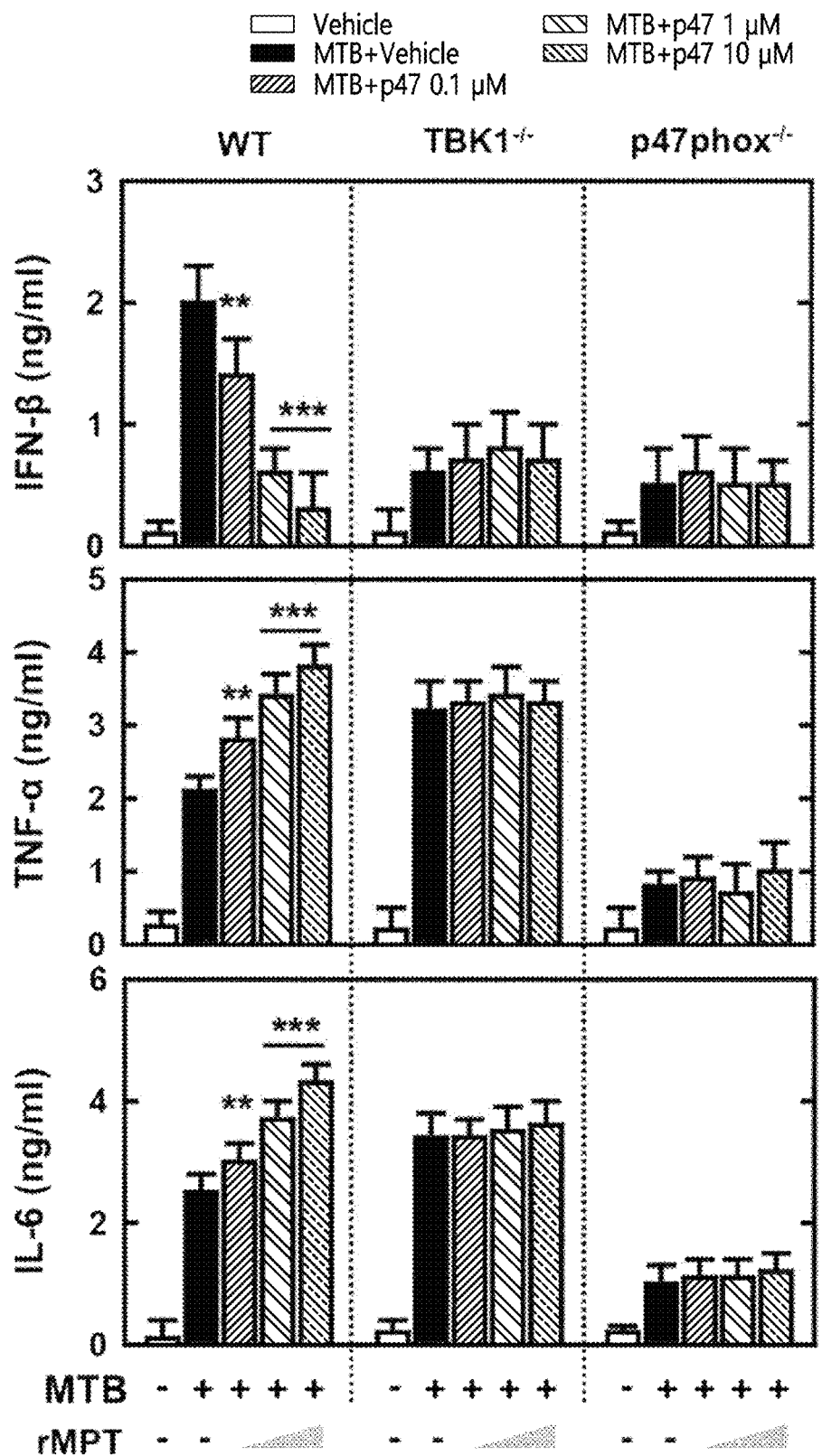
FIG. 9H shows the results of measuring the levels of IFN-β, TNF-α and IL-6 contained in the cell supernatant by performing ELISA after WT, TBK$^{-/-}$, or p47phox$^{-/-}$ BMDM cells were infected with *Mycobacterium tuberculosis* for 4 hours, treated with rMPT at various concentrations for 18 hours.
Figure 9I:
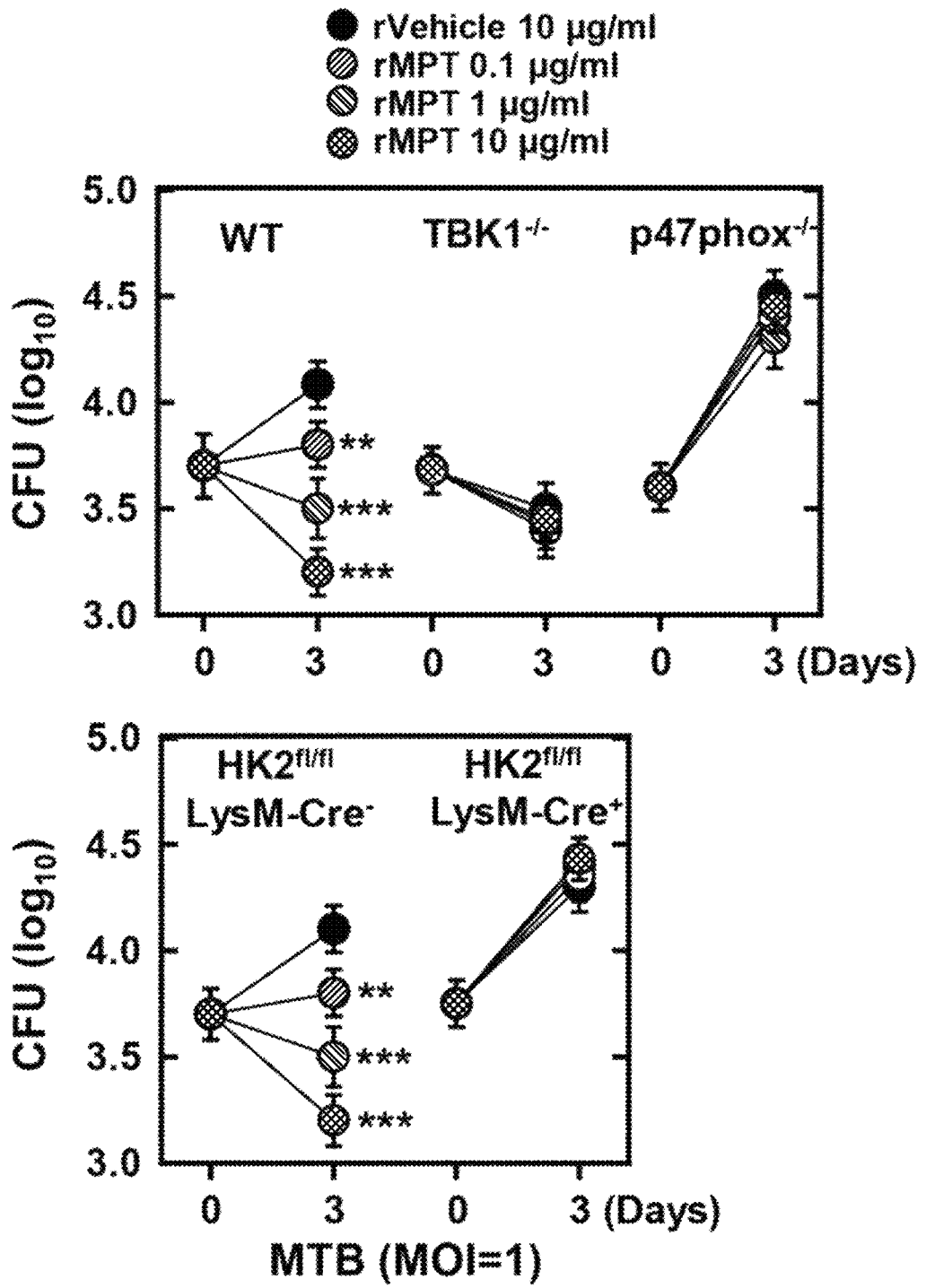
FIG. 9I shows the results of measuring the number of intracellular bacteria 3 days after treatment with rVehicle or rMPT in WT, TBK$^{-/-}$ or p47phox$^{-/-}$ (top) and HK2$^{fl/fl}$ LysM-Cre$^-$ or HK2$^{fl/fl}$ LysM-Cre+ BMDM.

As a result of confirming the cytotoxicity of rMPT, the cytotoxicity of rMPT in BMDM cells was not significantly different from that of the empty vector (FIG. 9C). Subsequently, in order to confirm location of MPT and binding partner, BMDM was treated with rVehicle or rMPT, and the results were observed with fluorescence images. As a result, rMPT was co-located with HK2, p47phox and TBK1 in BMDM (FIG. 9D). Further, it was confirmed that rMPT interacted with HK2, p47phox and TBK1 in a concentration-proportional manner. It may be seen that the phosphorylated form of p47phox (S345 and 5359) or TBK1 (S172) was also related to the interaction with rMPT (FIG. 9E). In macrophages infected with *Mycobacterium tuberculosis*, as shown in FIGS. 3C and 3D results, the STING1-TBK1-IRF3 complex was continuously reduced by rMPT (FIG. 9F), and after rMPT treatment, the synthesis of the p47phox-p22phox-p67phox complex was increased (FIG. 9G). Further, rMPT decreased the secretion of IFN-β in wild-type BMDM cells, in contrast to TNF-α and IL-6. In BMDM of mice not expressing TBK1$^{-/-}$ and p47phox$^{-/-}$ or HK2, there was no significant difference in the expression of the inflammatory cytokines according to the rMPT treatment (FIG. 9H). The number of *Mycobacterium tuberculosis* was reduced in wild-type macrophages according to the rMPT treatment, but no difference was found in the number of bacteria in BMDM of mice that did not express TBK1$^{-/-}$, p47phox$^{-/-}$ or HK2 (FIG. 9I).

From the above results, it may be seen that rMPT may reduce the number of *Mycobacterium tuberculosis* by interacting with HK2, p47phox and TBK1 and activating the inflammatory response.

7. Confirmation of Vaccine Effect of rMPT In Vivo

BCG vaccine is important for the prevention of tuberculosis, but BCG vaccine is weak in adult pulmonary tuberculosis. Therefore, urgent is the development of potential vaccine candidates.

Figure 10A:
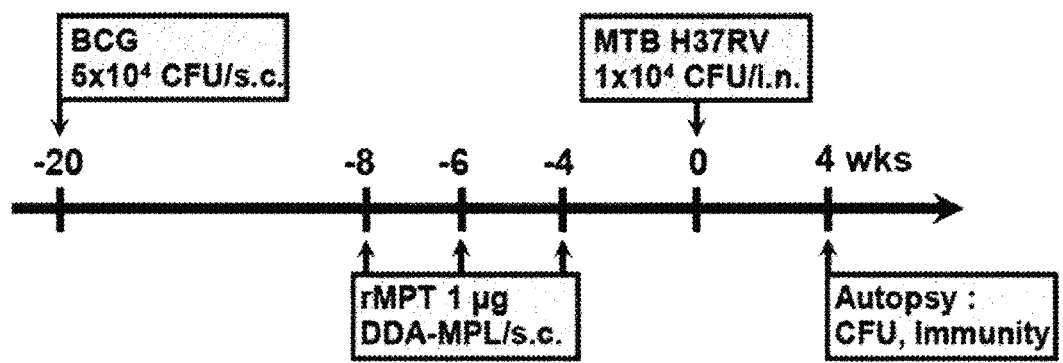
FIG. 10A is a schematic diagram of a vaccine test model treated with rMPT, each mouse (n=10 per group) is immunized with BCG via subcutaneous injection for 12 weeks prior to vaccination with rMPT (1 µg). Before aerosol infection with *Mycobacterium tuberculosis* H37Rv, rMPT and DDA-MPL (adjuvant) are injected three times subcutaneously, and immunological analysis is performed after 4 weeks.
Figure 10B:
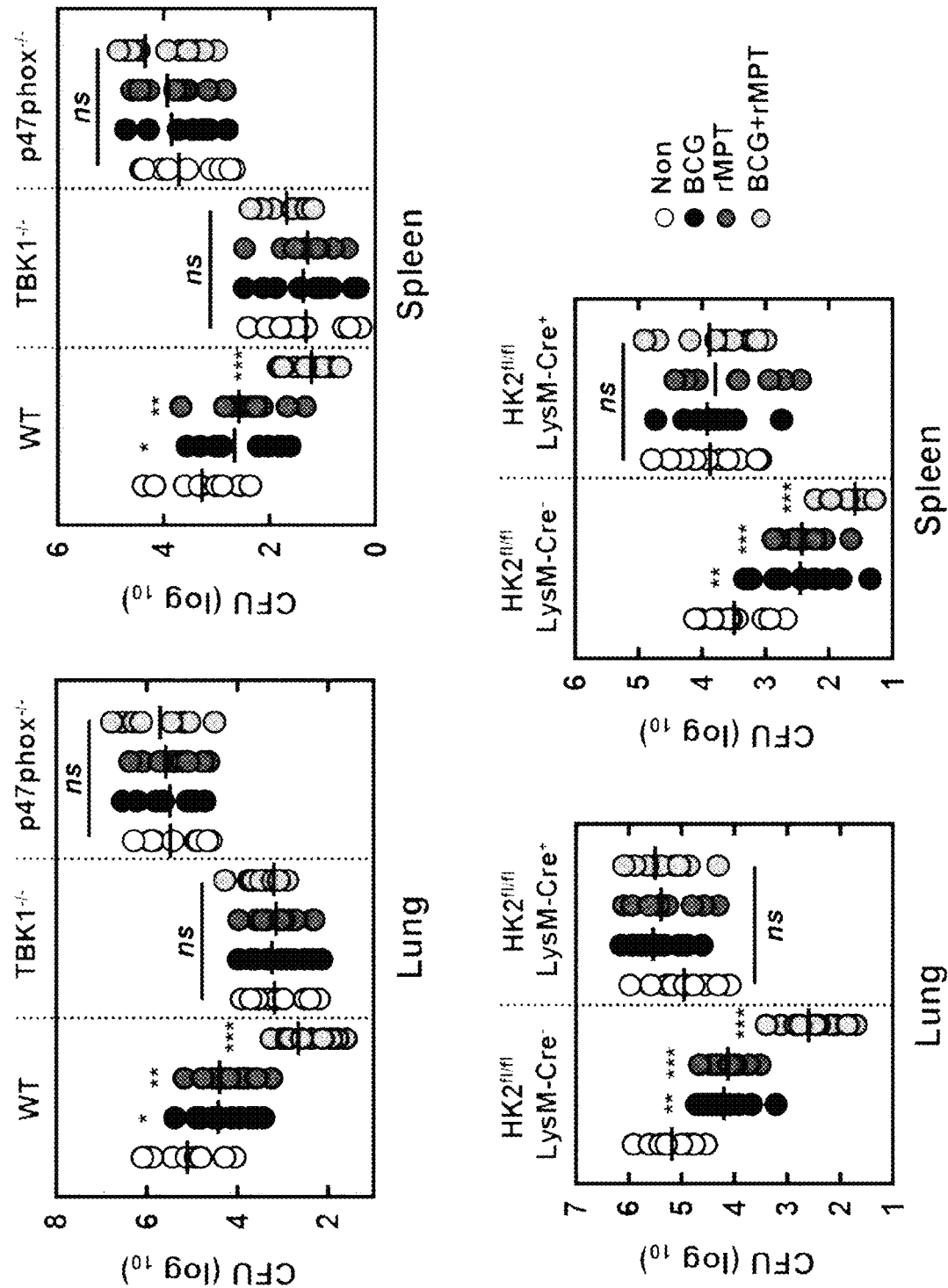
FIG. 10B shows the results of measuring the CFU of the lungs and spleen of all groups 4 weeks after infection.

In order to confirm the tuberculosis prevention effect of rMPT, BCG-administered mice were treated with rMPT in combination with DDA-MPL adjuvant. After vaccination, mice were infected with *Mycobacterium tuberculosis* via intranasal injection (FIG. 10A). As a result, the number of *Mycobacterium tuberculosis* was reduced in the lungs and spleen except for the untreated wild-type mouse group, and in particular, a significant decrease was confirmed in the mice that were simultaneously inoculated with BCG and rMPT. Meanwhile, deficiency of TBK1, p47phox, or HK2 had no effect on the tuberculosis prevention effect of rMPT (FIG. 10B).

Figure 10C:
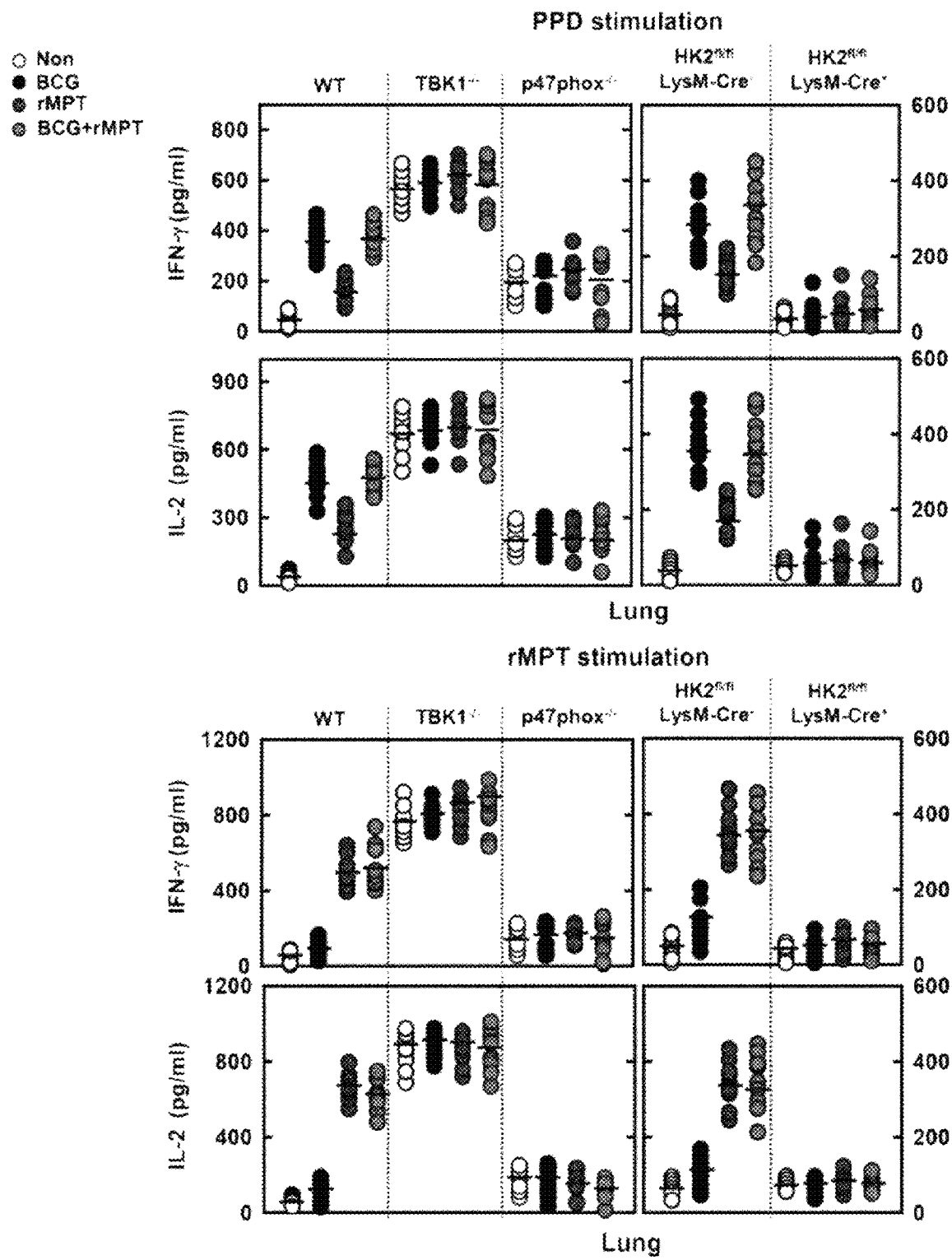
FIG. 10C shows the results of measuring the levels of IFN-γ and IL-2 in the supernatant by performing ELISA after all groups of mice are sacrificed 4 weeks after infection, and lung harvests are obtained and stimulated with purified proteins derivative (PPD, 10 µg/ml) or rMPT (0.1 µg/ml) from each group.

In order to investigate reactivation of acquired immunity due to rMPT, lung cells were restimulated in vitro with purified proteins derivative (PPD) or rMPT. It was confirmed that when treating with PPD, no immune activity was observed in lung cells vaccinated with rMPT, but the immune response was activated by PPD in lung cells vaccinated with BCG or BCG and rMPT treatment. In contrast to lung cells vaccinated with BCG, lung cells vaccinated with rMPT had an activated immune response upon rMPT restimulation (FIG. 10C).

From the above results, it may be seen that rMPT increases the preventive effect on tuberculosis and the reactivation of the acquired immune system.

Figure 11A:
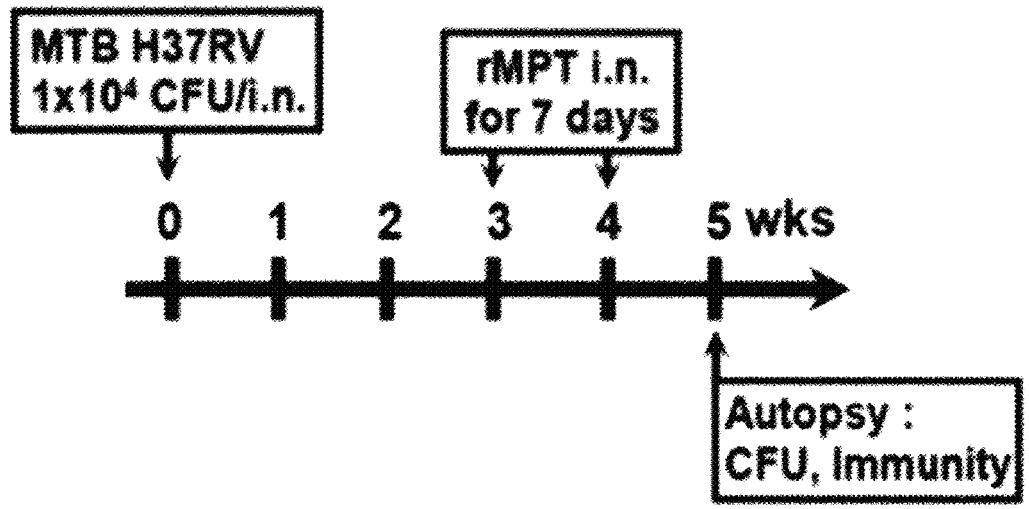
FIG. 11A is a schematic diagram of a tuberculosis model treated with rMPT or rVehicle, mice (n=10 per group) are intranasally infected with *Mycobacterium tuberculosis* H37Rv (1×10$^4$ CFU/mouse), mice are treated with rMPT or rVehicle for 7 days 3 weeks after infection, and then the immunological analysis is performed 5 weeks later.
Figure 11B:
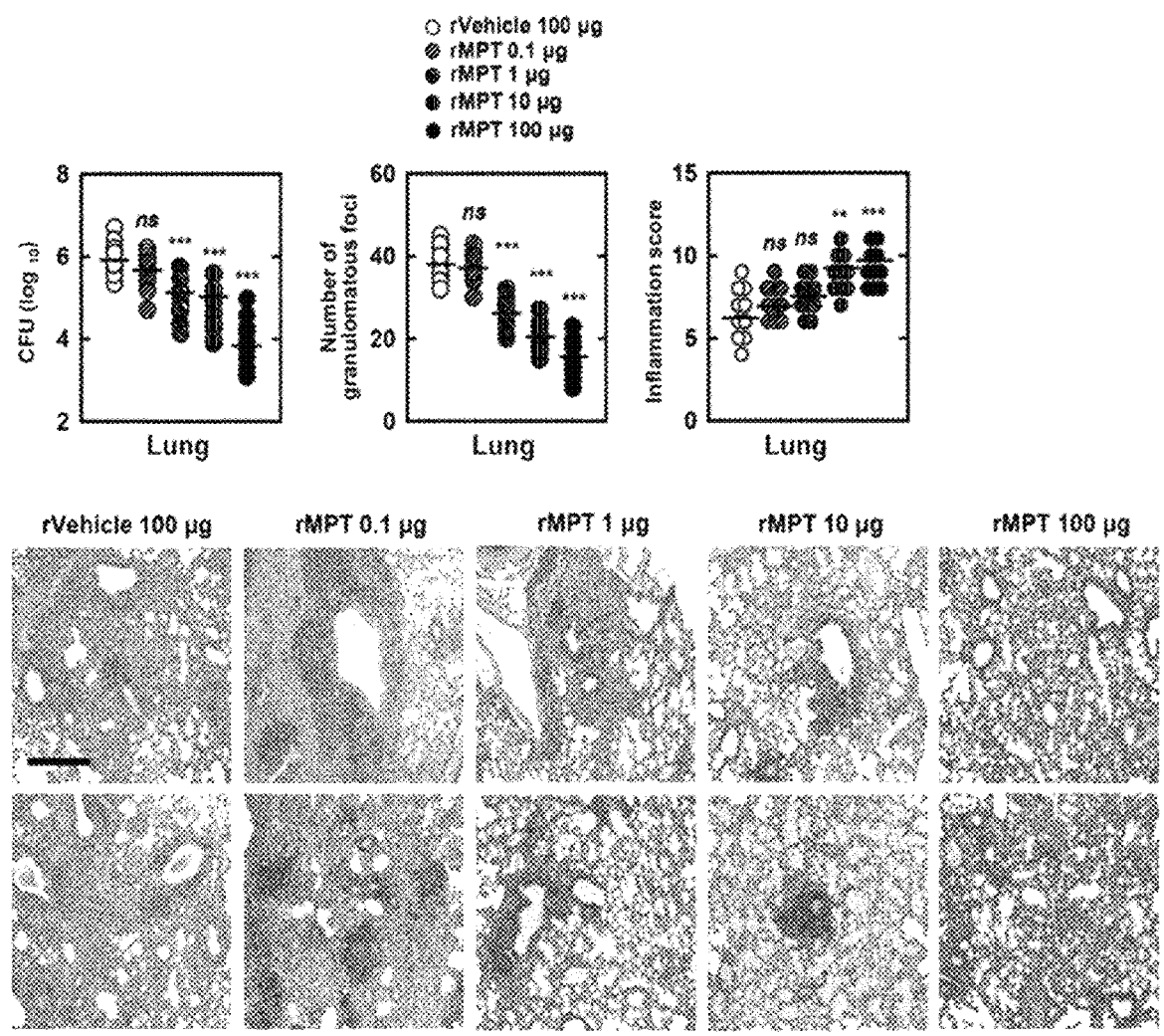
FIG. 11B shows the results of analyzing the number of bacteria, granulomas, and inflammation levels in the mouse lungs of each group (top) and H&E staining of the lung tissue (bottom)
Figure 11C:
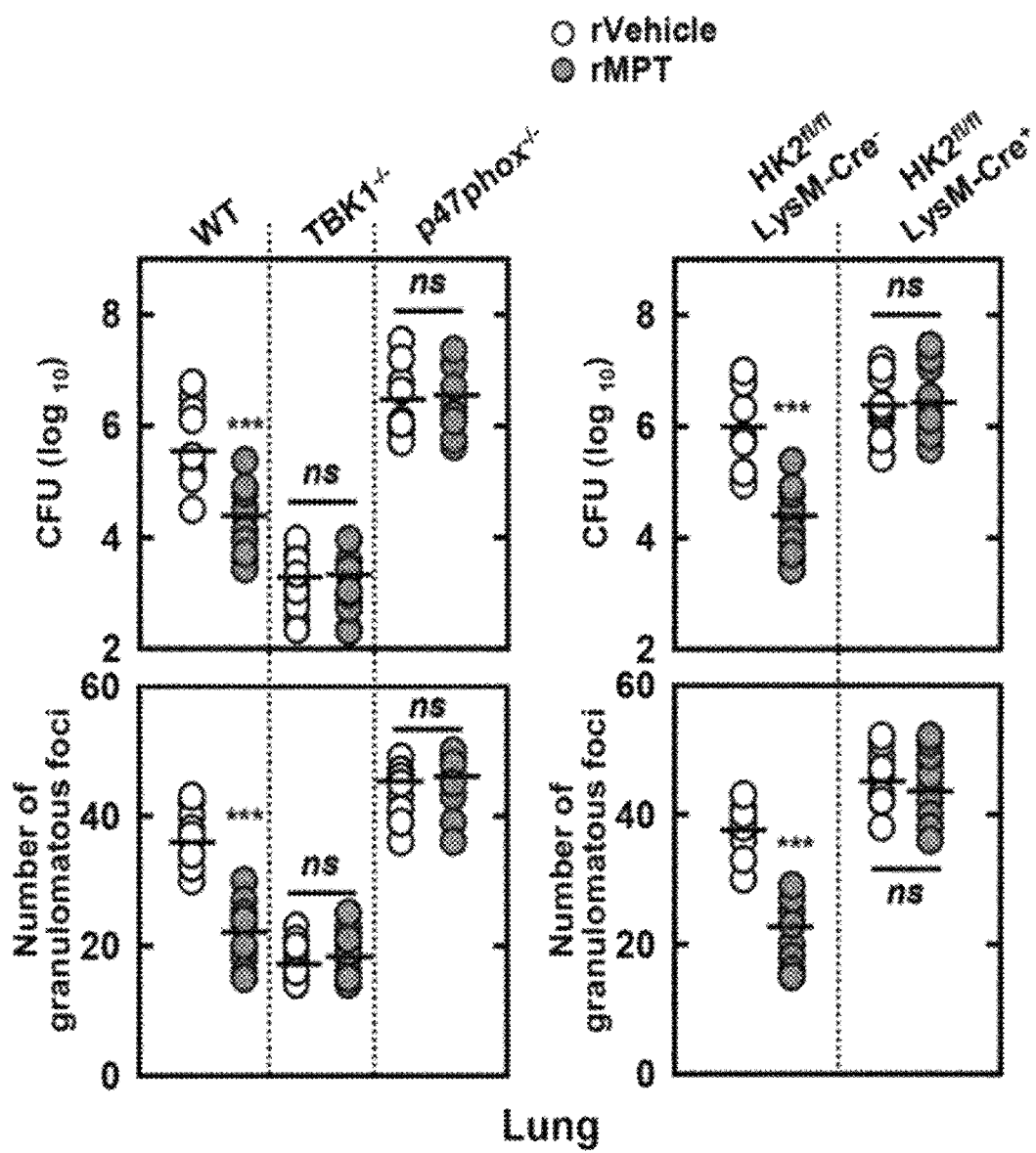
FIG. 11C shows the results of measuring the number of bacteria and granulomas in the lungs of WT, p47phox$^{-/-}$, HK2$^{fl/fl}$ LysM-Cre$^-$, and HK2$^{fl/fl}$ LysM-Cre+ mice.
Figure 11D:
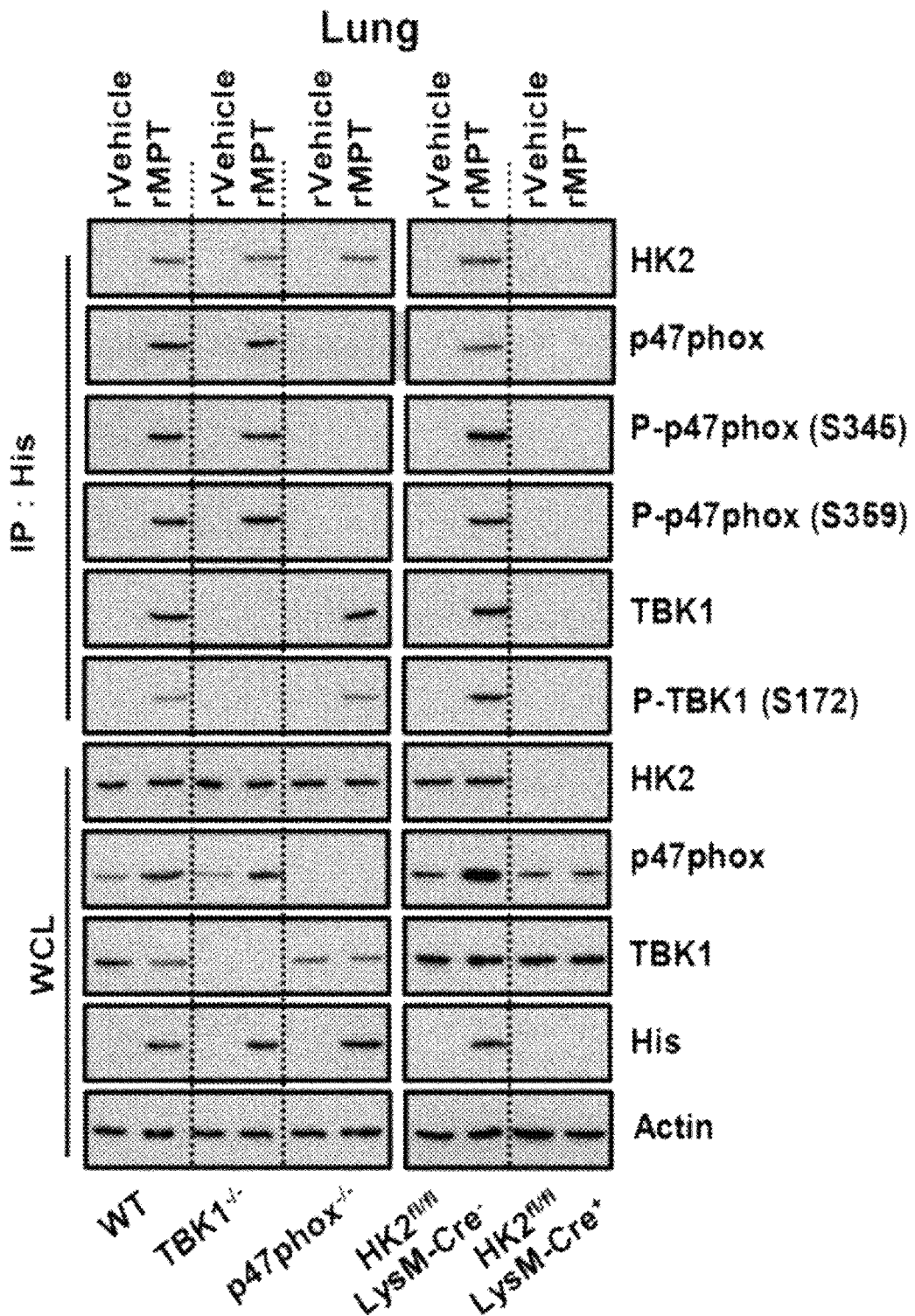
FIG. 11D shows the results of immunoprecipitation of lung harvests from mice of each group with His-agarose beads, followed by western blotting with αHK2, αp47phox, αP-p47phox (S345 and S359), αTBK1 and αP-TBK1 (S172), and cell lysates are used for Western blotting with αHK2, αp47phox, αTBK1, αHis and αActin.
Figure 11E:
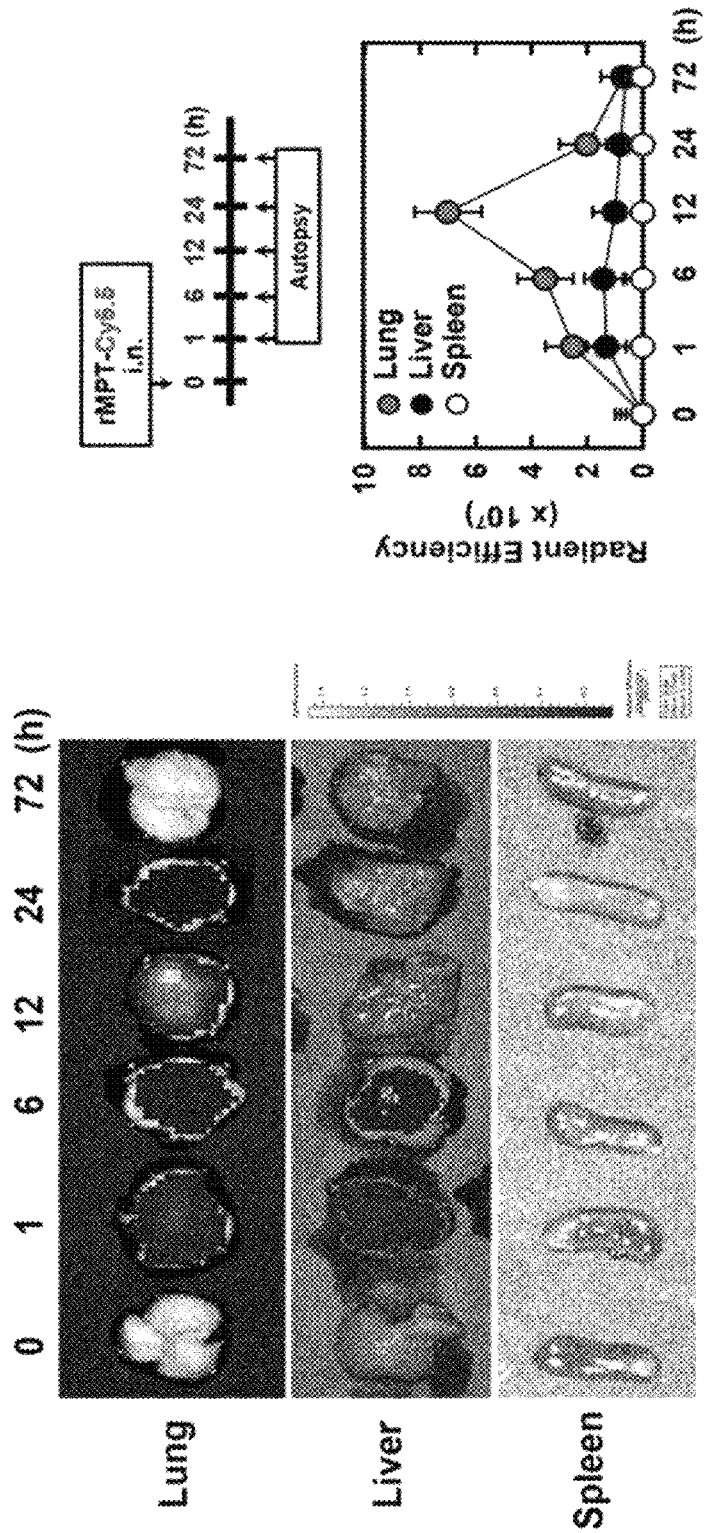
FIG. 11E is fluorescence images of the lungs, liver, and spleen of mice intranasally administered with Cy5.5-labeled rMPT (left), and a graph of quantifying the fluorescence intensity of each organ with the IVIS spectrum-chromatography (CT) system (right)
Figure 12:
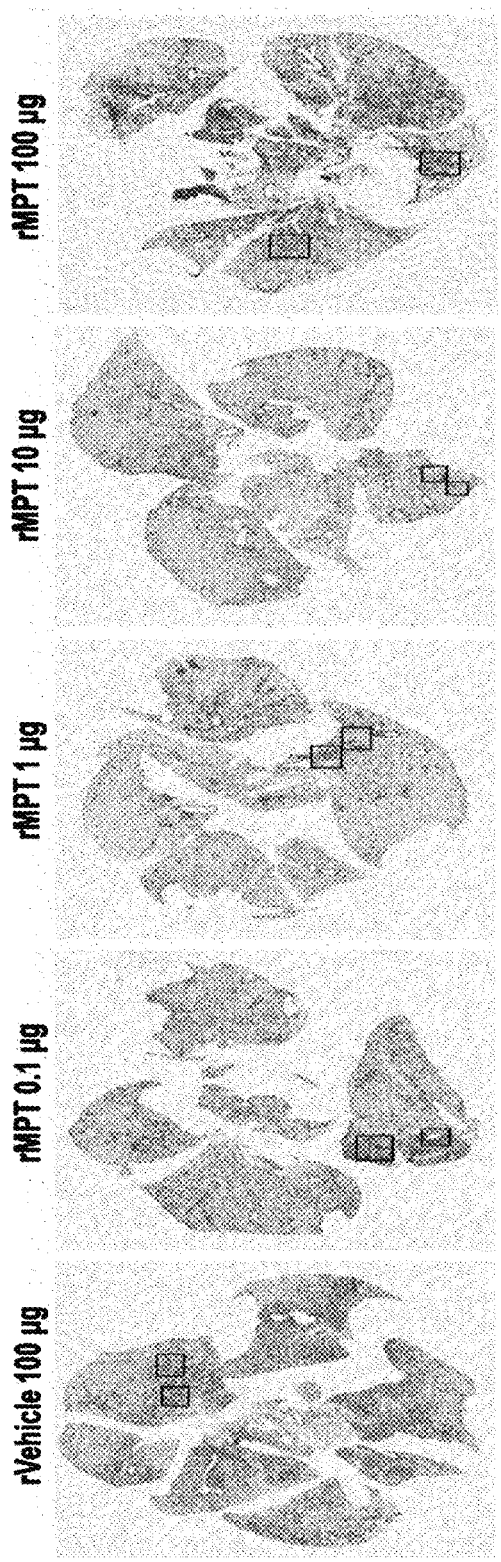
FIG. 12 shows the results of H&E staining of mouse lung sections of each group.

8. Confirmation of *Mycobacterium tuberculosis* Death-Inducing Effect of rMPT In Vivo In order to determine whether rMPT increases the anti-tuberculosis effect in mice, the mice were infected with the H37Rv *Mycobacterium tuberculosis* strain through intranasal injection, and the treatment was performed by intranasal administration of rMPT (FIG. 11A). First, the number of intracellular bacteria was confirmed, and the pathology of the lungs was evaluated. In the case of rMPT-treated mice, the number of bacteria was reduced, and the infiltration of immune cells and lung damage were reduced (FIGS. 11B and 12). Colony-forming unit (CFU) and granulomas were reduced in rMPT-treated mice. However, this difference was not significant in mice deficient in TBK1, p47phox or HK2 compared to the control group (FIG. 11C). Consistent with the results in FIG. 6E, rMPT was associated with TBK1, p47phox and HK2 in the lungs of mice infected with *Mycobacterium tuberculosis* (FIG. 11D). Further, the biological distribution and pharmacokinetics of rMPT in mice were measured using an in vivo imaging system (IVIS) spectrum-chromatography (CT) system. rMPT accumulated in the lungs and spleen within 1 hour. Further, rMPT was excreted within 6 hours in the liver, whereas it was maintained for 24 hours in the lungs.

From the above results, it may be seen that rMPT increases the antibacterial effect by interacting with TBK1, p47phox and HK2 in mice infected with *Mycobacterium tuberculosis*.

As described above, specific parts of the present disclosure have been described in detail. It is apprehended for those of ordinary skill in the art that these specific descriptions are only preferred embodiments, and the scope of the present disclosure is not limited thereby. Accordingly, the substantial scope of the present disclosure is defined by the appended claims and their equivalents.

What is claimed is:

1. A recombinant MPT protein,
wherein the recombinant MPT protein comprises N-terminal region of MPT63 involved in binding to TBK1, C-terminal region of MPT63 involved in binding to p47phox, N-terminal region of MPT64 involved in binding to TBK1, and C-terminal region of MPT64 involved in binding to HK2, and
wherein the recombinant MPT protein sequentially comprises a region involved in binding to HK2, a region involved in binding to p47phox, and a region involved in binding to TBK1.

2. The recombinant MPT protein of claim 1, wherein the N-terminal region of MPT63 involved in binding to the TBK1 comprises the amino acid sequence represented by SEQ ID NO: 6.

3. The recombinant MPT protein of claim 1, wherein the N-terminal region of MPT63 involved in binding to the TBK1 comprises the amino acid sequence represented by SEQ ID NO: 1.

4. The recombinant MPT protein of claim 1, wherein the C-terminal region of MPT63 involved in binding to the p47phox comprises the amino acid sequence represented by SEQ ID NO: 7.

5. The recombinant MPT protein of claim 1, wherein the C-terminal region of MPT63 involved in binding to the p47phox comprises the amino acid sequence represented by SEQ ID NO: 2.

6. The recombinant MPT protein of claim 1, wherein the N-terminal region of MPT64 involved in binding to the TBK1 comprises the amino acid sequence represented by SEQ ID NO: 3 and/or SEQ ID NO: 4.

7. The recombinant MPT protein of claim 1, wherein the C-terminal region of MPT64 involved in binding to the HK2 comprises the amino acid sequence represented by SEQ ID NO: 5.

8. The recombinant MPT protein of claim 1, wherein the recombinant MPT protein targets macrophages infected with *Mycobacterium tuberculosis*.

9. The recombinant MPT protein of claim 1, wherein the recombinant MPT protein increases the expression level of TNF-α and IL-6 of macrophages.

10. The recombinant MPT protein of claim 1, wherein the recombinant MPT protein reduces a secretion of IFN-β of macrophages.

11. The recombinant MPT protein of claim 1, wherein the recombinant MPT protein increases the level of cytoplasmic reactive oxygen species of macrophages.

12. A pharmaceutical composition for preventing or treating *Mycobacterium tuberculosis* infection disease comprising the recombinant MPT protein of claim 1 as an active ingredient.

13. A tuberculosis vaccine composition comprising the recombinant MPT protein of claim 1 as an active ingredient.

14. A tuberculosis vaccine adjuvant composition comprising the recombinant MPT protein of claim 1 as an active ingredient.

15. A method for preventing or treating tuberculosis, the method comprising administering the recombinant MPT protein of claim 1 to an individual.

16. The method of claim 15, wherein the method is a method for preventing tuberculosis, and wherein the method further comprises administering a Bacille de Calmette-Guerin (BCG) vaccine to the individual.

* * * * *